US009150927B2

(12) United States Patent
Huang et al.

(10) Patent No.: US 9,150,927 B2
(45) Date of Patent: Oct. 6, 2015

(54) QUANTIFICATION OF IR-A AND IR-B FOR TUMOR CLASSIFICATION

(75) Inventors: Jiaqi Huang, Potomac, MD (US); Chris Morehouse, Middletown, MD (US); Yihong Yao, Boyds, MD (US); Theresa Lavalle, Rockville, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 13/501,542

(22) PCT Filed: Oct. 11, 2010

(86) PCT No.: PCT/US2010/052173
§ 371 (c)(1),
(2), (4) Date: Jul. 26, 2012

(87) PCT Pub. No.: WO2011/046871
PCT Pub. Date: Apr. 21, 2011

(65) Prior Publication Data
US 2012/0283121 A1 Nov. 8, 2012

(51) Int. Cl.
C12Q 1/68 (2006.01)
(52) U.S. Cl.
CPC ............ *C12Q 1/6886* (2013.01); *C12Q 1/6851* (2013.01); *C12Q 1/6876* (2013.01); *C12Q 2600/106* (2013.01); *C12Q 2600/112* (2013.01); *C12Q 2600/136* (2013.01); *C12Q 2600/158* (2013.01)
(58) Field of Classification Search
CPC .............................. C12Q 1/6876; C12Q 1/6851
USPC ................ 435/6.12, 6.11; 536/241.13, 24.33
See application file for complete search history.

(56) References Cited

U.S. PATENT DOCUMENTS

| 2003/0215804 | A1  | 11/2003 | Berggren et al. |
| 2005/0256649 | A1  | 11/2005 | Roses |
| 2007/0059784 | A1* | 3/2007  | Ebina et al. ............... 435/7.23 |
| 2008/0070793 | A1* | 3/2008  | Yoon et al. ................. 506/9 |
| 2008/0081781 | A1* | 4/2008  | Lippa et al. ................. 514/3 |
| 2010/0093832 | A1* | 4/2010  | Tachas et al. .............. 514/44 A |

FOREIGN PATENT DOCUMENTS

| WO | WO03-056328   | * | 7/2003 | ............. G01N 33/48 |
| WO | WO2004-081186 | * | 8/2004 |

OTHER PUBLICATIONS

Enard W et al. Intra- and interspecific variation in primate gene expression patterns. Science. Apr. 12, 2002;296(5566):340-3.*
Whitehead A, Crawford DL. Variation in tissue-specific gene expression among natural populations. Genome Biol. 2005;6(2):R13. Epub Jan. 26, 2005.*
Rychlik W, Rhoads RE. A computer program for choosing optimal oligonucleotides for filter hybridization, sequencing and in vitro amplification of DNA. Nucleic Acids Res. 1989.17(21):8543-51.*
Sotiriou C, Piccart MJ. Taking gene-expression profiling to the clinic: when will molecular signatures become relevant to patient care? Nat Rev Cancer. 2007. 7(7):545-53. Review.*
GenBank Accession No. NM_000208.2 for the *Homo sapiens* insulin receptor (INSR), transcript variant 1, mRNA. Sep. 28, 2008 [online], [retrieved on Feb. 24, 2013], retrieved from the Internet: <URL: www.ncbi.nlm.nih.gov/nuccore/NM_000208.2>.*
Weigelt B, Reis-Filho JS, Swanton C. Genomic analyses to select patients for adjuvant chemotherapy: trials and tribulations. Ann Oncol. Sep. 2012;23 Suppl 10:x211-8.*
Sotiriou C, Pusztai L. Gene-expression signatures in breast cancer. N Engl J Med. Feb. 19, 2009; 360(8):790-800. Review.*
Sotiriou C et al., Breast cancer classification and prognosis based on gene expression profiles from a population-based study. Proc Natl Acad Sci U S A. 2003. 100(18):10393-8.*
Sørlie T et al., Distinct molecular mechanisms underlying clinically relevant subtypes of breastcancer: gene expression analyses across three different platforms. BMC Genomics. 2006. 7:127.*
Perou CM, Sørlie T,et al. Molecular portraits of human breast tumours. Nature. 2000. 406(6797):747-52.*
Aaltomaa S et al. Prognostic scores combining clinical, histological and morphometric variables in assessment of the disease outcome in female breast cancer. Int J Cancer. 1991. 49(6):886-92.*
Bacus SS, Goldschmidt R, Chin D, Moran G, Weinberg D, Bacus JW. Biological grading of breast cancer using antibodies to proliferating cells and other markers. Am J Pathol. 1989. 135(5):783-92.*
Barnard NJ, Hall PA, Lemoine NR, Kadar N. Proliferative index in breast carcinoma determined in situ by Ki67 immunostaining and its relationship to clinical and pathological variables. J Pathol. 1987. 152(4):287-95.*
Belfiore A. The role of insulin receptor isoforms and hybrid insulin/IGF-I receptors in human cancer. Curr Pharm Des. 2007.13(7):671-86. Review.*
Beresford MJ, Wilson GD, Makris A. Measuring proliferation in breast cancer: practicalities and applications. Breast Cancer Res. 2006.8(6):216. Review.*
Wirapati et al. Meta-analysis of gene expression profiles in breast cancer: toward a unified understanding of breast cancer subtyping and prognosis signatures. Breast Cancer Res. 2008;10(4):R65. Epub Jul. 28, 2008.*
Parker et al. Supervised risk predictor of breast cancer based on intrinsic subtypes. J Clin Oncol. Mar. 10, 2009;27(8):1160-7. Epub Feb. 9, 2009.*
Sciacca et al. Insulin receptor activation by IGF-II in breast cancers: evidence for a new autocrine/paracrine mechanism. Oncogene. 1999. 18(15):2471-9.*

(Continued)

*Primary Examiner* — Angela M Bertagna
*Assistant Examiner* — Olayinka Oyeyemi

(57) ABSTRACT

Without limitation, this disclosure relates to compositions and methods for detecting and quantifying the expression of insulin receptor isoform A (IR-A) and/or insulin receptor isoform B (IR-B) in a tissue sample. The disclosure also relates to methods of diagnosis and classification based at least in part upon detecting and quantifying the expression of insulin receptor isoform A (IR-A) and/or insulin B (IR-B) in a tissue sample. Methods of treating a subject based upon such a classification are among additional aspects of the disclosure presented herein.

14 Claims, 13 Drawing Sheets

(56) References Cited

OTHER PUBLICATIONS

Ravdin et al. Computer program to assist in making decisions about adjuvant therapy for women with early breast cancer. J Clin Oncol. Feb. 15, 2001;19(4):980-91.*
Oberli et al. Expression profiling with RNA from formalin-fixed, paraffin-embedded material. BMC Med Genomics. Apr. 2008..1:9.*
Peintinger F et al., Hormone receptor status and pathologic response of HER2-positive breast cancer treated with neoadjuvant chemotherapy and trastuzumab. Ann Oncol. Dec. 2008;19(12):2020-5. Epub Jul. 29, 2009.*
Liedtke C, et al. Genomic grade index is associated with response to chemotherapy in patients with breast cancer. J Clin Oncol. Jul. 1, 2009. 27(19):3185-91. Epub Apr. 13, 2009.*
Swanton C et al. Functional genomic analysis of drug sensitivity pathways to guide adjuvant strategies in breast cancer. Breast Cancer Res. 2008.10(5):214. Epub Oct. 31, 2008. Review.*
Bild et al. An integration of complementary strategies for gene-expression analysis to reveal novel therapeutic opportunities for breast cancer. Breast Cancer Res. 2009.11(4):R55. Epub Jul. 28, 2009.*
Neuvians et al. Differential expression of IGF components and insulin receptor isoforms in human seminoma versus normal testicular tissue. Neoplasia. 2005. 7(5):446-56.*
Rodon et al. Early drug development of inhibitors of the insulin-like growth factor-I receptor pathway: lessons from the first clinical trials. Mol Cancer Ther. Sep. 2008;7(9):2575-88.*
Lowe T, Sharefkin J, Yang SQ, Dieffenbach CW. A computer program for selection of oligonucleotide primers for polymerase chain reactions. Nucleic Acids Res.Apr. 11, 1990;18(7):1757-61.*
Frasca F, Pandini G, Scalia P, Sciacca L, Mineo R, Costantino A, Goldfine ID, Belfiore A, Vigneri R. Insulin receptor isoform A, a newly recognized, high-affinity insulin-like growth factor II receptor in fetal and cancer cells. Mol Cell Biol. May 1999;19(5):3278-88.*
Livak KJ, Schmittgen TD. Analysis of relative gene expression data using real-time quantitative PCR and the 2(-Delta Delta C(T)) Method. Methods. Dec. 2001; 25(4):402-8.*
Sorlie et al. Repeated observation of breast tumor subtypes in independent gene expression data sets. Proc Natl Acad Sci U S A. Jul. 8, 2003;100(14):8418-23. Epub Jun. 26, 2003.*
Sørlie et al. Distinct molecular mechanisms underlying clinically relevant subtypes of breast cancer: gene expression analyses across three different platforms. BMC Genomics. May 26, 2006;7:127.*
Genbank Accession No. XM_005259553—*Homo sapiens* insulin receptor (INSR), transcript variant X2, mRNA, complete genome (GI: 530425232, retrieved on Sep. 5, 2013 from http://www.ncbi.nlm.nih.gov/nuccore/XM_005259553.1).*
Berlato C, Doppler W. Selective response to insulin versus insulin-like growth factor-I and -II and up-regulation of insulin receptor splice variant B in the differentiated mouse mammary epithelium. Endocrinology. Jun. 2009; 150(6):2924-33. Epub.*
Pandini G, Medico E, Conte E, Sciacca L, Vigneri R, Belfiore A. Differential gene expression induced by insulin and insulin-like growth factor-II through the insulin receptor isoform A. J Biol Chem. Oct. 24, 2003;278(43):42178-89. Epub Jul. 24, 2003.*
Genbank Accession No. NM_001079817.1—*Homo sapiens* insulin receptor (INSR), transcript variant 2, mRNA, (GI: 119395737, submitted 2006, retrieved on Feb. 5, 2015 from http://www.ncbi.nlm.nih.gov/nuccore/119395737.*
Mosthaf L, Grako K, Dull TJ, Coussens L, Ullrich A, McClain DA. Functionally distinct insulin receptors generated by tissue-specific alternative splicing. EMBO J. Aug. 1990; 9(8):2409-13.*
Mosthaf L, Vogt B, Häring HU, Ullrich A. Altered expression of insulin receptor types A and B in the skeletal muscle of non-insulin-dependent diabetes mellitus patients. PNAS U S A. Jun. 1, 1991; 88(11):4728-30.*
Belfiore, A., et al. "Insulin receptors in breast cancer." Ann NY Acad Sci 784: 173-188, 1996.
Creighton, C.J., et al. "Insulin-Like Growth Factor-I Activates Gene Transcription Programs Strongly Associated With Poor Breast Cancer Prognosis." J Clin Oncol26:4078-4085, 2008.
Frasca, F., et al. "Insulin receptor isoform A, a newly recognized, high-affinity insulin-like growth factor II receptor in fetal and cancer cells." Mol Cell Bioi. May;19(5):3278-88, 1999.
Kaaks, R. "Nutrition, hormones, and breast cancer: Is insulin the missing link?" Cancer Causes Control 7:605-627, 1996.
Mathieu, M., et al. "Insulin receptor expression and clinical outcome in node-negative breast cancer." Proc Assoc Am Physicians 109:565-571,1997.
Milazzo, G., et al. "Insulin receptor expression and function in human breast cancer cell lines." Cancer Res 52:3924-3930,1992.
Moller, D.E., et al. "Tissue-specific expression of two alternatively spliced insulin receptor mRNAs in man." Mol Endocrinol. Aug;3(8): 1263-9,1989.
Neuvians, et al. "The mRNA expression of insulin receptor isoforms (IR-A and IR-B) and IGFR in the bovine corpus luteum during the estrous cycle, pregnancy, and induced luteolysis." Endocrine. 2003, 22(2):93-100.
Osborne, C.K., et al. "Correlation among insulin binding, degradation, and biological activity in human breast cancer cells in long-term tissue culture." Cancer Res 38:94-102,1978.
Paik, S. "A multigene assay to predict recurrence of tamoxifen-treated, node-negative breast cancer." N Engl J Med;351 :2817-26, 2004.
Papa, V., et al. "Elevated insulin receptor content in human breast cancer." J Clin Invest 86:1503-1510,1990.
Papa, V., et al. "Insulin receptors in breast cancer: biological and clinical role." J Endocrinol Invest 19:324-333, 1996.
Sciacca, et al, "In IGF-I receptor-deficient leiomyosarcoma cells autocrine IGF-II induces cell invasion and protection from apoptosis via the insulin receptor isoform A." Oncogene. Nov. 28; 21(54):8240-50.9, 2002.
Seino, S., et al. "Structure of the human insulin receptor gene and characterization of its promoter." Proc Natl Acad Sci USA. Jan; 86(1)114-8,1989.
International Search Report mailed Feb. 28, 2011, in International Application No. PCT/2010/52173, filed Oct. 11, 2010.
Chisalita, S I, et al., 2009, "Human aortic smooth muscle cells are insulin resistant at the receptor level but sensitive to IGF1 and IGF2", Journal of Molecular Endocrinology, 43:231-239.

* cited by examiner

FIGURE 2

```
IR-A    MGTGGRRGAAAAPLLVAVAALLLGAAGHLYPGEVCPGMDIRNNLTRLHELENCSVIEGHL     60
IR-B    MGTGGRRGAAAAPLLVAVAALLLGAAGHLYPGEVCPGMDIRNNLTRLHELENCSVIEGHL     60
        |————SIGNAL PEPTIDE————| |——α-Subunit——▶
IR-A    QILLMFKTRPEDFRDLSFPKLIMITDYLLLFRVYGLESLKDLFPNLTVIRGSRLFFNYAL    120
IR-B    QILLMFKTRPEDFRDLSFPKLIMITDYLLLFRVYGLESLKDLFPNLTVIRGSRLFFNYAL    120

IR-A    VIFEMVHLKELGLYNLMNITRGSVRIEKNNELCYLATIDWSRILDSVEDNYIVLNKDDNE    180
IR-B    VIFEMVHLKELGLYNLMNITRGSVRIEKNNELCYLATIDWSRILDSVEDNYIVLNKDDNE    180

IR-A    ECGDICPGTAKGKTNCPATVINGQFVERCWTHSHCQKVCPTICKSHGCTAEGLCCHSECL    240
IR-B    ECGDICPGTAKGKTNCPATVINGQFVERCWTHSHCQKVCPTICKSHGCTAEGLCCHSECL    240

IR-A    GNCSQPDDPTKCVACRNFYLDGRCVETCPPPYYHFQDWRCVNFSFCQDLHHKCKNSRRQG    300
IR-B    GNCSQPDDPTKCVACRNFYLDGRCVETCPPPYYHFQDWRCVNFSFCQDLHHKCKNSRRQG    300

IR-A    CHQYVIHNNKCIPECPSGYTMNSSNLLCTPCLGPCPKVCHLLEGEKTIDSVTSAQELRGC    360
IR-B    CHQYVIHNNKCIPECPSGYTMNSSNLLCTPCLGPCPKVCHLLEGEKTIDSVTSAQELRGC    360

IR-A    TVINGSLIINIRGGNNLAAELEANLGLIEEISGYLKIRRSYALVSLSFFRKLRLIRGETL    420
IR-B    TVINGSLIINIRGGNNLAAELEANLGLIEEISGYLKIRRSYALVSLSFFRKLRLIRGETL    420

IR-A    EIGNYSFYALDNQNLRQLWDWSKHNLTITQGKLFFHYNPKLCLSEIHKMEEVSGTKGRQE    480
IR-B    EIGNYSFYALDNQNLRQLWDWSKHNLTITQGKLFFHYNPKLCLSEIHKMEEVSGTKGRQE    480

IR-A    RNDIALKTNGDQASCENELLKFSYIRTSFDKILLRWEPYWPPDFRDLLGFMLFYKEAPYQ    540
IR-B    RNDIALKTNGDQASCENELLKFSYIRTSFDKILLRWEPYWPPDFRDLLGFMLFYKEAPYQ    540

IR-A    NVTEFDGQDACGSNSWTVVDIDPPLRSNDPKSQNHPGWLMRGLKPWTQYAIFVKTLVTFS    600
IR-B    NVTEFDGQDACGSNSWTVVDIDPPLRSNDPKSQNHPGWLMRGLKPWTQYAIFVKTLVTFS    600

IR-A    DERRTYGAKSDIIYVQTDATNPSVPLDPISVSNSSSQIILKWKPPSDPNGNITHYLVFWE    660
IR-B    DERRTYGAKSDIIYVQTDATNPSVPLDPISVSNSSSQIILKWKPPSDPNGNITHYLVFWE    660

IR-A    RQAEDSELFELDYCLKGLKLPSRTWSPPFESEDSQKHNQSEYEDSAGECCSCPKTDSQIL    720
IR-B    RQAEDSELFELDYCLKGLKLPSRTWSPPFESEDSQKHNQSEYEDSAGECCSCPKTDSQIL    720

IR-A    KELEESSFRKTFEDYLHNVVFVP------------RPSRKRRSLGDVGNVTVAVPTVAAF    768
IR-B    KELEESSFRKTFEDYLHNVVFVPRKTSSGTGAEDPRPSRKRRSLGDVGNVTVAVPTVAAF    780
                             |——EXON 11——| | |——β-Subunit——▶
IR-A    PNTSSTSVPTSPEEHRPFEKVVNKESLVISGLRHFTGYRIELQACNQDTPEERCSVAAYV    828
IR-B    PNTSSTSVPTSPEEHRPFEKVVNKESLVISGLRHFTGYRIELQACNQDTPEERCSVAAYV    840

IR-A    SARTMPEAKADDIVGPVTHEIFENNVVHLMWQEPKEPNGLIVLYEVSYRRYGDEELHLCV    888
IR-B    SARTMPEAKADDIVGPVTHEIFENNVVHLMWQEPKEPNGLIVLYEVSYRRYGDEELHLCV    900

IR-A    SRKHFALERGCRLRGLSPGNYSVRIRATSLAGNGSWTEPTYFYVTDYLDVPSNIAKIIIG    948
IR-B    SRKHFALERGCRLRGLSPGNYSVRIRATSLAGNGSWTEPTYFYVTDYLDVPSNIAKIIIG    960

IR-A    PLIFVFLFSVVIGSIYLFLRKRQPDGPLGPLYASSNPEYLSASDVFPCSVYVPDEWEVSR   1008
IR-B    PLIFVFLFSVVIGSIYLFLRKRQPDGPLGPLYASSNPEYLSASDVFPCSVYVPDEWEVSR   1020

IR-A    EKITLLRELGQGSFGMVYEGNARDIIKGEAETRVAVKTVNESASLRERIEFLNEASVMKG   1068
IR-B    EKITLLRELGQGSFGMVYEGNARDIIKGEAETRVAVKTVNESASLRERIEFLNEASVMKG   1080

IR-A    FTCHHVVRLLGVVSKGQPTLVVMELMAHGDLKSYLRSLRPEAENNPGRPPPTLQEMIQMA   1128
IR-B    FTCHHVVRLLGVVSKGQPTLVVMELMAHGDLKSYLRSLRPEAENNPGRPPPTLQEMIQMA   1140

IR-A    AEIADGMAYLNAKKFVHRDLAARNCMVAHDFTVKIGDFGMTRDIYETDYYRKGGKGLLPV   1188
IR-B    AEIADGMAYLNAKKFVHRDLAARNCMVAHDFTVKIGDFGMTRDIYETDYYRKGGKGLLPV   1200

IR-A    RWMAPESLKDGVFTTSSDMWSFGVVLWEITSLAEQPYQGLSNEQVLKFVMDGGYLDQPDN   1248
IR-B    RWMAPESLKDGVFTTSSDMWSFGVVLWEITSLAEQPYQGLSNEQVLKFVMDGGYLDQPDN   1260

IR-A    CPERVTDLMRMCWQFNPKMRPTFLEIVNLLKDDLHPSFPEVSFFHSEENKAPESEELEME   1308
IR-B    CPERVTDLMRMCWQFNPKMRPTFLEIVNLLKDDLHPSFPEVSFFHSEENKAPESEELEME   1320

IR-A    FEDMENVPLDRSSHCQREEAGGRDGGSSLGFKRSYEEHIPYTHMNGGKKNGRILTLPRSNPS  1370
IR-B    FEDMENVPLDRSSHCQREEAGGRDGGSSLGFKRSYEEHIPYTHMNGGKKNGRILTLPRSNPS  1382
```

FIGURE 4 ggctgaagctgccctcgaggacctggtctccaccattcgagtctgaagattctcagaagc
Exon 10
acaaccagagtgagtatgaggattcggccggcgaatgctgctcctgtccaaagacagact ctcagatcctgaaggagctggaggagtcctcgtttaggaagacgtttgaggattacctgc
                                                           |———Forward—
acaacgtggttttcgtccccagGCCATCTCGGAAACGCAGGTCCCTTGGCGATGTTGGGA
Primer▶     ===PROBE===                         ◀—Reverse
ATGTGACGGTGGCCGTGCCCACGGTGGCAGCTTTCCCCAACACTTCCTCGACCAGCGTGC
—Primer————————|
CCACGAGTCCGGAGGAGCACAGGCCTTTTGAGAAGGTGGTGAACAAGGAGTCGCTGGTCA TCTCCGGCTTGCGACACTTCACGGGCTATCGCATCGAGCTGCAGGCTTGCAACCAGGACA
                                                                Exon 12
CCCCTGAGGAACGGTGCAGTGTGGCAGCCTACGTCAGTGCGAGGACCATGCCTGAAG

FIGURE 5 ggctgaagctgccctcgaggacctggtctccaccattcgagtctgaagattctcagaagc
Exon 10
acaaccagagtgagtatgaggattcggccggcgaatgctgctcctgtccaaagacagact ctcagatcctgaaggagctggaggagtcctcgtttaggaagacgtttgaggattacctgc
                                                             |—Forward-Primer
acaacgtggttttcgtccccagGCCATCTCGGAAACGCAGGTCCCTTGGCGATGTTGGGA
——→      ===PROBE===      ←Reverse-Primer|
ATGTGACGGTGGCCGTGCCCACGGTGGCAGCTTTCCCCAACACTTCCTCGACCAGCGTGC

CCACGAGTCCGGAGGAGCACAGGCCTTTTGAGAAGGTGGTGAACAAGGAGTCGCTGGTCA

TCTCCGGCTTGCGACACTTCACGGGCTATCGCATCGAGCTGCAGGCTTGCAACCAGGACA
                                                                       Exon 12
CCCCTGAGGAACGGTGCAGTGTGGCAGCCTACGTCAGTGCGAGGACCATGCCTGAAG

FIGURE 6

```
ggctgaagctgccctcgaggacctggtctccaccattcgagtctgaagattctcagaagc
Exon 10
acaaccagagtgagtatgaggattcggccggcgaatgctgctcctgtccaaagacagact ctcagatcctgaaggagctggaggagtcctcgtttaggaagacgtttgaggattacctgc acaacgtggttttcgtccccagAAAAACCTCTTCAGGCACTGGTGCCGAGGACCCTAGgcc
                   Exon 11                   ═══Probe IRB4═══
            ├─Forward Primer──▶        ═══Probe IRB3═══
                                   ═══Probe IRB5═══
atctcggaaacgcaggtcccttggcgatgttgggaatgtgacggtggccgtgcccacggtg
◀─Reverse Primer─┤
gcagctttccccaacacttcctcgaccagcgtgcccacgagtccggaggagcacaggcctt ttgagaaggtggtgaacaaggagtcgctggtcatctccggcttgcgacacttcacgggcta tcgcatcgagctgcaggcttgcaaccaggacacccctgaggaacggtgcagtgtggcagcc
                Exon 12
tacgtcagtgcgaggaccatgcctgaag
```

FIGURE 13
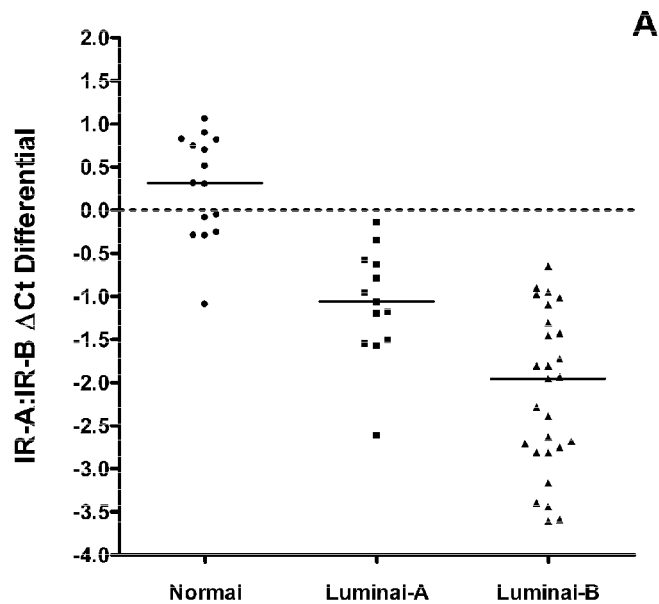
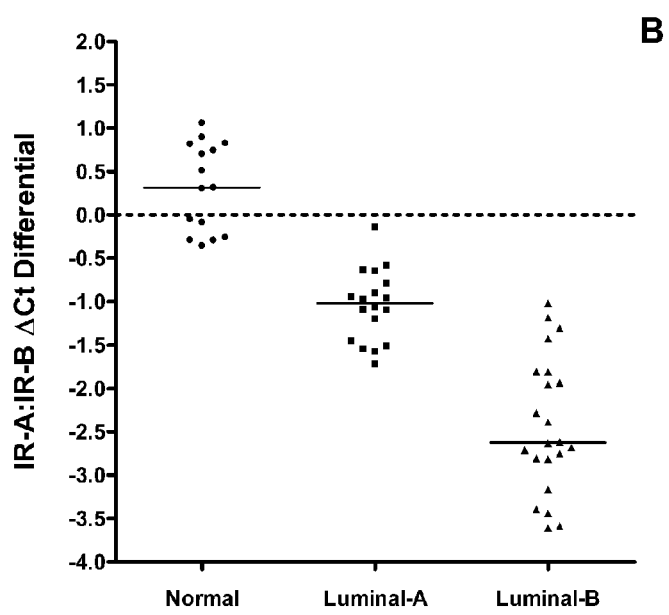

```
                            SEQUENCE LISTING

<160> NUMBER OF SEQ ID NOS: 59

<210> SEQ ID NO 1
<211> LENGTH: 50
<212> TYPE: DNA
<213> ORGANISM: Homo sapiens

<400> SEQUENCE: 1
tttaggaaga cgtttgagga ttacctgcac aacgtggttt tcgtccccag              50

<210> SEQ ID NO 2
<211> LENGTH: 60
<212> TYPE: DNA
<213> ORGANISM: Homo sapiens

<400> SEQUENCE: 2
gccatctcgg aaacgcaggt cccttggcga tgttgggaat gtgacggtgg ccgtgcccac   60

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgaggattac ctgcacaacg                                               20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatgttggga atgtgacggt                                               20

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ttgaggatta cctgcacaac gt                                            22

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aaacgcaggt cccttggc                                                 18

<210> SEQ ID NO 7
```

```
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tccccaggcc atct                                                        14

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
ttttcgtccc caggcca                                                     17

<210> SEQ ID NO 9
<211> LENGTH: 36
<212> TYPE: DNA
<213> ORGANISM: Homo sapiens

<400> SEQUENCE: 9
aaaaacctct tcaggcactg gtgcccagga ccctag                                36

<210> SEQ ID NO 10
<211> LENGTH: 50
<212> TYPE: DNA
<213> ORGANISM: Homo sapiens

<400> SEQUENCE: 10
gccatctcgg aaacgcaggt cccttggcga tgttgggaat gtgacggtgg                 50

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cgtccccaga aaaacctctt c                                                21

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggacctgcgt ttccgagat                                                   19

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 13
actggtgccg aggac                                              15

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
ccgaggaccc taggc                                              15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tgccgaggac cctag                                              15

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
caggccatct cggaaacg                                           18

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctggtgccga ggaccctagg                                         20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctgcacaacg tggttttcgt                                         20

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
```

```
ttgaggatta cctgcacaac gt                                             22
```

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20

```
acggccaccg tcacattc                                                  18
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
accgtcacat tcccaacatc                                                20
```

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
gccaagggac ctgcgttt                                                  18
```

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23

```
caccgtcaca ttcccaacat c                                              21
```

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24

```
aggtcccttg gcgatg                                                    16
```

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
caggccatct cggaaa                                                          16

<210> SEQ ID NO 26
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
ttcgtcccca ggcca                                                           15

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
accctaggcc atctcggaaa                                                      20

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cacggccacc gtcacatt                                                        18

<210> SEQ ID NO 29
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
ccttggcgat gttgg                                                           15

<210> SEQ ID NO 30
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
gaggacccta ggcca                                                           15

<210> SEQ ID NO 31
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
tgccgaggac ccta                                                            14

<210> SEQ ID NO 32
<211> LENGTH: 1370
<212> TYPE: PRT
<213> ORGANISM: Homo sapiens

<400> SEQUENCE: 32

```
Met Gly Thr Gly Gly Arg Arg Gly Ala Ala Ala Pro Leu Leu Val
1               5                   10                  15

Ala Val Ala Ala Leu Leu Leu Gly Ala Ala Gly His Leu Tyr Pro Gly
            20                  25                  30

Glu Val Cys Pro Gly Met Asp Ile Arg Asn Asn Leu Thr Arg Leu His
            35                  40                  45

Glu Leu Glu Asn Cys Ser Val Ile Glu Gly His Leu Gln Ile Leu Leu
50                  55                  60

Met Phe Lys Thr Arg Pro Glu Asp Phe Arg Asp Leu Ser Phe Pro Lys
65                  70                  75                  80

Leu Ile Met Ile Thr Asp Tyr Leu Leu Leu Phe Arg Val Tyr Gly Leu
                85                  90                  95

Glu Ser Leu Lys Asp Leu Phe Pro Asn Leu Thr Val Ile Arg Gly Ser
            100                 105                 110

Arg Leu Phe Phe Asn Tyr Ala Leu Val Ile Phe Glu Met Val His Leu
            115                 120                 125

Lys Glu Leu Gly Leu Tyr Asn Leu Met Asn Ile Thr Arg Gly Ser Val
            130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn Tyr Ile Val Leu Asn Lys
                165                 170                 175

Asp Asp Asn Glu Glu Cys Gly Asp Ile Cys Pro Gly Thr Ala Lys Gly
            180                 185                 190

Lys Thr Asn Cys Pro Ala Thr Val Ile Asn Gly Gln Phe Val Glu Arg
            195                 200                 205

Cys Trp Thr His Ser His Cys Gln Lys Val Cys Pro Thr Ile Cys Lys
            210                 215                 220

Ser His Gly Cys Thr Ala Glu Gly Leu Cys Cys His Ser Glu Cys Leu
225                 230                 235                 240

Gly Asn Cys Ser Gln Pro Asp Asp Pro Thr Lys Cys Val Ala Cys Arg
                245                 250                 255

Asn Phe Tyr Leu Asp Gly Arg Cys Val Glu Thr Cys Pro Pro Pro Tyr
            260                 265                 270

Tyr His Phe Gln Asp Trp Arg Cys Val Asn Phe Ser Phe Cys Gln Asp
            275                 280                 285

Leu His His Lys Cys Lys Asn Ser Arg Arg Gln Gly Cys His Gln Tyr
290                 295                 300

Val Ile His Asn Asn Lys Cys Ile Pro Glu Cys Pro Ser Gly Tyr Thr
305                 310                 315                 320

Met Asn Ser Ser Asn Leu Leu Cys Thr Pro Cys Leu Gly Pro Cys Pro
                325                 330                 335

Lys Val Cys His Leu Leu Glu Gly Glu Lys Thr Ile Asp Ser Val Thr
            340                 345                 350

Ser Ala Gln Glu Leu Arg Gly Cys Thr Val Ile Asn Gly Ser Leu Ile
            355                 360                 365

Ile Asn Ile Arg Gly Gly Asn Asn Leu Ala Ala Glu Leu Glu Ala Asn
```

```
                 370                 375                 380
Leu Gly Leu Ile Glu Glu Ile Ser Gly Tyr Leu Lys Ile Arg Arg Ser
385                 390                 395                 400

Tyr Ala Leu Val Ser Leu Ser Phe Phe Arg Lys Leu Arg Leu Ile Arg
                405                 410                 415

Gly Glu Thr Leu Glu Ile Gly Asn Tyr Ser Phe Tyr Ala Leu Asp Asn
            420                 425                 430

Gln Asn Leu Arg Gln Leu Trp Asp Trp Ser Lys His Asn Leu Thr Ile
        435                 440                 445

Thr Gln Gly Lys Leu Phe Phe His Tyr Asn Pro Lys Leu Cys Leu Ser
450                 455                 460

Glu Ile His Lys Met Glu Glu Val Ser Gly Thr Lys Gly Arg Gln Glu
465                 470                 475                 480

Arg Asn Asp Ile Ala Leu Lys Thr Asn Gly Asp Gln Ala Ser Cys Glu
                485                 490                 495

Asn Glu Leu Leu Lys Phe Ser Tyr Ile Arg Thr Ser Phe Asp Lys Ile
            500                 505                 510

Leu Leu Arg Trp Glu Pro Tyr Trp Pro Asp Phe Arg Asp Leu Leu
        515                 520                 525

Gly Phe Met Leu Phe Tyr Lys Glu Ala Pro Tyr Gln Asn Val Thr Glu
530                 535                 540

Phe Asp Gly Gln Asp Ala Cys Gly Ser Asn Ser Trp Thr Val Val Asp
545                 550                 555                 560

Ile Asp Pro Pro Leu Arg Ser Asn Asp Pro Lys Ser Gln Asn His Pro
                565                 570                 575

Gly Trp Leu Met Arg Gly Leu Lys Pro Trp Thr Gln Tyr Ala Ile Phe
            580                 585                 590

Val Lys Thr Leu Val Thr Phe Ser Asp Glu Arg Arg Thr Tyr Gly Ala
        595                 600                 605

Lys Ser Asp Ile Ile Tyr Val Gln Thr Asp Ala Thr Asn Pro Ser Val
610                 615                 620

Pro Leu Asp Pro Ile Ser Val Ser Asn Ser Ser Ser Gln Ile Ile Leu
625                 630                 635                 640

Lys Trp Lys Pro Pro Ser Asp Pro Asn Gly Asn Ile Thr His Tyr Leu
                645                 650                 655

Val Phe Trp Glu Arg Gln Ala Glu Asp Ser Glu Leu Phe Glu Leu Asp
            660                 665                 670

Tyr Cys Leu Lys Gly Leu Lys Leu Pro Ser Arg Thr Trp Ser Pro Pro
        675                 680                 685

Phe Glu Ser Glu Asp Ser Gln Lys His Asn Gln Ser Glu Tyr Glu Asp
690                 695                 700

Ser Ala Gly Glu Cys Cys Ser Cys Pro Lys Thr Asp Ser Gln Ile Leu
705                 710                 715                 720

Lys Glu Leu Glu Glu Ser Ser Phe Arg Lys Thr Phe Glu Asp Tyr Leu
                725                 730                 735

His Asn Val Val Phe Val Pro Arg Pro Ser Arg Lys Arg Arg Ser Leu
            740                 745                 750

Gly Asp Val Gly Asn Val Thr Val Ala Val Pro Thr Val Ala Ala Phe
        755                 760                 765

Pro Asn Thr Ser Ser Thr Ser Val Pro Thr Ser Pro Glu Glu His Arg
770                 775                 780

Pro Phe Glu Lys Val Val Asn Lys Glu Ser Leu Val Ile Ser Gly Leu
785                 790                 795                 800
```

-continued

Arg His Phe Thr Gly Tyr Arg Ile Glu Leu Gln Ala Cys Asn Gln Asp
            805                 810                 815

Thr Pro Glu Glu Arg Cys Ser Val Ala Ala Tyr Val Ser Ala Arg Thr
            820                 825                 830

Met Pro Glu Ala Lys Ala Asp Asp Ile Val Gly Pro Val Thr His Glu
            835                 840                 845

Ile Phe Glu Asn Asn Val Val His Leu Met Trp Gln Glu Pro Lys Glu
            850                 855                 860

Pro Asn Gly Leu Ile Val Leu Tyr Glu Val Ser Tyr Arg Arg Tyr Gly
865                 870                 875                 880

Asp Glu Glu Leu His Leu Cys Val Ser Arg Lys His Phe Ala Leu Glu
            885                 890                 895

Arg Gly Cys Arg Leu Arg Gly Leu Ser Pro Gly Asn Tyr Ser Val Arg
            900                 905                 910

Ile Arg Ala Thr Ser Leu Ala Gly Asn Gly Ser Trp Thr Glu Pro Thr
            915                 920                 925

Tyr Phe Tyr Val Thr Asp Tyr Leu Asp Val Pro Ser Asn Ile Ala Lys
            930                 935                 940

Ile Ile Ile Gly Pro Leu Ile Phe Val Phe Leu Phe Ser Val Val Ile
945                 950                 955                 960

Gly Ser Ile Tyr Leu Phe Leu Arg Lys Arg Gln Pro Asp Gly Pro Leu
            965                 970                 975

Gly Pro Leu Tyr Ala Ser Ser Asn Pro Glu Tyr Leu Ser Ala Ser Asp
            980                 985                 990

Val Phe Pro Cys Ser Val Tyr Val Pro Asp Glu Trp Glu Val Ser Arg
            995                 1000                1005

Glu Lys Ile Thr Leu Leu Arg Glu Leu Gly Gln Gly Ser Phe Gly
    1010                1015                1020

Met Val Tyr Glu Gly Asn Ala Arg Asp Ile Ile Lys Gly Glu Ala
    1025                1030                1035

Glu Thr Arg Val Ala Val Lys Thr Val Asn Glu Ser Ala Ser Leu
    1040                1045                1050

Arg Glu Arg Ile Glu Phe Leu Asn Glu Ala Ser Val Met Lys Gly
    1055                1060                1065

Phe Thr Cys His His Val Val Arg Leu Leu Gly Val Val Ser Lys
    1070                1075                1080

Gly Gln Pro Thr Leu Val Val Met Glu Leu Met Ala His Gly Asp
    1085                1090                1095

Leu Lys Ser Tyr Leu Arg Ser Leu Arg Pro Glu Ala Glu Asn Asn
    1100                1105                1110

Pro Gly Arg Pro Pro Pro Thr Leu Gln Glu Met Ile Gln Met Ala
    1115                1120                1125

Ala Glu Ile Ala Asp Gly Met Ala Tyr Leu Asn Ala Lys Lys Phe
    1130                1135                1140

Val His Arg Asp Leu Ala Ala Arg Asn Cys Met Val Ala His Asp
    1145                1150                1155

Phe Thr Val Lys Ile Gly Asp Phe Gly Met Thr Arg Asp Ile Tyr
    1160                1165                1170

Glu Thr Asp Tyr Tyr Arg Lys Gly Gly Lys Gly Leu Leu Pro Val
    1175                1180                1185

Arg Trp Met Ala Pro Glu Ser Leu Lys Asp Gly Val Phe Thr Thr
    1190                1195                1200

```
Ser Ser Asp Met Trp Ser Phe Gly Val Val Leu Trp Glu Ile Thr
    1205                1210                1215

Ser Leu Ala Glu Gln Pro Tyr Gln Gly Leu Ser Asn Glu Gln Val
    1220                1225                1230

Leu Lys Phe Val Met Asp Gly Gly Tyr Leu Asp Gln Pro Asp Asn
    1235                1240                1245

Cys Pro Glu Arg Val Thr Asp Leu Met Arg Met Cys Trp Gln Phe
    1250                1255                1260

Asn Pro Lys Met Arg Pro Thr Phe Leu Glu Ile Val Asn Leu Leu
    1265                1270                1275

Lys Asp Asp Leu His Pro Ser Phe Pro Glu Val Ser Phe Phe His
    1280                1285                1290

Ser Glu Glu Asn Lys Ala Pro Glu Ser Glu Glu Leu Glu Met Glu
    1295                1300                1305

Phe Glu Asp Met Glu Asn Val Pro Leu Asp Arg Ser Ser His Cys
    1310                1315                1320

Gln Arg Glu Glu Ala Gly Gly Arg Asp Gly Gly Ser Ser Leu Gly
    1325                1330                1335

Phe Lys Arg Ser Tyr Glu Glu His Ile Pro Tyr Thr His Met Asn
    1340                1345                1350

Gly Gly Lys Lys Asn Gly Arg Ile Leu Thr Leu Pro Arg Ser Asn
    1355                1360                1365

Pro Ser
    1370

<210> SEQ ID NO 33
<211> LENGTH: 1382
<212> TYPE: PRT
<213> ORGANISM: Homo sapiens

<400> SEQUENCE: 33

Met Gly Thr Gly Gly Arg Arg Gly Ala Ala Ala Ala Pro Leu Leu Val
1               5                   10                  15

Ala Val Ala Ala Leu Leu Leu Gly Ala Ala Gly His Leu Tyr Pro Gly
                20                  25                  30

Glu Val Cys Pro Gly Met Asp Ile Arg Asn Asn Leu Thr Arg Leu His
            35                  40                  45

Glu Leu Glu Asn Cys Ser Val Ile Glu Gly His Leu Gln Ile Leu Leu
        50                  55                  60

Met Phe Lys Thr Arg Pro Glu Asp Phe Arg Asp Leu Ser Phe Pro Lys
65                  70                  75                  80

Leu Ile Met Ile Thr Asp Tyr Leu Leu Leu Phe Arg Val Tyr Gly Leu
                85                  90                  95

Glu Ser Leu Lys Asp Leu Phe Pro Asn Leu Thr Val Ile Arg Gly Ser
                100                 105                 110

Arg Leu Phe Phe Asn Tyr Ala Leu Val Ile Phe Glu Met Val His Leu
            115                 120                 125

Lys Glu Leu Gly Leu Tyr Asn Leu Met Asn Ile Thr Arg Gly Ser Val
        130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn Tyr Ile Val Leu Asn Lys
                165                 170                 175

Asp Asp Asn Glu Glu Cys Gly Asp Ile Cys Pro Gly Thr Ala Lys Gly
                180                 185                 190
```

-continued

```
Lys Thr Asn Cys Pro Ala Thr Val Ile Asn Gly Gln Phe Val Glu Arg
    195                 200                 205
Cys Trp Thr His Ser His Cys Gln Lys Val Cys Pro Thr Ile Cys Lys
210                 215                 220
Ser His Gly Cys Thr Ala Glu Gly Leu Cys Cys His Ser Glu Cys Leu
225                 230                 235                 240
Gly Asn Cys Ser Gln Pro Asp Asp Pro Thr Lys Cys Val Ala Cys Arg
                245                 250                 255
Asn Phe Tyr Leu Asp Gly Arg Cys Val Glu Thr Cys Pro Pro Pro Tyr
            260                 265                 270
Tyr His Phe Gln Asp Trp Arg Cys Val Asn Phe Ser Phe Cys Gln Asp
        275                 280                 285
Leu His His Lys Cys Lys Asn Ser Arg Arg Gln Gly Cys His Gln Tyr
    290                 295                 300
Val Ile His Asn Asn Lys Cys Ile Pro Glu Cys Pro Ser Gly Tyr Thr
305                 310                 315                 320
Met Asn Ser Ser Asn Leu Leu Cys Thr Pro Cys Leu Gly Pro Cys Pro
                325                 330                 335
Lys Val Cys His Leu Leu Glu Gly Glu Lys Thr Ile Asp Ser Val Thr
            340                 345                 350
Ser Ala Gln Glu Leu Arg Gly Cys Thr Val Ile Asn Gly Ser Leu Ile
        355                 360                 365
Ile Asn Ile Arg Gly Gly Asn Asn Leu Ala Ala Glu Leu Glu Ala Asn
    370                 375                 380
Leu Gly Leu Ile Glu Glu Ile Ser Gly Tyr Leu Lys Ile Arg Arg Ser
385                 390                 395                 400
Tyr Ala Leu Val Ser Leu Ser Phe Phe Arg Lys Leu Arg Leu Ile Arg
                405                 410                 415
Gly Glu Thr Leu Glu Ile Gly Asn Tyr Ser Phe Tyr Ala Leu Asp Asn
            420                 425                 430
Gln Asn Leu Arg Gln Leu Trp Asp Trp Ser Lys His Asn Leu Thr Ile
        435                 440                 445
Thr Gln Gly Lys Leu Phe Phe His Tyr Asn Pro Lys Leu Cys Leu Ser
    450                 455                 460
Glu Ile His Lys Met Glu Glu Val Ser Gly Thr Lys Gly Arg Gln Glu
465                 470                 475                 480
Arg Asn Asp Ile Ala Leu Lys Thr Asn Gly Asp Gln Ala Ser Cys Glu
                485                 490                 495
Asn Glu Leu Leu Lys Phe Ser Tyr Ile Arg Thr Ser Phe Asp Lys Ile
            500                 505                 510
Leu Leu Arg Trp Glu Pro Tyr Trp Pro Pro Asp Phe Arg Asp Leu Leu
        515                 520                 525
Gly Phe Met Leu Phe Tyr Lys Glu Ala Pro Tyr Gln Asn Val Thr Glu
    530                 535                 540
Phe Asp Gly Gln Asp Ala Cys Gly Ser Asn Ser Trp Thr Val Val Asp
545                 550                 555                 560
Ile Asp Pro Pro Leu Arg Ser Asn Asp Pro Lys Ser Gln Asn His Pro
                565                 570                 575
Gly Trp Leu Met Arg Gly Leu Lys Pro Trp Thr Gln Tyr Ala Ile Phe
            580                 585                 590
Val Lys Thr Leu Val Thr Phe Ser Asp Glu Arg Arg Thr Tyr Gly Ala
        595                 600                 605
```

-continued

```
Lys Ser Asp Ile Ile Tyr Val Gln Thr Asp Ala Thr Asn Pro Ser Val
    610                 615                 620

Pro Leu Asp Pro Ile Ser Val Ser Asn Ser Ser Gln Ile Ile Leu
625                 630                 635                 640

Lys Trp Lys Pro Pro Ser Asp Pro Asn Gly Asn Ile Thr His Tyr Leu
                645                 650                 655

Val Phe Trp Glu Arg Gln Ala Glu Asp Ser Glu Leu Phe Glu Leu Asp
            660                 665                 670

Tyr Cys Leu Lys Gly Leu Lys Leu Pro Ser Arg Thr Trp Ser Pro Pro
        675                 680                 685

Phe Glu Ser Glu Asp Ser Gln Lys His Asn Gln Ser Glu Tyr Glu Asp
690                 695                 700

Ser Ala Gly Glu Cys Cys Ser Cys Pro Lys Thr Asp Ser Gln Ile Leu
705                 710                 715                 720

Lys Glu Leu Glu Glu Ser Ser Phe Arg Lys Thr Phe Glu Asp Tyr Leu
                725                 730                 735

His Asn Val Val Phe Val Pro Arg Lys Thr Ser Ser Gly Thr Gly Ala
            740                 745                 750

Glu Asp Pro Arg Pro Ser Arg Lys Arg Arg Ser Leu Gly Asp Val Gly
        755                 760                 765

Asn Val Thr Val Ala Val Pro Thr Val Ala Ala Phe Pro Asn Thr Ser
770                 775                 780

Ser Thr Ser Val Pro Thr Ser Pro Glu Glu His Arg Pro Phe Glu Lys
785                 790                 795                 800

Val Val Asn Lys Glu Ser Leu Val Ile Ser Gly Leu Arg His Phe Thr
                805                 810                 815

Gly Tyr Arg Ile Glu Leu Gln Ala Cys Asn Gln Asp Thr Pro Glu Glu
            820                 825                 830

Arg Cys Ser Val Ala Ala Tyr Val Ser Ala Arg Thr Met Pro Glu Ala
        835                 840                 845

Lys Ala Asp Asp Ile Val Gly Pro Val Thr His Glu Ile Phe Glu Asn
850                 855                 860

Asn Val Val His Leu Met Trp Gln Glu Pro Lys Glu Pro Asn Gly Leu
865                 870                 875                 880

Ile Val Leu Tyr Glu Val Ser Tyr Arg Arg Tyr Gly Asp Glu Glu Leu
                885                 890                 895

His Leu Cys Val Ser Arg Lys His Phe Ala Leu Glu Arg Gly Cys Arg
            900                 905                 910

Leu Arg Gly Leu Ser Pro Gly Asn Tyr Ser Val Arg Ile Arg Ala Thr
        915                 920                 925

Ser Leu Ala Gly Asn Gly Ser Trp Thr Glu Pro Thr Tyr Phe Tyr Val
930                 935                 940

Thr Asp Tyr Leu Asp Val Pro Ser Asn Ile Ala Lys Ile Ile Ile Gly
945                 950                 955                 960

Pro Leu Ile Phe Val Phe Leu Phe Ser Val Val Ile Gly Ser Ile Tyr
                965                 970                 975

Leu Phe Leu Arg Lys Arg Gln Pro Asp Gly Pro Leu Gly Pro Leu Tyr
            980                 985                 990

Ala Ser Ser Asn Pro Glu Tyr Leu  Ser Ala Ser Asp Val  Phe Pro Cys
        995                 1000                 1005

Ser Val  Tyr Val Pro Asp Glu  Trp Glu Val Ser Arg  Glu Lys Ile
    1010                 1015                 1020

Thr Leu  Leu Arg Glu Leu Gly  Gln Gly Ser Phe Gly  Met Val Tyr
```

1025                1030                1035

Glu Gly Asn Ala Arg Asp Ile Ile Lys Gly Glu Ala Glu Thr Arg
    1040                1045                1050

Val Ala Val Lys Thr Val Asn Glu Ser Ala Ser Leu Arg Glu Arg
    1055                1060                1065

Ile Glu Phe Leu Asn Glu Ala Ser Val Met Lys Gly Phe Thr Cys
    1070                1075                1080

His His Val Val Arg Leu Leu Gly Val Val Ser Lys Gly Gln Pro
    1085                1090                1095

Thr Leu Val Val Met Glu Leu Met Ala His Gly Asp Leu Lys Ser
    1100                1105                1110

Tyr Leu Arg Ser Leu Arg Pro Glu Ala Glu Asn Asn Pro Gly Arg
    1115                1120                1125

Pro Pro Pro Thr Leu Gln Glu Met Ile Gln Met Ala Ala Glu Ile
    1130                1135                1140

Ala Asp Gly Met Ala Tyr Leu Asn Ala Lys Lys Phe Val His Arg
    1145                1150                1155

Asp Leu Ala Ala Arg Asn Cys Met Val Ala His Asp Phe Thr Val
    1160                1165                1170

Lys Ile Gly Asp Phe Gly Met Thr Arg Asp Ile Tyr Glu Thr Asp
    1175                1180                1185

Tyr Tyr Arg Lys Gly Gly Lys Gly Leu Leu Pro Val Arg Trp Met
    1190                1195                1200

Ala Pro Glu Ser Leu Lys Asp Gly Val Phe Thr Thr Ser Ser Asp
    1205                1210                1215

Met Trp Ser Phe Gly Val Val Leu Trp Glu Ile Thr Ser Leu Ala
    1220                1225                1230

Glu Gln Pro Tyr Gln Gly Leu Ser Asn Glu Gln Val Leu Lys Phe
    1235                1240                1245

Val Met Asp Gly Gly Tyr Leu Asp Gln Pro Asp Asn Cys Pro Glu
    1250                1255                1260

Arg Val Thr Asp Leu Met Arg Met Cys Trp Gln Phe Asn Pro Lys
    1265                1270                1275

Met Arg Pro Thr Phe Leu Glu Ile Val Asn Leu Leu Lys Asp Asp
    1280                1285                1290

Leu His Pro Ser Phe Pro Glu Val Ser Phe Phe His Ser Glu Glu
    1295                1300                1305

Asn Lys Ala Pro Glu Ser Glu Leu Glu Met Glu Phe Glu Asp
    1310                1315                1320

Met Glu Asn Val Pro Leu Asp Arg Ser Ser His Cys Gln Arg Glu
    1325                1330                1335

Glu Ala Gly Gly Arg Asp Gly Gly Ser Ser Leu Gly Phe Lys Arg
    1340                1345                1350

Ser Tyr Glu Glu His Ile Pro Tyr Thr His Met Asn Gly Gly Lys
    1355                1360                1365

Lys Asn Gly Arg Ile Leu Thr Leu Pro Arg Ser Asn Pro Ser
    1370                1375                1380

<210> SEQ ID NO 34
<211> LENGTH: 477
<212> TYPE: DNA
<213> ORGANISM: Homo sapiens

<400> SEQUENCE: 34

```
ggctgaagct gccctcgagg acctggtctc caccattcga gtctgaagat tctcagaagc      60
acaaccagag tgagtatgag gattcggccg gcgaatgctg ctcctgtcca aagacagact     120
ctcagatcct gaaggagctg gaggagtcct cgtttaggaa gacgtttgag gattacctgc    180
acaacgtggt tttcgtcccc aggccatctc ggaaacgcag gtcccttggc gatgttggga    240
atgtgacggt ggccgtgccc acggtggcag ctttcccca  cacttcctcg accagcgtgc    300
ccacgagtcc ggaggagcac aggccttttg agaaggtggt gaacaaggag tcgctggtca    360
tctccggctt gcgacacttc acgggctatc gcatcgagct gcaggcttgc aaccaggaca    420
cccctgagga acggtgcagt gtggcagcct acgtcagtgc gaggaccatg cctgaag       477
```

<210> SEQ ID NO 35
<211> LENGTH: 513
<212> TYPE: DNA
<213> ORGANISM: Homo sapiens

<400> SEQUENCE: 35

```
ggctgaagct gccctcgagg acctggtctc caccattcga gtctgaagat tctcagaagc      60
acaaccagag tgagtatgag gattcggccg gcgaatgctg ctcctgtcca aagacagact     120
ctcagatcct gaaggagctg gaggagtcct cgtttaggaa gacgtttgag gattacctgc    180
acaacgtggt tttcgtcccc agaaaaacct cttcaggcac tggtgccgag gaccctaggc    240
catctcggaa acgcaggtcc cttggcgatg ttgggaatgt gacggtggcc gtgcccacgg    300
tggcagcttt ccccaacact tcctcgacca gcgtgcccac gagtccggag gagcacaggc    360
cttttgagaa ggtggtgaac aaggagtcgc tggtcatctc cggcttgcga cacttcacgg    420
gctatcgcat cgagctgcag gcttgcaacc aggacacccc tgaggaacgg tgcagtgtgg    480
cagcctacgt cagtgcgagg accatgcctg aag                                  513
```

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39

<400> SEQUENCE: 39

000

<210> SEQ ID NO 40

<400> SEQUENCE: 40

000

<210> SEQ ID NO 41

<400> SEQUENCE: 41

000

<210> SEQ ID NO 42

<400> SEQUENCE: 42

000

<210> SEQ ID NO 43

<400> SEQUENCE: 43

000

<210> SEQ ID NO 44
<211> LENGTH: 119
<212> TYPE: PRT
<213> ORGANISM: Homo sapiens

<400> SEQUENCE: 44

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Tyr Tyr Tyr Gly Met Asp Val Trp Gly Gln Gly Thr
            100                 105                 110

Thr Val Thr Val Ser Ser Ala
        115
```

<210> SEQ ID NO 45
<211> LENGTH: 121
<212> TYPE: PRT
<213> ORGANISM: Homo sapiens

<400> SEQUENCE: 45

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Tyr Tyr Tyr Tyr Gly Met Asp Val Trp Gly Gln
            100                 105                 110
```

```
Gly Thr Thr Val Thr Val Ser Ser Ala
        115                 120

<210> SEQ ID NO 46
<211> LENGTH: 118
<212> TYPE: PRT
<213> ORGANISM: Homo sapiens

<400> SEQUENCE: 46

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ser Ser Trp Tyr Phe Asp Leu Trp Gly Arg Gly Thr Leu
            100                 105                 110

Val Thr Val Ser Ser Ala
        115

<210> SEQ ID NO 47
<211> LENGTH: 124
<212> TYPE: PRT
<213> ORGANISM: Homo sapiens

<400> SEQUENCE: 47

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Arg Ser Ser
            20                  25                  30

Ser Tyr Tyr Trp Gly Trp Ile Arg Gln Pro Pro Gly Lys Gly Leu Glu
        35                  40                  45

Trp Ile Gly Gly Ile Tyr Tyr Ser Gly Ser Thr Tyr Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Arg Gly His Ser Ser Gly Trp Trp Tyr Phe Asp Leu
            100                 105                 110

Trp Gly Arg Gly Thr Leu Val Thr Val Ser Ser Ala
        115                 120

<210> SEQ ID NO 48
<211> LENGTH: 124
<212> TYPE: PRT
<213> ORGANISM: Homo sapiens

<400> SEQUENCE: 48

Gln Leu Gln Leu Gln Glu Ser Gly Pro Gly Leu Val Lys Pro Ser Glu
1               5                   10                  15
```

```
Thr Leu Ser Leu Thr Cys Thr Val Ser Gly Gly Ser Ile Asn Ser Ser
            20                  25                  30

Ser Asn Tyr Trp Gly Trp Ile Arg Gln Pro Pro Gly Lys Gly Leu Ala
        35                  40                  45

Trp Ile Gly Gly Ile Tyr Tyr Ser Gly Ser Thr Tyr Tyr Asn Pro Ser
    50                  55                  60

Leu Arg Ser Arg Val Thr Met Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Arg Gly His Ser Ser Gly Trp Trp Tyr Phe Asp Leu
            100                 105                 110

Trp Gly Arg Gly Thr Leu Val Thr Val Ser Ser Ala
        115                 120
```

<210> SEQ ID NO 49
<211> LENGTH: 117
<212> TYPE: PRT
<213> ORGANISM: Homo sapiens

<400> SEQUENCE: 49

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ile Thr Gly Thr Gly Met Asp Val Trp Gly Gln Gly Thr Thr Val
            100                 105                 110

Thr Val Ser Ser Ala
        115
```

<210> SEQ ID NO 50
<211> LENGTH: 120
<212> TYPE: PRT
<213> ORGANISM: Homo sapiens

<400> SEQUENCE: 50

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Arg Gly Leu Glu Trp Ile
        35                  40                  45

Gly Tyr Phe Phe Tyr Ser Gly Tyr Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Cys Ile Thr Gly Thr Thr Lys Gly Gly Met Asp Val Trp Gly Gln Gly
            100                 105                 110

Ala Thr Val Thr Val Ser Ser Ala
        115                 120

<210> SEQ ID NO 51
<211> LENGTH: 120
<212> TYPE: PRT
<213> ORGANISM: Homo sapiens

<400> SEQUENCE: 51

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Phe Phe Tyr Ser Gly Tyr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Cys Ile Thr Gly Thr Thr Lys Gly Gly Met Asp Val Trp Gly Gln Gly
            100                 105                 110

Thr Thr Val Thr Val Ser Ser Ala
        115                 120

<210> SEQ ID NO 52
<211> LENGTH: 110
<212> TYPE: PRT
<213> ORGANISM: Homo sapiens

<400> SEQUENCE: 52

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Gly Asn Asn
            20                  25                  30

Tyr Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Ala Val Phe Gly Gly Gly Thr Lys Leu Thr Val Leu Gly
            100                 105                 110

<210> SEQ ID NO 53
<211> LENGTH: 112
<212> TYPE: PRT
<213> ORGANISM: Homo sapiens

<400> SEQUENCE: 53

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asn Ile Glu Asn Asn
```

```
                20                  25                  30

His Val Ser Trp Tyr Gln Gln Leu Pro Gly Thr Ala Pro Lys Leu Leu
        35                  40                  45

Ile Tyr Asp Asn Asn Lys Arg Pro Ser Gly Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Glu Thr Trp Asp Thr Ser Leu
                85                  90                  95

Ser Ala Gly Arg Val Phe Gly Gly Gly Thr Lys Leu Thr Val Leu Gly
            100                 105                 110

<210> SEQ ID NO 54
<211> LENGTH: 108
<212> TYPE: PRT
<213> ORGANISM: Homo sapiens

<400> SEQUENCE: 54

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys Arg
            100                 105

<210> SEQ ID NO 55
<211> LENGTH: 108
<212> TYPE: PRT
<213> ORGANISM: Homo sapiens

<400> SEQUENCE: 55

Asp Ile Gln Met Thr Gln Ser Pro Ser Ser Val Ser Ala Ser Val Gly
1               5                   10                  15

Asp Ser Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Asn Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Phe
                85                  90                  95

Thr Phe Gly Pro Gly Thr Lys Val Asp Ile Lys Arg
            100                 105

<210> SEQ ID NO 56
<211> LENGTH: 108
<212> TYPE: PRT
```

<213> ORGANISM: Homo sapiens

<400> SEQUENCE: 56

Asp Ile Gln Met Thr Gln Ser Pro Ser Ser Val Ser Ala Ser Val Gly
1               5                   10                  15

Asp Arg Val Thr Ile Thr Cys Arg Ala Ser Arg Gly Ile Ser Ser Trp
            20                  25                  30

Leu Ala Trp Tyr Gln Gln Arg Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys Arg
            100                 105

<210> SEQ ID NO 57
<211> LENGTH: 112
<212> TYPE: PRT
<213> ORGANISM: Homo sapiens

<400> SEQUENCE: 57

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Ser Val Phe Gly Gly Gly Thr Lys Leu Thr Val Leu Gly
            100                 105                 110

<210> SEQ ID NO 58
<211> LENGTH: 112
<212> TYPE: PRT
<213> ORGANISM: Homo sapiens

<400> SEQUENCE: 58

Gln Ser Val Leu Thr Gln Ala Pro Ser Val Ser Gly Ala Pro Gly Gln
1               5                   10                  15

Arg Val Thr Ile Ser Cys Thr Gly Arg Ser Ser Asn Ile Gly Ala Gly
            20                  25                  30

Tyr Asp Val His Trp Tyr Gln Gln Phe Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

```
Leu Ser Gly Ser Val Phe Gly Gly Thr Lys Leu Thr Val Leu Gly
            100                 105                 110
```

```
<210> SEQ ID NO 59
<211> LENGTH: 112
<212> TYPE: PRT
<213> ORGANISM: Homo sapiens

<400> SEQUENCE: 59

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Asp Asp Glu Ala Asp Tyr Tyr Cys Gln Ser Phe Asp Ser Ser
                85                  90                  95

Leu Ser Gly Ser Val Phe Gly Gly Gly Thr Lys Leu Thr Val Leu Gly
            100                 105                 110
```

US 9,150,927 B2

QUANTIFICATION OF IR-A AND IR-B FOR TUMOR CLASSIFICATION

CROSS-REFERENCE TO RELATED APPLICATIONS

This application is a U.S. National Stage application of International Application No. PCT/US2010/052173, filed on Oct. 11, 2010, said International Application No. PCT/US2010/052173 claims benefit under 35 U.S.C. §119(e) of the U.S. Provisional Application No. 61/250,780, filed Oct. 12, 2009. Each of the above listed applications is incorporated by reference herein in its entirety for all purposes.

SEQUENCE LISTING

This application contains a Sequence Listing which has been submitted in ASCII format via EFS-Web and is incorporated by reference in its entirety. Said ASCII copy, created on Jun. 27, 2013, is named IGF-400US1_SL.txt and is 49,396 bytes in size.

BACKGROUND

1. Field of the Disclosure

Without limitation, this disclosure relates to compositions and methods for detecting and quantifying the expression of insulin receptor isoform A (IR-A) and/or insulin receptor isoform B (IR-B) in a sample, such as a tissue sample. The disclosure also relates to methods of diagnosis and classification based at least in part upon detecting and quantifying the expression of insulin receptor isoform A (IR-A) and/or insulin receptor isoform B (IR-B) in a sample, such as a tissue sample. Methods of treating a subject based upon such a classification are among additional aspects of the disclosure presented herein.

2. Description of the Related Art

The insulin receptor (INSR) is a transmembrane tyrosine kinase receptor implicated in regulation of energy metabolism. The INSR comprises two subunits, α and β, expressed from a single INSR gene. Two isoforms, designated IR-A and IR-B, are the result of alternative mRNA splicing. IR-A is generated by an alternative splicing of the mRNA transcribed from the INSR gene to omit exon 11, which is included in mRNA of IR-B. (FIGS. 1A-1B). Thus, IR-A differs from IR-B because it lacks a stretch of amino acid residues at the carboxy terminus of the INSR α-subunit. IR-A and IR-B are more than 99% identical (FIG. 2). While the expression profiles of the two isoforms are different, the isoforms are coexpressed in cells. The relative abundance of IR-A and IR-B is regulated by development stage- and tissue-specific factors.

For example, IR-A is predominantly expressed in fetal and cancer cells, whereas IR-B is predominantly expressed in differentiated insulin target cells. IR-A exhibits high affinity for insulin, intermediate affinity for IGF-II, and low affinity for IGF-I. IGF-II binds to IGF type I receptor (IGF-IR) and to IR-A with similar affinities. IR-B is a highly specific receptor for insulin.

Currently methods of determining IR-A and IR-B levels in a patient sample are hampered by the lack of an efficient and accurate means of detection. To date, the only available method to specifically measure IR-A expression has been described by Sciacca, et al (Oncogene 21(54):8240-50; 2002 Nov. 28). This method is based on PCR and gel separation, followed by qualitative measurement of the resulting bands. This method is very labor intensive and is not quantitatively accurate, which limits its use in a high throughput or clinical setting.

SUMMARY

There is a need for improved diagnostic tests that can predict a patients' response to a drug based on a determination of whether the patient's tissues express a molecular target of the drug. There is need for a method to accurately detect and/or quantify the expression of IR-A and IR-B. The ability to be able to detect and quantify the expression of each isoform in a patient sample is useful to provide a patient with a personalized treatment regime. Such personalized treatment regimes offer the potential to maximize therapeutic benefit to the patient, while minimizing, for example, side effects that may be associated with alternative and less effective treatment regimes.

Disclosed herein are compositions and methods that are useful for detecting and/or quantifying whether a sample of biological material contains cells that express IR-A and/or IR-B, including human IR-A and/or IR-B, and kits for use in such a method. The methods are based, in part, on the finding that particular oligonucleotides can be used to measure the expression of IR-A and/or IR-B in tissue samples. These oligonucleotides can be used to quickly and quantitatively distinguish the level of IR-A and/or IR-B expression in a sample such that the methods can be used in high throughput and clinical settings. These compositions and methods can be useful in methods to classify tissue samples, for example tumor tissue samples. The results of such methods may be used as a factor in classifying a tumor or cancer patient as an indicator of how a patient will respond to drugs such as antagonists or agonists of INSR, IGF1R, or IGF. These methods and the resulting classifications can be used in methods of selecting candidates for treatment and methods of treating cancer patients.

Useful oligonucleotides can comprise synthetic nucleic acids that can be used to selectively amplify IR-A and/or IR-B. Such useful oligonucleotides can comprise a synthetic nucleic acid sequence comprising 10-30 consecutive nucleotides, wherein the synthetic nucleic acid sequence comprises at least 10-20 consecutive nucleotides of any one of the following sequences: (i) SEQ ID NO: 3, a sequence complementary thereto, or a sequence that is capable of hybridizing to SEQ ID NO:3, or its complement, under stringent conditions; (ii) SEQ ID NO: 4, a sequence complementary thereto (SEQ ID NO:21), or a sequence that is capable of hybridizing to SEQ ID NO:4, or its complement, under stringent conditions, or a variant thereof; (iii) SEQ ID NO: 5, a sequence complementary thereto, or a sequence that is capable of hybridizing to SEQ ID NO:5, or its complement, under stringent conditions; or (iv) SEQ ID NO: 6, a sequence complementary thereto (SEQ ID NO:22), or a sequence that is capable of hybridizing to SEQ ID NO:6, or its complement, under stringent conditions is disclosed. The synthetic nucleic acid sequence may consist essentially of any one of the following nucleic acid sequences: (i) SEQ ID NO: 3 (TGAGGATTACCTGCACAACG), a sequence complementary thereto, or a sequence that is capable of hybridizing to SEQ ID NO:3, or its complement, under stringent conditions, or a variant thereof; (ii) SEQ ID NO: 4 (GATGTTGGGA ATGT-GACGGT), a sequence complementary thereto (SEQ ID NO:21), or a sequence that is capable of hybridizing to SEQ ID NO:4, or its complement, under stringent conditions; (iii) SEQ ID NO: 5 (TTGAGGATTACCTGCACAACGT), a sequence complementary thereto, or a sequence that is capable of hybridizing to SEQ ID NO:5, or its complement, under stringent conditions, or a variant thereof; or (iv) SEQ ID NO: 6 (AAACGCAGGTCCCTTGGC), a sequence complementary thereto (SEQ ID NO:22), or a sequence that is capable of hybridizing to SEQ ID NO:6, or its complement, under stringent conditions, or a variant thereof.

A useful synthetic nucleic acid sequence may SEQ ID NO: 7, a sequence complementary thereto, or a sequence that is capable of hybridizing to SEQ ID NO:7, or its complement, under stringent conditions, or a variant thereof or SEQ ID NO: 8, a sequence complementary thereto, or a sequence that is capable of hybridizing to SEQ ID NO:8, or its complement, under stringent conditions, or a variant thereof. Another useful synthetic nucleic acid sequence may consist essentially of SEQ ID NO: 7, a sequence complementary thereto, or a sequence that is capable of hybridizing to SEQ ID NO:7, or its complement, under stringent conditions or a variant thereof, or SEQ ID NO: 8, a sequence complementary thereto, or a sequence that is capable of hybridizing to SEQ ID NO:8, or its complement, under stringent conditions or a variant thereof. A composition comprising any of the synthetic nucleic acid sequences described above can also be useful.

Also disclosed herein is a primer set that is useful for determining the presence or absence of a target human IR-A nucleic acid sequence in a biological sample, wherein the primer set comprises at least one synthetic nucleic acid sequence that may be chosen from among a synthetic nucleic acid sequence comprising 10-30 consecutive nucleotides of at least one of the following: (a) the last 50 bases of exon 10 of the INSR gene (SEQ ID NO: 1) or a complementary nucleic acid sequence thereof; and (b) the first 60 bases of exon 12 of the INSR gene (SEQ ID NO: 2), a sequence complementary thereto, or a sequence that is capable of hybridizing to SEQ ID NO:8, or its complement, under stringent conditions. The synthetic nucleic acid sequence may have a nucleotide sequence that may be chosen from among SEQ ID NO: 3, a sequence complementary thereto, or a sequence that is capable of hybridizing to SEQ ID NO:3, or its complement, under stringent conditions; SEQ ID NO: 4, a sequence complementary thereto (SEQ ID NO:21), or a sequence that is capable of hybridizing to SEQ ID NO:4, or its complement, under stringent conditions; SEQ ID NO: 5, a sequence complementary thereto, or a sequence that is capable of hybridizing to SEQ ID NO:5, or its complement, under stringent conditions; and SEQ ID NO: 6, a sequence complementary thereto (SEQ ID NO:22), or a sequence that is capable of hybridizing to SEQ ID NO:6, or its complement, under stringent conditions.

Also disclosed herein is a method for determining the presence or absence of a target IR-A nucleic acid sequence in a biological sample, comprising the steps of: (a) contacting a biological sample with a primer set such as described above under conditions suitable for polymerase-based amplification; and (b) detecting and/or quantifying amplified target IR-A nucleic acid sequence. As examples, a biological sample can be a tissue sample such as a tumor sample or a sample comprising nucleic acids derived from a tissue or cell sample.

A primer set can include SEQ ID NO: 3, a sequence complementary thereto, or a sequence that is capable of hybridizing to SEQ ID NO:3, or its complement, under stringent conditions, and SEQ ID NO: 4, a sequence complementary thereto (SEQ ID NO:21), or a sequence that is capable of hybridizing to SEQ ID NO:4, or its complement, under stringent conditions. In another example, the primer set can include SEQ ID NO: 5, a sequence complementary thereto, or a sequence that is capable of hybridizing to SEQ ID NO:5, or its complement, under stringent conditions, and SEQ ID NO: 6, a sequence complementary thereto (SEQ ID NO:22), or a sequence that is capable of hybridizing to SEQ ID NO:6, or its complement, under stringent conditions. In one example, the polymerase-based amplification is quantitative polymerase chain reaction (q-PCR).

A primer and probe set can include: SEQ ID NO: 3, a sequence complementary thereto, or a sequence that is capable of hybridizing to SEQ ID NO:3, or its complement, under stringent conditions, or a variant thereof; SEQ ID NO: 4 (SEQ ID NO:21), a sequence complementary thereto, or a sequence that is capable of hybridizing to SEQ ID NO:4, or its complement, under stringent conditions, or a variant thereof; and SEQ ID NO: 7, a sequence complementary thereto, or a sequence that is capable of hybridizing to SEQ ID NO:7, or its complement, under stringent conditions, or a variant thereof, wherein said sequence may also comprise a detectable label and may further comprise a quencher. In another example, a primer and probe set can include: SEQ ID NO: 5, a sequence complementary thereto, or a sequence that is capable of hybridizing to SEQ ID NO:5, or its complement, under stringent conditions, or a variant thereof; SEQ ID NO: 6, a sequence complementary thereto (SEQ ID NO:22), or a sequence that is capable of hybridizing to SEQ ID NO:6, or its complement, under stringent conditions, or a variant thereof; and SEQ ID NO: 8, a sequence complementary thereto, or a sequence that is capable of hybridizing to SEQ ID NO:8, or its complement, under stringent conditions, or a variant thereof, wherein said sequence may also include a detectable label and may further include a quencher. Typically, the amplified product is less than 100 bases.

A useful synthetic nucleic acid sequence can comprise 10-30 consecutive nucleotides, wherein the synthetic nucleic acid sequence comprises at least 10-20 consecutive nucleotides of any one of the following sequences: SEQ ID NO: 11, a sequence complementary thereto, or a sequence that is capable of hybridizing to SEQ ID NO:11, or its complement, under stringent conditions, or a variant thereof; or SEQ ID NO: 12, a sequence complementary thereto, or a sequence that is capable of hybridizing to SEQ ID NO:12, or its complement, under stringent conditions, or a variant thereof. In one example, the nucleic acid sequence consists essentially of: SEQ ID NO: 11, a sequence complementary thereto, or a sequence that is capable of hybridizing to SEQ ID NO:11, or its complement, under stringent conditions, or a variant thereof; or SEQ ID NO: 12, a sequence complementary thereto, or a sequence that is capable of hybridizing to SEQ ID NO:12, or its complement, under stringent conditions, or a variant thereof; SEQ ID NO: 13, a sequence complementary thereto, or a sequence that is capable of hybridizing to SEQ ID NO:13, or its complement, under stringent conditions, or a variant thereof; SEQ ID NO: 14, a sequence complementary thereto, or a sequence that is capable of hybridizing to SEQ ID NO:14, or its complement, under stringent conditions, or a variant thereof or SEQ ID NO: 15, a sequence complementary thereto, or a sequence that is capable of hybridizing to SEQ ID NO:15, or its complement, under stringent conditions, or a variant thereof. A composition comprising any one or more of the synthetic nucleic acid sequences above may also be useful.

A primer set for determining the presence or absence of IR-B in a biological sample can comprise a synthetic nucleic acid sequence comprising 10-30 consecutive nucleotides of at least one of the following: (a) the last 50 bases of exon 10 (SEQ ID NO: 1) of the INSR gene, a sequence complementary thereto, or a sequence that is capable of hybridizing to SEQ ID NO:1, or its complement, under stringent conditions, and the bases of exon 11 (SEQ ID NO: 9) of the INSR gene, a sequence complementary thereto, or a sequence that is capable of hybridizing to SEQ ID NO:9, or its complement, under stringent conditions or a sequence complementary thereto, or which bridges exon 10 and exon 11 of the INSR gene, a sequence complementary thereto, or a sequence that is capable of hybridizing thereto, or its complement, under stringent conditions; and (b) the first 50 bases of exon 12 of the INSR gene (SEQ ID NO: 10), a sequence complementary thereto, or a sequence that is capable of hybridizing to SEQ ID NO:10, or its complement, under stringent conditions or a sequence complementary thereto. A primer set can include at least one synthetic nucleic acid sequence has a nucleotide sequence that may be chosen from among SEQ ID NO: 11, a sequence complementary thereto, or a sequence that is capable of hybridizing to SEQ ID NO:11, or its complement, under stringent conditions; and SEQ ID NO: 12, a sequence complementary thereto, or a sequence that is capable of hybridizing to SEQ ID NO:12, or its complement, under stringent conditions.

A method for determining the presence or absence of a target IR-B nucleic acid sequence in a biological sample may comprise the steps of: (c) contacting a biological sample with the primer set of above under conditions suitable for polymerase-based amplification; and (d) detecting and/or quantifying amplified target IR-B nucleic acid sequence. As an example, the biological sample may be a sample comprising nucleic acid from a tissue sample such as a tumor sample. In another example, the polymerase-based amplification may be by a quantitative polymerase chain reaction. A primer and probe set may include: SEQ ID NO: 11, a sequence complementary thereto, or a sequence that is capable of hybridizing to SEQ ID NO:11, or its complement, under stringent conditions; SEQ ID NO: 12, a sequence complementary thereto, or a sequence that is capable of hybridizing to SEQ ID NO:12, or its complement, under stringent conditions; and SEQ ID NO: 13, a sequence complementary thereto, or a sequence that is capable of hybridizing to SEQ ID NO:13, or its complement, under stringent conditions which may also include a detectable label and may further include a quencher. In another example, a primer and probe set may include: SEQ ID NO: 11, a sequence complementary thereto, or a sequence that is capable of hybridizing to SEQ ID NO:11, or its complement, under stringent conditions; SEQ ID NO: 12, a sequence complementary thereto, or a sequence that is capable of hybridizing to SEQ ID NO:12, or its complement, under stringent conditions; and SEQ ID NO: 14, a sequence complementary thereto, or a sequence that is capable of hybridizing to SEQ ID NO:14, or its complement, under stringent conditions.

In another example, a primer set can include: SEQ ID NO: 11, a sequence complementary thereto, or a sequence that is capable of hybridizing to SEQ ID NO:11, or its complement, under stringent conditions; SEQ ID NO: 12, a sequence complementary thereto, or a sequence that is capable of hybridizing to SEQ ID NO:12, or its complement, under stringent conditions; and further comprise SEQ ID NO: 15, a sequence complementary thereto, or a sequence that is capable of hybridizing to SEQ ID NO:15, or its complement, under stringent conditions which may also include a detectable label and may further include a quencher. Typically the amplified product is less than 100 bases.

A method for determining the presence or absence of a target IR-A and IR-B nucleic acid in a biological sample may comprise the steps of: contacting a biological sample with an IR-A primer set as described above under conditions suitable for polymerase-based amplification; contacting a biological sample with an IR-B primer set as described above under conditions suitable for amplification by polymerase reaction; and detecting and/or quantifying amplified target IR-A and IR-B nucleic acid sequence. The method may further comprise calculating a relative expression level of IR-A and IR-B.

A kit for determining the presence or absence of IR-A in a biological sample may comprise at least one synthetic nucleic acid sequence described above and instructions for carrying out one or more of the methods described herein. In such a kit, the at least one synthetic nucleic acid sequence may have a nucleotide sequence chosen from among the IR-A primers and probes disclosed herein, or any sets thereof. A kit can also include suitable PCR reagents; and optionally, a positive and/or negative control for determining the presence or absence of IR-A.

A kit for determining the presence or absence of IR-B in a biological sample can comprise at least one synthetic nucleic acid as described above and instructions for performing one or more methods described herein. A synthetic nucleic acid in such a kit may have a nucleotide sequence chosen from among the IR-B nucleic acids. The kit may also include suitable PCR reagents; and optionally, a positive and/or negative control for determining the presence or absence of IR-B.

A method for selecting a patient responsive to an IGFI/II ligand, INSR, or IGFR1 receptor antagonist or agonist can comprise obtaining a biological sample from a subject having or suspected of having cancer; and detecting and/or quantifying the presence of IR-A in the sample. The presence or absence of IR-A is an indication as to whether an IGFI/II ligand, INSR, or IGFR1 receptor antagonist or agonists should be administered to the subject. Thus, a method of treating a patient may comprise detecting and/or quantifying the presence of IR-A in a patient that has been obtained from a patient and administering an IGFI/II ligand, INSR, or IGFR1 receptor antagonist or antagonist to the patient. As an example, the IGFI and II ligand, INSR, or IGFR1 receptor antagonist may be an antibody.

A tumor may be classified according to the expression of IR-A and or IR-B, or by the relative amounts of IR-A and IR-B. Classifying tumors in this way provides an ability to identify tumors that have overexpressed IR-A and/or IR-B or that have an altered amount of IR-A relative to IR-B or vice versa. A method of classifying a tumor can comprise quantifying the expression of IR-A and/or IR-B or the amount of IR-A relative to IR-B or vice versa in a sample of tumor tissue and assigning a classification based upon the quantification. A method of treating a patient having a tumor can comprise classifying the tumor by quantifying the expression of IR-A and/or IR-B or the amount of IR-A relative to IR-B or vice versa in a sample of tumor tissue; assigning a classification based upon that quantification of the expression of IR-A and/or IR-B or the amount of IR-A relative to IR-B or vice versa; and administering an IGFI/II ligand or IGFR1 receptor antagonist or agonist to the patient in accordance with the classification.

BRIEF DESCRIPTION OF THE DRAWINGS

FIG. 1A shows the genomic structure of IR-A and IR-B. FIG. 1B presents a schematic of the α and β subunits of an INSR homodimer with exon locations illustrated on the left and functional domain locations illustrated on the right.

FIG. 2 shows a sequence alignment of human IR-A (SEQ ID NO: 32) and IR-B (SEQ ID NO: 33) demonstrating that the sequences are identical except for the omission of exon 11 from IR-A.

FIG. 4 shows a nucleotide sequence encoding a portion of IR-A (SEQ ID NO: 34) and a schematic of primer and probe locations for an example 1R-A assay.

FIG. 5 shows a nucleotide sequence encoding a portion of IR-A (SEQ ID NO: 34) and a schematic of primer and probe locations for an example 1R-A assay.

FIG. 6 shows a nucleotide sequence encoding a portion of IR-B (SEQ ID NO: 35) and a schematic of primer and probe locations for an example 1R-B assay.

FIGS. 13 (A and B) show IR-A:IR-B ΔCt differential in subtypes of ER+breast cancer. Scatter plot representation of calculated IR-A:IR-B ΔCt differentials with regard to sample subtype (normal, luminal-A, or luminal-B) classification determined by a shrunken centroid classifier-based methodology (A) and a two-sample Welch's t-test analysis (B). All subtype pair-wise comparisons display a significant difference (two-sample t-test, p<0.001). Bars represent the median IR-A:IR-B ΔCt differential within a particular sample subtype.

DETAILED DESCRIPTION

Figures 1A, 1B:
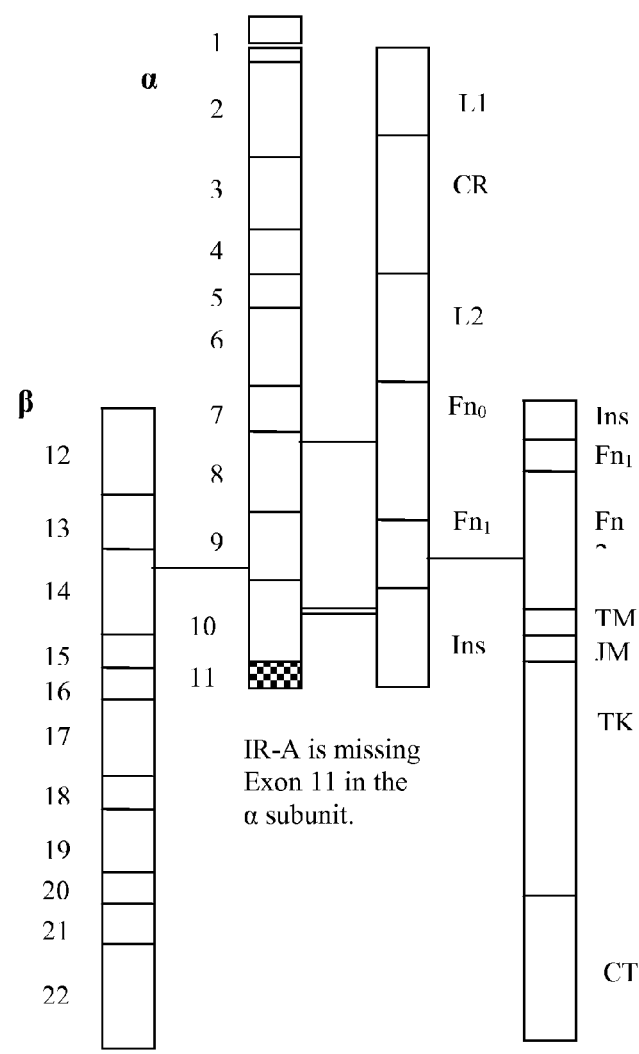
FIGS. 1A-1B illustrate IR-A and IR-B.

The following primer and probe sequences are referred to herein.

```
                                              SEQ ID NO: 1
(TTTAGGAAGA CGTTTGAGGA TTACCTGCAC AACGTGGTTT

TCGTCCCCAG) INSR Exon 10 C-term

SEQ ID NO: 2
(GCCATCTCGG AAACGCAGGT CCCTTGGCGA TGTTGGGAAT

GTGACGGTGG CCGTGCCCAC) INSR Exon 12 N-term

SEQ ID NO: 3
(TGAGGATTACCTGCACAACG) IR-A Primer

SEQ ID NO: 4
(GATGTTGGGA ATGTGACGGT) IR-A Primer (reverse complement SEQ ID NO: 21)

SEQ ID NO: 5
(TTGAGGATTA CCTGCACAACGT) IR-A Primer

SEQ ID NO: 6
(AAACGCAGGTCCCTTGGC) IR-A Primer (reverse complement SEQ ID NO: 22)

SEQ ID NO: 7
(TCCCCAGGCCATCT) IR-A Probe

SEQ ID NO: 8
(TTTTCGTCCCCAGGCCA) IR-A Probe

SEQ ID NO: 9
(AAAAACCTCT TCAGGCACTG GTGCCCAGGA CCCTAG) INSR

Exon 11

SEQ ID NO: 10
(GCCATCTCGG AAACGCAGGT CCCTTGGCGA TGTTGGGAAT

GTGACGGTGG) INSR Exon 12 N-term
```

-continued (CGTCCCCAGAAAAACCTCTTC) IR-B Primer
SEQ ID NO: 11

(GGACCTGCGTTTCCGAGAT) IR-B Primer
SEQ ID NO: 12

(ACTGGTGCCGAGGAC) IR-B Specific Probe
SEQ ID NO: 13

(CCGAGGACCCTAGGC) IR-B Specific Probe
SEQ ID NO: 14

(TGCCGAGGACCCTAG) IR-B Specific Probe
SEQ ID NO: 15

Further primer and probe sequences include those in Tables 3 and 4. The skilled artisan will be able to select primers pairs from the primers disclosed herein, that are capable of amplifying nucleic acid sequences in a PCR reaction (e.g., anneal to opposite strands and prime DNA synthesis in the proper direction). The skilled artisan will understand that the complement of such primers can be used, for example, as negative controls.

These nucleic acid sequences and related sequences described herein can be used in assays to detect and quantify expression of human IR-A and human IR-B in a sample despite the high sequence identity between IR-A and IR-B. Thus, for the first time a quick and sensitive method to determine expression of IR-A and/or IR-B in sample has been discovered. The methods described using these sequences are quantitatively accurate, allowing them to be used in high throughput and clinical settings.

A synthetic nucleic acid sequence or oligonucleotide that can be used to identify the expression of IR-A and/or IR-B in a test sample may be DNA, RNA, chimeric mixtures or derivatives or modified versions thereof that can be modified at the base moiety, sugar moiety or backbone and may include other appending groups, labels or quenchers, so long as they are still capable of functioning in the desired reaction. The synthetic nucleic acid sequences may comprise at least one modified phosphate backbone—such as phosphorothioate, a phosphorodithioate, a phosphoramidothioate, a phosphoramidate, a phosphordiamidate, a methylphosphonate, an alkyl phosphotriester, and a formacetal or an analogue thereof.

A. IR-A Nucleic Acid Sequences

Suitable IR-A synthetic nucleic acid sequences include those appearing in Tables 3 and 4.

Synthetic nucleic acids comprising IR-A nucleic acid sequences that occur in the last 50, 45, 40, 35, 30, 25 or 20 bases of exon 10 of the INSR gene (SEQ ID NO: 1) or a sequence that is capable of hybridizing to SEQ ID NO:1, or its complement, under stringent conditions, and the first 60, 55, 50, 45, 40, 35, 30, 25 or 20 bases of exon 12 of the INSR gene (SEQ ID NO: 2) or a sequence that is capable of hybridizing to SEQ ID NO:2, or its complement, under stringent conditions can be used in polymerase-based amplification and detection such as quantitative polymerase chain reaction (qPCR) (also known as real-time PCR or kinetic PCR) to determine the level of expression of IR-A in a sample.

A synthetic nucleic acid comprising an IR-A sequence can include 10, 11, 12, 13, 14, 15, 16, 17, 18, 19, 20, 21, 22, 23, 24, 25, 26, 27, 28, 29 or 30 consecutive nucleotides, wherein the synthetic nucleic acid sequence comprises at least 10, 11, 12, 13, 14, 15, 16, 17, 18, 19, 20, consecutive nucleotides of any one of the following sequences:
(i) SEQ ID NO: 3 (TGAGGATTAC CTGCACAACG), a sequence complementary thereto, or a sequence that is capable of hybridizing to SEQ ID NO:3, or its complement, under stringent conditions;
(ii) SEQ ID NO: 4 (GATGTTGGGA ATGTGACGGT), a sequence complementary thereto (SEQ ID NO:21), or a sequence that is capable of hybridizing to SEQ ID NO:4, or its complement, under stringent conditions;
(iii) SEQ ID NO: 5 (TTGAGGATTA CCTGCACAAC GT), a sequence complementary thereto, or a sequence that is capable of hybridizing to SEQ ID NO:5, or its complement, under stringent conditions; or
(iv) SEQ ID NO: 6 (AAACGCAGGT CCCTTGGC), a sequence complementary thereto (SEQ ID NO:22), or a sequence that is capable of hybridizing to SEQ ID NO:6, or its complement, under stringent conditions.

In one example, a primer set for determining the presence or absence of a target IR-A nucleic acid sequence in a biological sample can comprise at least one synthetic nucleic acid sequence that may be chosen from among a synthetic nucleic acid sequence comprising 10-30 consecutive nucleotides of at least one of the following: (a) the last 50, 45, 40, 35, 30, 25 or 20 bases of exon 10 of the INSR gene (SEQ ID NO: 1), a sequence complementary thereto, or a sequence that is capable of hybridizing to SEQ ID NO:1, or its complement, under stringent conditions; and (b) the first 60, 55, 50, 45, 40, 35, 30, 25 or 20 bases of exon 12 of the INSR gene (SEQ ID NO: 2), a sequence complementary thereto, or a sequence that is capable of hybridizing to SEQ ID NO:2, or its complement, under stringent conditions. The primer set can include (i) SEQ ID NO: 3, a sequence complementary thereto, or a sequence that is capable of hybridizing to SEQ ID NO:3, or its complement, under stringent conditions and SEQ ID NO: 4, a sequence complementary thereto (SEQ ID NO:21), or a sequence that is capable of hybridizing to SEQ ID NO:4, or its complement, under stringent conditions or (ii) SEQ ID NO: 5, or complementary sequence thereof; and SEQ ID NO: 6, a sequence complementary thereto (SEQ ID NO:22), or a sequence that is capable of hybridizing to SEQ ID NO:6, or its complement, under stringent conditions. Typically the primer set is used in PCR to produce a product between about 50-150 bp. Probes may comprise SEQ ID NO: 7 or 8, or a sequence that is capable of hybridizing to either SEQ ID NO:7 or 8, or its complement, under stringent conditions, and may also comprise an appropriate label and quencher combination.

As an example, a primer set useful in a quantitative polymerase chain reaction (qPCR) includes:
SEQ ID NO: 3, or a nucleic acid sequence that is complementary thereto;
SEQ ID NO: 4, or a nucleic acid sequence that is complementary thereto (SEQ ID NO: 21); and an additional synthetic nucleic acid or probe having a detectable label that may also include a quencher. In one example, the additional nucleic acid is a single stranded nucleic acid sequence of between 10-50 nucleotides and is designed to bind specifically to the DNA sequence of an IR-A cDNA or its complement between the two PCR primers of SEQ ID NO: 3 and 4. The additional nucleic acid typically has a fluorescent reporter or fluorophore such as 6-carboxyfluorescein (FAM) or tetrachlorofluorescin (TET) and a quencher such as tetramethylrhodamine (TAMRA) covalently attached at its 5' and 3' ends. In this example, only specific PCR products generate a fluorescent signal. In this example, the additional nucleic acid can be 10-50 bases and include at least 5-14 bases of SEQ ID NO: 7 or a sequence that is capable of hybridizing to SEQ ID NO:7, or its complement, under stringent conditions.

In another example, the primer set comprises:

SEQ ID NO: 5, or a nucleic acid sequence that is complementary thereto;

SEQ ID NO: 6, or a nucleic acid sequence that is complementary thereto (SEQ ID NO: 22); and an additional nucleic acid having a detectable label that may also include a quencher. The additional nucleic acid can be a single stranded nucleic acid sequence of between 10-32 nucleotides and is designed to bind only the DNA sequence of an IR-A cDNA or its complement between the two PCR primers of SEQ ID NO: 5 and 6. In this example, the additional nucleic acid can be 10-32 bases and include at least 5-14 bases of SEQ ID NO: 8 or a sequence that is capable of hybridizing to SEQ ID NO:8, or its complement, under stringent conditions.

B. IR-B Nucleic Acid Sequences

Suitable IR-B synthetic nucleic acid sequences include those appearing in Tables 3 and 4.

IR-B nucleic acid sequences that occur in the (a) last 50, 45, 40, 35, 30, 25 or 20 bases of exon 10 (SEQ ID NO: 1) or its complement or a sequence that is capable of hybridizing to SEQ ID NO:1, or its complement, under stringent conditions and exon 11 of the INSR gene (SEQ ID NO: 9) or a sequence complementary thereto or a sequence that is capable of hybridizing to SEQ ID NO:9, or its complement, under stringent conditions, or a sequence bridging exons 10 and 11, or a sequence that is capable of hybridizing to the region bridging exons 10 and 11, or its complement, under stringent conditions; and (b) the first 50, 45, 40, 35, 30, 25 or 20 bases of exon 12 of the INSR gene (SEQ ID NO: 2), a sequence complementary thereto or a sequence that is capable of hybridizing to SEQ ID NO:3, or its complement, under stringent conditions can be used in the methods disclosed herein to determine the level of expression of IR-B, particularly PCR based methods.

In one example, synthetic nucleic acids comprising IR-B sequences can include 10, 11, 12, 13, 14, 15, 16, 17, 18, 19, 20, 21, 22, 23, 24, 25, 26, 27, 28, 29 or 30 consecutive nucleotides, wherein the synthetic nucleic acid sequence comprises at least 10, 11, 12, 13, 14, 15, 16, 17, 18, 19, 20, consecutive nucleotides of any one of the following sequences:

(i) SEQ ID NO: 11 or a sequence complementary thereto or a sequence that is capable of hybridizing to SEQ ID NO:11, or its complement, under stringent conditions; or (ii) SEQ ID NO: 12 or a sequence complementary thereto, or a sequence that is capable of hybridizing to SEQ ID NO:12, or its complement, under stringent conditions.

In another example, a primer set for determining the presence or absence of a target IR-B nucleic acid sequence in a biological sample may comprise at least one synthetic nucleic acid sequence that may be chosen from among a synthetic nucleic acid sequence comprising 10-27 consecutive nucleotides of at least one of the following: (a) 50, 45, 40, 35, 30, 25 or 20 bases in the last 50 bases of exon 10 (SEQ ID NO:1) and exon 11 of the INSR gene (SEQ ID NO: 9) or a sequence complementary thereto; and (b) the first 50, 45, 40, 35, 30, 25 or 20 bases of exon 12 of the INSR gene (SEQ ID NO: 10) or a sequence complementary thereto. The primer set can include a nucleotide sequence that may be chosen from among SEQ ID NO: 11, or a synthetic nucleic acid sequence complementary thereto; and SEQ ID NO: 12, or a synthetic nucleic acid sequence complementary thereto.

When the primer set is used in a PCR such as qPCR, the primer set can include SEQ ID NO: 11, or a synthetic nucleic acid sequence that is complementary thereto, or a sequence that is capable of hybridizing to SEQ ID NO:11, or its complement, under stringent conditions; SEQ ID NO: 12, or a synthetic nucleic acid sequence that is complementary thereto, or a sequence that is capable of hybridizing to SEQ ID NO:12, or its complement, under stringent conditions; and an additional nucleic acid comprising a detectable label that may also include a quencher. The additional nucleic acid can be a single stranded nucleic acid sequence of between 10-27 nucleotides and is designed to bind specifically to the sequence of an IR-B cDNA or its complement between the two PCR primers of SEQ ID NO: 11 and 12 or a sequence that is capable of hybridizing to that region, or its complement, under stringent conditions. As an example, the additional nucleic acid can be 10-27 bases and include at least 5-14 bases of SEQ ID NO: 13, or its complement, or a sequence that is capable of hybridizing to SEQ ID NO: 13, or its complement, under stringent conditions. The additional nucleic acid can be 10-30 bases and include at least 5-14 bases of SEQ ID NO: 14, or its complement, or a sequence that is capable of hybridizing to SEQ ID NO: 14, or its complement, under stringent conditions. In yet another example, the additional nucleic acid can be 10-30 bases and include at least 5-14 bases of SEQ ID NO: 15, or its complement, or a sequence that is capable of hybridizing to SEQ ID NO:15, or its complement, under stringent conditions. The additional nucleic acid typically has a fluorescent reporter or fluorophore such as 6-carboxyfluorescein (FAM) and tetrachlorofluorescin (TET) and a quencher such as tetramethylrhodamine (TAMRA) covalently attached at its 5' and 3' ends.

Useful synthetic nucleic acid sequences also include variants of the sequences disclosed above or sequences that are substantially similar to the nucleic acids disclosed herein. Variants include sequences that are altered by one or more bases, such as 2, 3, 4, 5, 6, 7, 8, 9 or 10 but can still anneal to the specific locations on the IR-A target sequence of interest. The term "substantially similar" when used in relation to annealing or hybridization, means that a synthetic nucleic acid sequence, such as a primer, should be sufficiently complementary to hybridize or anneal to its respective nucleic acid under stringent conditions. The synthetic nucleic acid sequence need not reflect the exact sequence of its respective nucleic acid, and can, in fact, be "degenerate." Non-complementary bases or other sequences may be interspersed into the synthetic nucleic acid sequence, provided that the synthetic nucleic acid sequence has sufficient complementarity with the sequence to permit hybridization. Thus, by way of example, the primers used for PCR amplification may be selected to be "substantially" complementary to the specific sequence to be amplified.

As used herein, the term "hybridization" refers to the process by which a strand of nucleic acid joins with a complementary strand through base pairing as well as the process of amplification as carried out in, for example, PCR technologies. Nucleotide sequences that are capable of hybridizing to the complement of a given nucleotide sequence are generally functionally equivalent and can be substituted for that nucleotide sequence for the purposes of the methods described herein.

Thus, while this disclosure identifies specific primers and probes that have been found to be particularly sensitive and specific, persons of skill in the art would understand that useful primers include any primers that can prime a polymerase reaction at about the same locations as the exemplary primers disclosed herein. That is, primers which prime a polymerization reaction in exon 10 and exon 12 of the INSR gene can be used to amplify a diagnostic sequence. Primers which span a the exon 10-exon 11 junction in the sequence of IR-B can be used to specifically amplify IR-B sequences. Similarly, additional probes which distinguish between IR-A and IR-B may be synthesized that specifically bind to amplified IR-A or IR-B target sequence. Generally, longer sequences comprising more complementary residues may contain greater variation.

"Stringent hybridization conditions" may be any of low stringency conditions, moderately stringent conditions and highly stringent conditions. Generally, "low stringency conditions" are, for example: hybridization in a solution comprising 5×SSC; 5× Denhart solution; 0.5% (w/v) SDS; and 50% (w/v) formamide; at 32° C. "Moderately stringent conditions" are, for example: hybridization in a solution comprising 5×SSC; SxDenhart solution; 0.5% (w/v) SDS; and 50% (w/v) formamide; at 42° C. "Highly stringent conditions" are, for example: hybridization in a solution comprising 5×SSC; SxDenhart solution; 0.5% (w/v) SDS; and 50% (w/v) formamide; at 50° C. Hybridization stringency is affected by a plurality of factors such as temperature, nucleic acid concentration, nucleic acid length, ion strength, time, and salt concentration. These are merely exemplary conditions that will produce the different levels of stringency. Those skilled in the art would be able to realize similar stringency by suitably adjusting hybridization conditions, including by adjusting such conditions for the desired stringency in a PCR reaction.

Synthetic nucleic acid sequences may be derived by cleavage of a larger nucleic acid fragment using non-specific nucleic acid cleaving chemicals or enzymes or site-specific restriction endonucleases; or by synthesis by standard methods known in the art, e.g. by use of a commercially available automated DNA synthesizer and standard phosphoramidite chemistry. One method for synthesizing oligonucleotides on a modified solid support is described in U.S. Pat. No. 4,458,066.

Once a desired synthetic nucleic acid is synthesized, it can be cleaved from a solid support on which it was synthesized and treated, by methods known in the art, to remove any protecting groups present. The synthetic nucleic acids may then be purified by any method known in the art, including extraction and gel purification. The concentration and purity of the oligonucleotide may be determined by, for example, examining the oligonucleotide on an acrylamide gel, by HPLC, or by measuring the optical density at 260 nm in a spectrophotometer.

The synthetic nucleic acid sequences of the invention can be used in any assay which is used to determine for the presence of the expression of IR-A and IR-B. In one example, isolated nucleic acids such as disclosed herein can be used in an amplification process. Amplification refers to a process for multiplying nucleic acid strands in vitro. An exemplary technique is PCR, which exponentially amplifies nucleic acid molecules. PCR is described in U.S. Pat. No. 4,683,195 and U.S. Pat. No. 4,683,202. PCR is extensively used for specific detection and quantification of target nucleic acid sequences polynucleotides and is a standard method in molecular biology. PCR can be used to determine expression of IR-A and/or IR-B in a test sample. The method uses a pair of isolated nucleic acid sequences, "primers", which specifically anneal to specific locations on the IR-A or IR-B DNA molecule. The IR-A or IR-B DNA is heat denatured and two oligonucleotides that bracket the target sequence on opposite strands of the DNA to be amplified, are hybridized. These oligonucleotides become primers for use with DNA polymerase. The DNA is copied by primer extension to make a second copy of both strands. By repeating the cycle of heat denaturation, primer hybridization and extension, the target IR-A or IR-B DNA can be amplified a million fold or more in about two to four hours. PCR is a molecular biology tool which must be used in conjunction with a detection technique to determine the results of amplification. An advantage of PCR is that it increases sensitivity by amplifying the amount of target DNA by 1 million to 1 billion fold in approximately 4 hours.

As discussed below and illustrated in the examples a useful method of using IR-A primers and probes is quantitative PCR. Quantitative PCR refers to methods where the PCR reaction is combined with fluorescence chemistry to enable real-time monitoring of the amplification reaction using detection of a fluorescent light signal. In one example the method uses a sequence nonspecific fluorescent reporter dye such as SYBR green (Wittwer C T et al., Biotechniques. 1997 January; 22(1):176-81). In another example, the method uses a sequence specific fluorescent reporter such as a TAQMAN probe (Heid C A et al., Genome Res. 1996 October; 6(10): 986-94). During execution of the PCR cycling program, the samples are excited using a light source. A fluorescent signal, indicating the amount of PCR amplification product produced, is monitored in each reaction well using a photodetector or CCD/CMOS camera. By monitoring the fluorescence in the sample during the reaction precise quantitative measurements can be made. The probe based PCR method is considered to more accurate than the SYBR green method. PCR or qPCR is typically performed in plastic 96 or 384 well microtiter plates, each reaction having a volume in the order of 5-50 µl. PCR can however be carried out in very small (nanoliter) volumes.

The term "primer" or "primer pair" as used herein refers to short oligonucleotides (typically 10-30 bp) which are used in PCR to prime a polymerization reaction. Specific primers may be used to select an IR-A or IR-B DNA sequence to be amplified by priming a polymerization at a specific location in the target sequence.

The methods described herein provide a method for the reproducible and robust amplification of small amounts of DNA which contain IR-A and/or IR-B. Performing qPCR using the nucleic acid primers described herein can specifically detect IR-A or IR-B from 0.1 picograms of DNA (1000 copies) or from 35 copies of the DNA.

A biological sample may comprise RNA that in some implementations of the method is first transcribed into cDNA. Total cellular RNA, cytoplasmic RNA, or poly(A)+RNA may be used. Methods for preparing total and poly(A)+RNA are well known and are described generally in Sambrook et al. (1989, Molecular Cloning—A Laboratory Manual (2nd Ed.), Vols. 1-3, Cold Spring Harbor Laboratory, Cold Spring Harbor, N.Y.) and Ausubel et al., eds. (1994, Current Protocols in Molecular Biology, vol. 2, Current Protocols Publishing, New York). Preferably, total RNA is prepared by the techniques described by Chirgwin et al, (1987), Chomczynski & Sacchi (1987), Sambrook et al, (1989), or Farrell Jr. (1993), and a number of high quality commercial kits are also available. More preferably, total RNA used is prepared using the guanidinium thiocyanate method of Chirgwin et al, (1987). The integrity of total RNA may be checked using various methods that are known in the art. By way of example, the RNA may be analyzed using RNA gel electrophoresis (e.g. formaldehyde/agarose gel), or Agilent LabChip. For mammalian total RNA, two bands at approximately 4.5 and 1.9 kb should be visible; these bands represent 28S and 18S ribosomal RNA respectively, and the ratio of intensities of these bands should typically be 1.5-2.5:1.

RNA purification kits for microscale RNA preparation are available from a number of commercial suppliers (for example Absolutely RNA™ Nanoprep, Stratagene; PicoPure™, Arcturus; RNeasy®, Qiagen; RNAqueous™ Microkit, Ambion).

The cDNA synthesis oligonucleotide for first strand cDNA synthesis may be hybridized to RNA in a suitable buffer at a temperature between about 60° C. and 90° C., preferably about 70° C. for about 5 minutes, followed by cooling to about 4° C., before the reverse transcriptase is added. Following the hybridization of the cDNA synthesis oligonucleotide to RNA, a first cDNA strand is synthesized. This first strand of cDNA is preferably produced through the process of reverse transcription, wherein DNA is made from RNA, utilizing reverse transcriptase following methods that are familiar to a person skilled in the art.

Any reverse transcriptase may be used to transcribe RNA to DNA as long as the enzyme adds deoxyribonucleotides to the 3' terminus following extension (Varmus, Science 240: 1427-1435 (1988)) and the enzyme lacks RNaseH activity. Preferably, the reverse transcriptase lacks RNaseH activity but retains wild-type polymerase activity such that longer cDNAs can be synthesized. The reverse transcriptase may be Moloney Murine Leukemia virus (MMLV) reverse transcriptase or a mutant thereof. The reverse transcriptase may be PowerScript™ Reverse Transcriptase (BD Biosciences Clontech). The reverse transcriptase may be SuperScript III™.

The amount of reverse transcriptase employed may vary as will be appreciated by a person skilled in the art. The reverse transcription is performed by incubation for, for example, approximately 1 hour with reverse transcriptase at an appropriate temperature, which must be in a temperature range in which the reverse transcriptase retains enzyme activity. The reaction may be performed between 37° C. and 55° C., preferably between 37° C. and 42° C. Most preferably, the reaction is performed at optimal enzyme activity—such as at about 42° C. The reverse transcription reaction may be terminated by heating the reaction mixture to 95° C. for about 5 minutes to inactivate the enzyme, optionally, followed by chilling on ice.

C. IGF Antagonists/Agonists

IGF agents as used herein refers to an agent that affects expression or activity of any member of the IGF-1R/IR signaling pathway and includes IGF-1R, IR, INSR, or IGFI/II antagonists or agonists. The IGF-1R, IR, INSR, or IGFI/II antagonist or agonist can be a peptidomimetic, protein, peptide, nucleic acid, small molecule, an antibody or other drug candidate. Examples of IGF-R1 antagonists are well known in the art and include anti-sense and nucleic acids that antagonize IGF-1R have been described, e.g., in Wraight et al., Nat. Biotech., 18: 521-526 (2000); U.S. Pat. No. 5,643,788; U.S. Pat. No. 6,340,674; US 2003/0031658; U.S. Pat. No. 6,340,674; U.S. Pat. No. 5,456,612; U.S. Pat. No. 5,643,788; U.S. Pat. No. 6,071,891; WO 2002/101002; WO 1999/23259; WO 2003/100059; US 2004/127446; US 2004/142895; US 2004/110296; US 2004/006035; US 2003/206887; US 2003/190635; US 2003/170891; US 2003/096769; U.S. Pat. No. 5,929,040; U.S. Pat. No. 6,284,741; US 2006/0234239; and U.S. Pat. No. 5,872,241.

Further, US 2005/0255493 discloses reducing IGF-1R expression by RNA interference using short double-stranded RNA. In addition, inhibitory peptides targeting IGF-1R have been generated that possess antiproliferative activity in vitro and in vivo (Pietrzkowski et al., Cancer Res., 52:6447-6451 (1992); Haylor et al., J. Am. Soc. Nephrol., 11:2027-2035 (2000)). A C-terminal peptide of IGF-1R has been shown to induce apoptosis and significantly inhibit tumor growth (Reiss et al., J. Cell. Phys., 181:124-135 (1999)). Also, a soluble form of IGF-1R inhibits tumor growth in vivo (D'Ambrosio et al., Cancer Res., 56: 4013-4020 (1996)). Small-molecule inhibitors to IGF-1R are described, e.g., in Garcia-Echeverria et al., Cancer Cell, 5: 231-239 (2004); Mitsiades et al., Cancer Cell, 5: 221-230 (2004); and Carboni et al., Cancer Res, 65: 3781-3787 (2005).

Further examples of disclosures on such small-molecule inhibitors include WO 2002/102804; WO 2002/102805; WO 2004/55022; U.S. Pat. No. 6,037,332; WO 2003/48133; US 2004/053931; US 2003/125370; U.S. Pat. No. 6,599,902; U.S. Pat. No. 6,117,880; WO 2003/35619; WO 2003/35614; WO 2003/35616; WO 2003/35615; WO 1998/48831; U.S. Pat. No. 6,337,338; US 2003/0064482; U.S. Pat. No. 6,475,486; U.S. Pat. No. 6,610,299; U.S. Pat. No. 5,561,119; WO 2006/080450; WO 2006/094600; and WO 2004/093781 See also WO 2007/099171 (bicyclo-pyrazole inhibitors) and WO 2007/099166 (pyrazolo-pyridine derivative inhibitors). See also (Hubbard et al., AACR-NCI-EORTC Int Conf Mol Targets Cancer Ther (October 22-26, San Francisco) 2007, Abst A227) on Abbott Corporation's molecule A-928605.

Examples of IGF agents include IGF-I/II agonists or antagonists. Specific IGF-II antagonists are also known in the art and include antibodies that bind IGF-I and/or IGF-II. Such antagonists are disclosed in WO 2007022172 and EP 492552. Examples of antibodies that bind both IGF-I and IGF-II include those described in WO2007070432, WO05/18671, WO 03/093317, WO 05/027970, and WO 05/028515.

A specific example of antibodies that are useful as IGF antagonists include those heavy and light chain components listed in Tables 1 and 2. These antibodies are disclosed in WO2007070432, which is incorporated by reference herein in its entirety. Particular antibodies include those designated 7.159.1, 7.158.1 and 7.34.1. The agents and antibodies disclosed above are incorporated into the present application in their entirety.

TABLE 1

Anti-IGF I/II Antibody Heavy Chain Analysis

| Chain Name | V | D | J | FR1 | CDR 1 | FR2 | CDR2 | FR3 | CDR3 | FR4 |
|---|---|---|---|---|---|---|---|---|---|---|
| Germline ** SEQ ID NO: 44 | VH1-8 | N.A. | JH6B | QVQLVQSG AEVKKPGA SVKVSCKA SGYTFT | SYD IN | WVRQ ATGQ GLEW MG | WMNPNS GNTGYA QKFQG | RVTMTRNT SISTAYME LSSLRSED TAVYYCAR | ##YY YYYG MDV | WGQG TTVT VSSA |
| 7.159.1 SEQ ID NO: 45 | VH1-8 | N.A. | JH6B | QVQLVQSG AEVKKPGA SVKVSCKA SGYTFT | SYD IN | WVRQ ATGQ GLEW MG | WMNPNS GNTGYA QKFQG | RVTMTRNT SISTAYME LSSLRSED TAVYYCAR | DPYY YYYG MDV | WGQG TTVT VSSA |

TABLE 1-continued

Anti-IGF I/II Antibody Heavy Chain Analysis

| Chain Name | V | D | J | FR1 | CDR1 | FR2 | CDR2 | FR3 | CDR3 | FR4 |
|---|---|---|---|---|---|---|---|---|---|---|
| Germline SEQ ID NO: 46 | VH4-39 | D6-19 | JH2 | QLQLQESG PGLVKPSE TLSLTCTV SGGSIS | SSS YYW G | WIRQ PPGK GLEW IG | SIYYSG STYYNP SLKS | RVTISVDT SKNQFSLK LSSVTAAD TAVYYCAR | #### SS## WYFD L | WGRG TLVT VSSA |
| 7.158.1 SEQ ID NO: 47 | VH4-39 | D6-19 | JH2 | QLQLQESG PGLVKPSE TLSLTCTV SGGSIR | SSS YYW G | WIRQ PPGK GLEW IG | GIYYSG STYYNP SLKS | RVTMSVDT SKNQFSLK LSSVTAAD TAVYYCAR | QRGH SSGW WYFD L | WGRG TLVT VSSA |
| 7.234.1 SEQ ID NO: 48 | VH4-39 | D6-19 | JH2 | QVQLQESG PGLVKPSE TLSLTCTV SGGSIN | SSS NYW G | WIRQ PPGK GLAW IG | GIYYSG STYYNP SLRS | RVTMSVDT SKNQFSLK LSSVTAAD TAVYYCAR | QRGH SSGW WYFD L | WGRG TLVT VSSA |
| Germline SEQ ID NO: 49 | VH4-59 | D1-20 | JH6B | QVQLQESG PGLVKPSE TLSLTCTV SGGSIS | SYY WS G | WIRQ PPGK GLEW IG | YIYYSG STNYNP SLKS | RVTISVDT SKNQFSLK LSSVTAAD TAVYYCA# R | ITGT ###G MDV | WGQG TTVT VSSA |
| 7.34.1 SEQ ID NO: 50 | VH4-59 | D1-20 | JH6B | QVQLQESG PGLVKPSE TLSLTCTV SGGSIS | SYY WS G | WIRQ PPGR GLEW IG | YFFYSG YTNYNP SLKS | RVTMSVDT SKNQFSLK LSSVTAAD TAVYYCAC | ITGT TKGG MDV | WGQG ATVT VSSA |
| 7.251.3 SEQ ID NO: 51 | VH4-59 | D1-20 | JH6B | QVQLQESG PGLVKPSE TLSLTCTV SGGSIS | SYY WS G | WIRQ PPGK GLEW IG | YFFYSG YTNYNP SLKS | RVTISVDT SKNQFSLK LSSVTAAD TAVYYCAC | ITGT TKGG MDV | WGQG TTVT VSSA |

\* The hatch designation (#) indicates a space in the germline and is used to show a proper alignment with the antibody sequences shown in the table.
\*\* The germline sequences shown in the above table are for alignment purposes, and it should be realized that each individual antibody region exists in its own location within the variable regions of immunoglobulin germline DNA segments in vivo.

TABLE 2

Anti-IGF I/II Antibody Light Chain Analysis

| Chain Name | V | J | FR1 | CDR1 | FR2 | CDR2 | FR3 | CDR3 | FR4 |
|---|---|---|---|---|---|---|---|---|---|
| Germline SEQ ID NO: 52 | V1-19 | JL2 | QSVLTQP PSVSAAP GQKVTIS C | SGSSSN IGNNYV S | WYQQLP GT | APKLLIY DNNKRPS | GIPDRFSGSKS GTSATLGITGL QTGDEADYYC | GTWD SSLS A##V | FGGG TKLT VLG |
| 7.159.1 SEQ ID NO: 53 | V1-19 | JL2 | QSVLTQP PSVSAAP GQKVTIS C | SGSSSN IENNHV S | WYQQLP GTAPKL LIY | DNNKRPS | GIPDRFSGSKS GTSATLGITGL QTGDEADYYC | ETWD TSLS AGRV | FGGG TKLT VLG |
| Germline SEQ ID NO: 54 | L5 | JK3 | DIQMTQS PSSVSAS VGDRVTI TC | RASQGI SSWLA | WYQQKP GKAPKL LIY | AASSLQS | GVPSRFSGSGS GTDFTLTISSL QPEDFATYYC | QQAN SFPF T | FGPG TKVD IKR |
| 7.158.1 SEQ ID NO: 55 | L5 | JK3 | DIQMTQS PSSVSAS VGDSVTI TC | RASQGI SSYLA | WYQQKP GKAPKL LIY | AASSLQS | GVPSRFSGNGS GTDFTLTISSL QPEDFATYYC | QQAN NFPF T | FGPG TKVD IKR |
| 7.234.1 SEQ ID NO: 56 | L5 | JK3 | DIQMTQS PSSVSAS VGDRVTI TC | RASRGI SSWLA | WYQQRP GKAPKL LIY | TASSLQS | GVPSRFSGSGS GTDFTLTISSL QPEDFATYYC | QQAN SFPF T | FGPG TKVD IKR |
| Germline SEQ ID NO: 57 | V1-13 | JL2 | QSVLTQP PSVSGAP GQRVTIS C | TGSSSN IGAGYD VH | WYQQLP GTAPKL LIY | GNSNRPS | GVPDRFSGSKS GTSASLAITGL QAEDEADYYC | QSYD GSV | FGGG TKLT VLG |

TABLE 2-continued

Anti-IGF I/II Antibody Light Chain Analysis

| Chain Name | V | J | FR1 | CDR1 | FR2 | CDR2 | FR3 | CDR3 | FR4 |
|---|---|---|---|---|---|---|---|---|---|
| 7.34.1 SEQ ID NO: 58 | V1-13 | JL2 | QSVLTQA PSVSGAP GQRVTIS C | TGRSSN IGAGYD VH | WYQQFP GTAPKL LIY | GNSNRPS | GVPDRFSGSKS GTSASLAITGL QAEDEADYYC | QSYD SSLS GSV | FGGG TKLT VLG |
| 7.251.3 SEQ ID NO: 59 | V1-13 | JL2 | QSVLTQP PSVSGAP GQRVTIS C | TGSSSN IGAGYD VH | WYQQLP GTAPKL LIY | GNNNRPS | GVPDRFSGSKS GTSASLAITGL QADDEADYYC | QSFD SSLS GSV | FGGG TKLT VLG |

\* The hatch designation (#) indicates a space in the germline and is used to show a proper alignment with the antibody sequences shown in the table.
\*\* The germline sequences shown in the above table are for alignment purposes, and it should be realized that each individual antibody region exists in its own location within the variable regions of immunoglobulin germline DNA segments in vivo.

D. Methods of Detecting and/or Quantifying IR-A and IR-B Expression

The IR-A and IR-B synthetic nucleic acid sequences, primers and probe sets disclosed above can be used to determine the level of IR-A or IR-B in a sample. Given the sensitivity of the assay, the molecules of the present invention can have numerous uses.

A preferred approach is to use a real-time polymerase chain reaction, also called quantitative real time polymerase chain reaction (variously abbreviated Q-PCR, qPCR, qrt-PCR, or RTQ-PCR) or kinetic polymerase chain reaction (KPCR). Frequently, real-time PCR is combined with reverse transcription to quantify messenger RNA and non-coding RNA in cells or tissues. Reverse transcription PCR permits starting from an RNA containing sample without prior preparation of cDNA. Real-time reverse-transcription PCR is often denoted as qRT-PCR, RRT-PCR, or RT-rt PCR. It enables both detection and quantification (as absolute number of copies or relative amount when normalized to DNA input or additional normalizing genes) of one or more specific sequences in a DNA sample.

The procedure follows the general course of a polymerase chain reaction. However, amplified DNA is detected as the reaction progresses in real time. Two common methods for detection of products in real-time PCR are: (1) non-specific fluorescent dyes that intercalate with any double-stranded DNA, and (2) sequence-specific DNA probes consisting of oligonucleotides that are labeled with a fluorescent reporter which permits detection only after hybridization of the probe with its complementary DNA target.

Fluorescent reporter probes detect only the DNA containing the probe sequence; therefore, use of the reporter probe significantly increases specificity, and enables quantification even in the presence of non-specific DNA amplification. Fluorescent probes can be used in multiplex assays—for detection of several genes in the same reaction—based on specific probes with different-colored labels, provided that all targeted genes are amplified with similar efficiency.

The method generally uses a DNA-based probe with a fluorescent reporter at one end and a quencher of fluorescence at the opposite end of the probe. The close proximity of the reporter to the quencher prevents detection of its fluorescence; breakdown of the probe by the 5' to 3' exonuclease activity of a polymerase separates the reporter from the quencher and thus allows unquenched emission of fluorescence. An increase in the product targeted by the reporter probe at each PCR cycle therefore causes a proportional increase in fluorescence due to the breakdown of the probe and release of the reporter.

A PCR sample is prepared as usual, and the reporter probe is added. As the reaction commences, during the annealing stage of the PCR both probe and primers anneal to the DNA target.

Polymerization of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in the real-time PCR thermocycler, and its geometric increase corresponding to exponential increase of the product is used to determine the threshold cycle (CT) in each reaction.

Relative concentrations of DNA present during the exponential phase of the reaction can be determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, Ct. The quantity of DNA theoretically doubles every cycle during the exponential phase and relative amounts of DNA can be calculated, e.g. a sample whose Ct is 3 cycles earlier than another's has $2^3=8$ times more template. Since all sets of primers don't work equally well, one has to calculate the reaction efficiency first. Thus, by using this as the base and the cycle difference C(t) as the exponent, the difference in starting template can be calculated as $(2 \times \% \text{ eff})^{Ct}$.

Amounts of RNA or DNA can then be determined by comparing the results to a standard curve produced by real-time PCR of serial dilutions (e.g. undiluted, 1:4, 1:16, 1:64) of a known amount of RNA or DNA. To accurately quantify gene expression, the measured amount of RNA from the gene of interest is divided by the amount of RNA from a housekeeping gene measured in the same sample to normalize for possible variation in the amount and quality of RNA between different samples. This normalization permits accurate comparison of expression of the gene of interest between different samples, provided that the expression of the reference gene used in the normalization is very similar across all the samples.

Mechanism based qPCR quantification methods have also been described, such as MAK2. They do not require a standard curve for quantification. These mechanism based methods use knowledge about the polymerase amplification process to generate estimates of the original sample concentration.

Real-time PCR can be used to determine relative quantities and absolute quantities. Relative quantification measures the fold-difference (2×, 3× etc.) in the target amount. Absolute quantification gives the exact number of target molecules present by comparing with known standards.

E. Diagnostic Classification of a Tumor

A method of classifying a tumor can comprise providing a tumor sample; contacting the sample with a synthetic IR-A specific oligonucleotide; and detecting or quantifying the amount of IR-A in the tumor. A quantification of IR-A in the tumor may be compared to a control tissue sample or to a population average for normal tissue. For example, a breast cancer tumor sample may be compared to a sample from non-affected breast of the same patient or to a population average for non-affected breast tissue. Increased expression of IR-A indicates that the tumor is an IR-A expressing tumor.

A method of classifying a tumor can alternatively include detecting and/or quantifying the amount of IR-B in a tumor compared to a control sample or a population average. Thus, a method of classifying a tumor can comprise providing a tumor sample; contacting the sample with a synthetic IR-B specific oligonucleotide; and detecting or quantifying the amount of IR-B in the tumor. A quantification of IR-B in the tumor may be compared to a control tissue sample or to a population average for normal tissue. For example, a breast cancer tumor sample may be compared to a sample from a non-affected breast of the same patient or to a population average for non-affected breast tissue. Increased expression of IR-B indicates that the tumor is an IR-B expressing tumor.

A method of classifying a tumor can include determining the relative expression levels of IR-A and IR-B. The relative expression can be described as a ratio of IR-A:IR-B mRNA, or as a percentage of either as a proportion of the total IR mRNA, e.g., % IR-A. The relative expression of IR-A and IR-B can also be described by the differential of the threshold cycles in a qPCR, e.g. (IR-A $\Delta$Ct)−(IR-B $\Delta$Ct)=$\Delta\Delta$Ct, the ratio of IR-A mRNA to IR-B mRNA in the sample being approximately equal to $2^{-\Delta\Delta Ct}$. For $\Delta$Ct calculation, the experimental Ct values can be normalized against an internal standard. For example, a mean of in-sample (i.e., obtained from the same sample as IR-A and/or IR-B expression) Ct values of a gene expression panel, such as the average Ct of one or more housekeeping genes, can be used for normalization of Ct values for IR-A and IR-B to calculate $\Delta$Ct values.

To classify a tissue sample, such as a tumor tissue sample, based upon the percentage of IR-A relative to total INSR expression, the mean and standard deviation of the percentage of IR-A in the tissue type is first determined. In another approach, the confidence range of the mean is statistically determined for a pre-selected confidence interval, e.g. 95%, 97.5%, 99% or 99.9% confidence. The percentage of IR-A relative to total INSR expression in the tissue sample is then determined in the tissue sample. If the percentage of IR-A out of the total INSR expression is greater than the mean, then the tissue may be said to have an elevated proportion of IR-A expression. If the proportion of IR-A out of the total INSR expression is greater than 1 to 3 standard deviations, e.g. greater than 2 standard deviations then the sample may be said to have a substantially elevated proportion of IR-A. Similarly, if the proportion of IR-A out of the total INSR expression is greater than the upper confidence interval of the mean value for a pre-selected confidence level, then the tissue may be said to have an abnormally high proportion of IR-A. A classification may be assigned to a tissue sample that exceeds 1, 2, or 3 times the 95%, 97.5%, 99% or 99.9% confidence interval of a mean value for a type of tissue.

Alternatively, a mean percentage of IR-A mRNA relative to total INSR mRNA and a confidence interval for a pre-selected confidence level may be determined for a known classification of tumor. If a measured IR-A percentage of a tissue sample falls within the confidence interval, the measurement may be said to be consistent with the tumor classification.

As an example, normal breast tissue has been determined to contain 46.6±4.7% IR-A mRNA as a proportion of total INSR mRNA at 95% confidence. Breast tumor tissue has been found to contain 75.24% IR-A relative to total INSR mRNA with a 95% confidence interval of ±5%. These measurements have been determined to be significantly different (p<0.0001). A tissue sample IR-A percentage greater than 46.6% could be said to indicate a higher than average percentage of IR-A. However, setting a threshold of about 60%, nearly mid-point between the mean values of normal and tumor tissue and well beyond the respective 95% confidence ranges will minimize the number of incorrectly classified samples. A skilled practitioner may adjust the threshold in the range 47-75%, for example selecting a threshold in the range 55% to 65%, to favor a more or less inclusive classification.

As another example IR-A and IR-B $\Delta$Ct values may be determined for normal tissue of any given type. Tissue samples determined to have (IR-A $\Delta$Ct)−(IR-B $\Delta$Ct) differentials that are more than 1, 2, 3 or more standard deviations below the mean value may be classified as having disproportionate levels of IR-A expression relative to IR-B expression. By contrast, a positive $\Delta$Ct differential indicates a disproportionate level of IR-B expression. To illustrate, IR-A:IR-B $\Delta$Ct differentials were determined in normal and primary tumor breast samples. The mean IR-A:IR-B $\Delta\Delta$Ct±95% CI was 0.20±0.23 for normal (n=19) and the mean IR-A:IR-B $\Delta\Delta$Ct differentials±95% CI was −1.81±0.27 in primary tumors (n=42). Thus, a tissue sample having a IR-A:IR-B $\Delta\Delta$Ct<about 0.2 may be said to have a higher than average IR-A:IR-B $\Delta\Delta$Ct, indicating a higher than average proportion of IR-A expression. However, setting a threshold of about −0.4, −0.6, −0.8, −1.0 or −1.2 would provide increasing levels of confidence. Setting a threshold near the midpoint (in this example at an IR-A:IR-B $\Delta\Delta$Ct of about −0.7 to −0.9) would minimize the number of incorrect classifications. Of course, a skilled practitioner may adjust the threshold anywhere in the range between mean values to balance the needs of the classification to be more or less inclusive. Thus, a threshold for classifying a sample as having IR-A:IR-B $\Delta\Delta$Ct differentials consistent with breast tumor tissue having an altered amount of IR-A relative to IR-B may be set in the range 0.2 to −1.8, for example between about 0.4 and about −1.54, based on the 95% confidence interval.

As another example, relative expression of IR-A and IR-B may be used to classify tumor subtypes, for example, luminal A and luminal B breast cancers. For example, IR-A:IR-B $\Delta$Ct differentials in the normal, luminal A and luminal B were compared. The mean IR-A:IR-B $\Delta\Delta$Ct±95% CI was 0.27±0.30 in normal (n=15). The mean IR-A:IR-B $\Delta\Delta$Ct±95% CI was −1.09±0.34 in luminal A classified breast cancers (n=13). The mean IR-A:IR-B $\Delta\Delta$Ct±95% CI was −2.12±0.34 in luminal B classified breast cancers (n=27). All subtype pair-wise comparisons display a significant difference (two-sample t-test, p<0.001). Accordingly, a threshold for IR-A:IR-B $\Delta\Delta$Ct classification between normal and luminal A tumor tissue may be set in the range between about 0.3 to −1.4, for example at about −0.2, about −0.4, or about −0.6. A threshold for IR-A:IR-B ΔΔCt classification between luminal A and luminal B tumor tissue may be set in the range between about −1.1 to about −2.1, for example in the range between about −1.5 to −1.75, or at about −1.55, about −1.6, about −1.65, or about −1.7.

Using a classification scheme for normal, luminal-A, and luminal-B, based upon GeneChip expression profiles, IR-A: IR-B ΔCt differentials in normal, luminal-A and luminal-B classified tumor samples were compared. The mean IR-A: IR-B ΔΔCt±95% CI was 0.32±0.25 in normal (n=15). The mean IR-A:IR-B ΔΔCt±95% CI was −1.05±0.19 in luminal-A predicted breast cancers (n=18). The mean IR-A:IR-B ΔΔCt±95% CI was −2.42±0.32 in luminal-B predicted breast cancers (n=22). In accordance with this scheme, a threshold for IR-A:IR-B ΔΔCt classification between luminal A and luminal B tumor tissue may be set in the range between about −1.1 to about −2.4, for example in the range between about −1.4 to −2.1, or at about −1.4, about −1.6, about −1.7, about −1.8, or about −1.9. IR-A:IR-B ΔΔCt may be combined with other expression profiles to further refine subtype classifications.

Relative IR-A and IR-B expression levels in tissues may be used as a predictor of cancer proliferation, particularly in combination with other predictors of cancer proliferation, for example to determine a proliferation score. Predicted proliferation rates can provide useful information on prognosis and aggressiveness of individual cancers. The data above illustrate a positive correlation between the IR-A:IR-B ΔCt differential and the proliferation score. Thus, a method for scoring tumor tissue may comprise determining the relative proportion of IR-A and IR-B expression and assigning a proliferation score based at least in part upon the relative expression of IR-A and IR-B.

Tumor samples for classification using these methods can be any appropriate tumor sample including a sample from a lung, breast, prostate, colon, ovary, pancreas, brain, esophagus, endometrium, cervix, gastrointestinal tract or skin. Tumor samples can be taken from any patient where the tumor activity is mediated alone, or in part, through a cell surface receptor such as IGF-R1/IR-A. For example, the tumor can be a non-solid tumor such as leukemia, multiple myeloma or lymphoma, or can be a solid tumor, for example bile duct, bone, bladder, brain/CNS, breast, colorectal, cervical, endometrial, gastric, head and neck, hepatic, lung, muscle, neuronal, esophageal, ovarian, pancreatic, pleural/peritoneal membranes, prostate, renal, skin, testicular, thyroid, uterine and vulval tumors. In one example, the tumor is a tumor of the breast. In another example, the tumor is of the bladder. In another example, the tumor is of the liver.

Appropriate tumor samples can be prepared as known in the art. For example, live tumor cells are obtained via a needle biopsy and then cultured in vitro according to standard procedures. Alternately, one could fix the tumor cells immediately following aspiration or remove the tumor (in whole or in part) and prepare a section for immunohistological staining.

In vitro culturing of tumor cells will enable the measurement of internalization dynamics following stimulation, while immediately fixing samples will result in assaying the static localization of the receptor within the tumor.

F. Methods of Treatment

Figure 3:
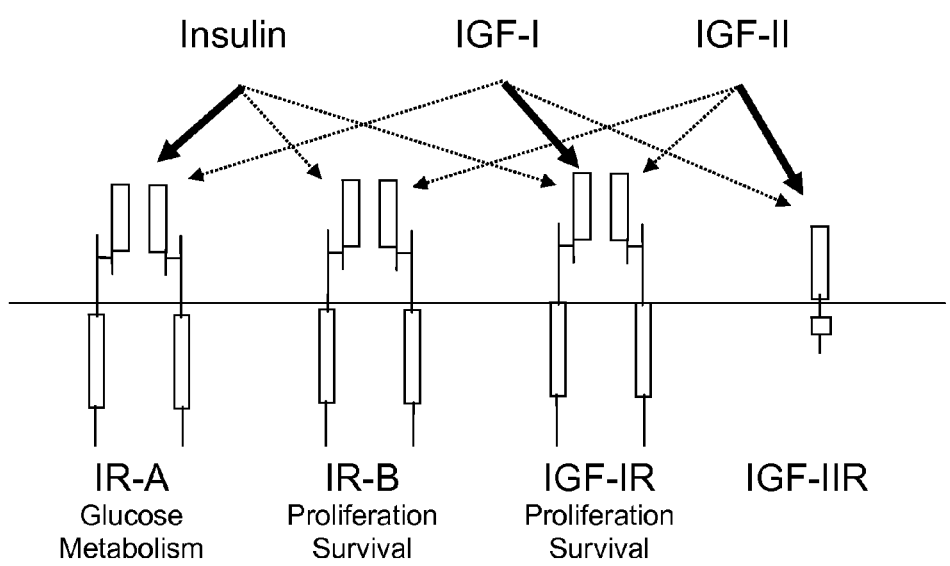
FIG. 3 shows a schematic of IGF-1R/IR receptors illustrating strong and weak ligand interactions.

The IGF-1 receptor (IGF-IR) pathway is complex and includes multiple players (see FIG. 3). IGF-1R can and does form hybrid receptors with the insulin receptor (INSR). IGF ligands, IGF-I and IGF-II, exert their various actions by primarily interacting with IGF-IR and activating various intracellular signaling cascades. Specifically, IGF-I functions primarily by activating the IGF-IR, whereas IGF-II can act through either the IGF-IR or through the IR-A isoform. IGF-1R, its IGF ligands and IR-A are implicated in numerous cancers including both breast and prostate cancer and numerous antagonists for use in cancer treatment have been developed to target IGF-IR and the IGF ligands.

Given the multitude of antagonists currently available that target the IGF pathway, the selection of an antagonist to which a patient is likely to respond or has heightened response is desired. For example, IGF-1R antagonists suffer from the limitation that these antagonists do not inhibit the IR-A pathway. Given that the literature suggests that IR-A when overexpressed in cancer can be responsible for resistance to IGF-1R antagonists, it is desirable to administer an antagonist that targets not just IGF-1R but also IR-A. An example of such an antagonist in an antibody that specifically targets IGF-II and can cross-react with IGF-I.

These IGF-I and II antagonists have the ability to inhibit both IGF-IR and IR-A signaling, resulting in a broader activity in the clinic than IGF-1R and reduced toxicity compared to small molecule IGF-1R/IR-A/IR-B inhibitors. Examples include the antibodies against IGF-I and/or IGF-II, including those disclosed in WO2007070432. Of particular interest are antibodies having the amino acid sequence of the antibody produced by hybridomas 7.159.1, 7.158.1 and 7.34.1.

A method of selecting patients who are candidates for treatment with an IGF antagonist or agonist in order to predict an increased likelihood of response to a particular IGF antagonist or agonist can comprise quantifying IR-A and/or IR-B expression using any of the above methods and selecting a patient who expresses an increased or decreased amount of IR-A and/or IR-B relative to normal subjects or relative to a population of cancer patients. Patients may also be selected according to altered relative amounts of IR-A versus IR-B expression.

In a specific example, a practitioner may pre-select a particular IGF antagonist based on the determination if the tumor expresses IR-A and/or IR-B. The identification of a tumor that has been determined to overexpress IR-A provides the opportunity to select patients that will most likely have increased responsiveness to an IGFI/II antagonist.

In one example, the antagonist is an antibody comprising an amino acid sequence comprising the amino acid sequences of SEQ ID NOs: 45 and 53. In another example, the antagonist is an antibody comprising the CDR sequences of SEQ ID NOs: 45 and 53, as shown in Tables 1 and 2. In another example, the antagonist comprises an antibody comprising three CDRs from SEQ ID NO: 45 and a light chain. In another example, the antagonist comprises an antibody comprising three CDRs from SEQ ID NO: 53 and a heavy chain.

The method can also be used to determine if a particular inhibitor of IGF-1R or IGF is activating or inhibiting the insulin receptor. For example, it is known that small molecule inhibitors of the IGF-1R kinase often cross-inhibit the insulin receptor. This can lead to metabolic complications. In one example, a method determining for the expression of IR-A and/or IR-B in a sample such as a tumor and comparing their expression to a control. If the expression of IR-B is decreased compared to a control and expression of IR-A is increased compared to a control, then alternative selection of an IGF antagonist may be required such as an IGF-I/II antagonist. Thus, a method of treating a patient may comprise determining the relative expression of IR-A and IR-B, for example by determining an IR-A:IR-B ΔCt differential for a tissue sample from a patient, and administering an IGF-I/II antagonist if the proportion of IR-A relative to IR-B is lower than a threshold value.

In another example, a method allows for the classification of a subset of cancer patients. Currently it is known that IR-A may be overexpressed in breast cancer. A method of selecting a subset of patients for treatment may comprise identification of a subset of breast cancer patients who overexpress IR-A, or who express IR-A disproportionately relative to IR-B, and who are therefore likely to have a heightened response to an IGFI/II antagonist. A method of treating cancer patients who are likely to have a heightened response to an IGFI/II antagonist can comprise measuring an IR-A:IR-B ΔCt differential for a tumor tissue sample and administering an effective dose of an IGFI/II antagonist if the IR-A:IR-B ΔCt differential of the tumor tissue sample is below a threshold value indicating a higher than normal proportion of IR-A relative to IR-B. Examples of antagonists include antibodies that bind IGF-I and/or IGF-II. In one example, the antagonist is an antibody comprising an amino acid sequence comprising the amino acid sequences of SEQ ID NOs: 45 and 53. In another example, the antagonist is an antibody comprising the CDR sequences of SEQ ID NOs: 45 and 53, as shown in Tables 1 and 2. In another example, the antagonist comprises an antibody comprising three CDRs from SEQ ID NO: 45 and a light chain. In another example, the antagonist comprises an antibody comprising three CDRs from SEQ ID NO: 53 and a heavy chain.

By heightened response or responders it is meant patients that will respond, or respond more positively, following administration of a particular IGF agent. Responders and non responders can be determined by measuring objective tumor responses according to the Union International Contre le Cancer/World Health Organization (U ICC/WHO) criteria. The criteria are categorized as follows: complete response (CR): no residual tumor in all evaluable lesions; partial response (PR): residual tumor with evidence of chemotherapy-induced 50% or greater decrease under baseline in the sum of all measurable lesions and no new lesions; stable disease (SD): residual tumor not qualified for CR; and progressive disease (PD): residual tumor with evidence of 25% or greater increase under baseline in the sum of all measurable lesions or appearance of new lesions. As defined herein non-responders are PD. The methods are particularly effective for determining those patients that are CR or PR. The methods thus permit improved prognosis and quality of life of cancer patients by matching the treatments to individual patients and so making more effective use of the types of IGF antagonists available.

G. Diabetes

A method for screening for substances/compounds that abolish and/or decrease signaling via insulin receptors. Determining the relative expression of IR-A or IR-B in a sample can be used as a screening tool to identify agents such as small molecule compounds and/or insulin mimetics, that selectively activate either IR-A or IR-B-specific signaling cascades, e.g. in the beta cell and in peripheral tissues. The pronounced expression of IR-B in the classical insulin target tissues indicates the importance of the IR-B signaling cascade in these tissues. Consequently compounds that selectively stimulate the IR-B signaling cascade will improve the function of the beta cell (glucose responsiveness and therefore insulin secretion), as well as the function of the peripheral insulin target tissues (glucose uptake and utilization, protein synthesis, lipid synthesis) and thus potentially provide a treatment that covers the two major causes of non-insulin dependent diabetes mellitus (NIDDM, type II diabetes), i.e. peripheral insulin resistance and beta cell dysfunction.

Thus, methods of identifying an agent which modulates insulin signaling can include contacting a cell with a test agent and determining if that test agent results in an increase or decreases in IR-B expression. The identification of an agent that increases IR-B expression is indicative that the agent can be useful in treating type II diabetes.

H. Kits

Kits for detecting the presence of IR-A or IR-B in a biological sample may comprise an IR-A and/or IR-B probe or primer. Materials for use in the methods described herein are ideally suited for preparation of kits. For example, the kit can comprise nucleic acid sequences as disclosed herein that are capable of detecting IR-A or IR-B in a tumor sample; a control sample; and instructions relating to how to detect the cell surface receptor. Such a kit may comprise containers, each with one or more of the various reagents (typically in concentrated form) utilized in the methods, including, for example, buffers, the appropriate nucleotide triphosphates (e.g., dATP, dCTP, dGTP and dTTP; or rATP, rCTP, rGTP and UTP), reverse transcriptase, DNA polymerase, RNA polymerase, and one or more oligonucleotides.

Oligonucleotides in containers can be in any form, e.g., lyophilized, or in solution (e.g., a distilled water or buffered solution), etc. Oligonucleotides ready for use in the same amplification reaction can be combined in a single container or can be in separate containers. The kit optionally further comprises in a separate container an RNA polymerase specific to the RNA polymerase promoter, and/or a buffer for PCR, and/or a DNA polymerase. The kit optionally further comprises a control nucleic acid. A set of instructions will also typically be included.

The methods disclosed herein employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, Molecular Cloning: A Laboratory Manual, Second Edition, Books 1-3, Cold Spring Harbor Laboratory Press; Ausubel, F. M. et al. (1995 and periodic supplements; Current Protocols in Molecular Biology, ch. 9, 13, and 16, John Wiley & Sons, New York, N.Y.); B. Roe, J. Crabtree, and A. Kahn, 1996, DNA Isolation and Sequencing: Essential Techniques, John Wiley & Sons; M. J. Gait (Editor), 1984, Oligonucleotide Synthesis: A Practical Approach, Irl Press; and, D. M. J. Lilley and J. E. Dahlberg, 1992, Methods of Enzymology: DNA Structure Part A: Synthesis and Physical Analysis of DNA Methods in Enzymology, Academic Press. Each of these general texts is herein incorporated by reference in their entireties.

The following examples are meant to serve to assist one of ordinary skill in the art in carrying out the methods described herein and are not intended in any way to limit the scope of the disclosure.

I. Exemplary Embodiments

The following list of embodiments is exemplary, and in no way limits the scope of the disclosure.

1. A synthetic nucleic acid comprising 10-30 consecutive nucleotides, wherein the synthetic nucleic acid sequence comprises at least 10-20 consecutive nucleotides of any one of the following sequences:

(i) SEQ ID NO: 3, a sequence complementary thereto, or a sequence that is capable of hybridizing to SEQ ID NO:3, or its complement, under stringent conditions;
(ii) SEQ ID NO: 4, a sequence complementary thereto (SEQ ID NO: 21), or a sequence that is capable of hybridizing to SEQ ID NO:4, or its complement, under stringent conditions;
(iii) SEQ ID NO: 5, a sequence complementary thereto, or a sequence that is capable of hybridizing to SEQ ID NO:5, or its complement, under stringent conditions; or
(iv) SEQ ID NO: 6, a sequence complementary thereto (SEQ ID NO: 22), or a sequence that is capable of hybridizing to SEQ ID NO:6, or its complement, under stringent conditions.

2. A synthetic nucleic acid sequence consisting essentially of any one of the following nucleic acid sequences:
(i) SEQ ID NO: 3, a sequence complementary thereto, or a sequence that is capable of hybridizing to SEQ ID NO:3, or its complement, under stringent conditions;
(ii) SEQ ID NO: 4, a sequence complementary thereto (SEQ ID NO: 21), or a sequence that is capable of hybridizing to SEQ ID NO:4, or its complement, under stringent conditions;
(iii) SEQ ID NO: 5, a sequence complementary thereto, or a sequence that is capable of hybridizing to SEQ ID NO:5 or its complement, under stringent conditions; or
(iv) SEQ ID NO: 6, a sequence complementary thereto (SEQ ID NO: 22), or a sequence that is capable of hybridizing to SEQ ID NO:6, or its complement, under stringent conditions.

3. A synthetic nucleic acid sequence consisting essentially of SEQ ID NO: 7, a sequence complementary thereto, or a sequence that is capable of hybridizing to SEQ ID NO:7, or its complement, under stringent conditions.

4. A synthetic nucleic acid sequence consisting essentially of SEQ ID NO: 8, a sequence complementary thereto, or a sequence that is capable of hybridizing to SEQ ID NO:8, or its complement, under stringent conditions.

5. A composition comprising the synthetic nucleic acid sequence of any one of embodiments 1-4.

6. A primer set for detecting and/or quantifying an IR-A nucleic acid sequence in a biological sample, wherein the primer set comprises
(a) a synthetic nucleic acid sequence comprising 10-30 consecutive nucleotides of the last 50 bases of exon 10 of the INSR gene (SEQ ID NO: 1), a sequence complementary thereto, or a sequence that is capable of hybridizing to SEQ ID NO:1, or its complement, under stringent conditions; and
(b) a synthetic nucleic acid sequence comprising 10-30 consecutive nucleotides of the first 60 bases of exon 12 of the INSR gene (SEQ ID NO: 2), a sequence complementary thereto, or a sequence that is capable of hybridizing to SEQ ID NO:2, or its complement, under stringent conditions.

7. The primer set of embodiment 6, wherein the at least one synthetic nucleic acid sequence has a nucleotide sequence chosen from among
SEQ ID NO: 3, a sequence complementary thereto, or a sequence that is capable of hybridizing to SEQ ID NO:3, or its complement, under stringent conditions;
SEQ ID NO: 21, a sequence complementary thereto, or a sequence that is capable of hybridizing to SEQ ID NO:21, or its complement, under stringent conditions;
SEQ ID NO: 5, a sequence complementary thereto, or a sequence that is capable of hybridizing to SEQ ID NO:5, or its complement, under stringent conditions; and
SEQ ID NO: 22, a sequence complementary thereto, or a sequence that is capable of hybridizing to SEQ ID NO:22, or its complement, under stringent conditions.

8. A method for detecting and/or quantifying an IR-A nucleic acid sequence in a biological sample, comprising the steps of:
(a) contacting a biological sample or nucleic acids prepared from a biological sample with the primer set of embodiment 6 under conditions suitable for polymerase-based amplification; and
(b) detecting and/or quantifying amplified target IR-A nucleic acid sequence.

9. The method of embodiment 8, wherein the biological sample is prepared from a tumor sample.

10. The method of any one of the embodiments 8-9, wherein the primer set comprises SEQ ID NO: 3, a sequence complementary thereto, or a sequence that is capable of hybridizing to SEQ ID NO:3, or its complement, under stringent conditions, and SEQ ID NO: 21, a sequence complementary thereto, or a sequence that is capable of hybridizing to SEQ ID NO:21, or its complement, under stringent conditions.

11. The method of embodiment 8, wherein the primer set comprises SEQ ID NO: 5, a sequence complementary thereto, or a sequence that is capable of hybridizing to SEQ ID NO:5, or its complement, under stringent conditions, and SEQ ID NO: 22, a sequence complementary thereto, or a sequence that is capable of hybridizing to SEQ ID NO:22, or its complement, under stringent conditions.

12. The method of any of embodiments 8-11, wherein said polymerase-based amplification is quantitative polymerase chain reaction.

13. The method of embodiment 12, wherein the primer set comprises:
SEQ ID NO: 3, a sequence complementary thereto, or a sequence that is capable of hybridizing to SEQ ID NO:3, or its complement, under stringent conditions;
SEQ ID NO: 21, a sequence complementary thereto, or a sequence that is capable of hybridizing to SEQ ID NO:21, or its complement, under stringent conditions; and
SEQ ID NO: 7, a sequence complementary thereto, or a sequence that is capable of hybridizing to SEQ ID NO:7, or its complement, under stringent conditions, which also has a detectable label.

14. The method of embodiment 12, wherein the primer set comprises:
SEQ ID NO: 5, a sequence complementary thereto, or a sequence that is capable of hybridizing to SEQ ID NO:5, or its complement, under stringent conditions;
SEQ ID NO: 22, a sequence complementary thereto, or a sequence that is capable of hybridizing to SEQ ID NO:22, or its complement, under stringent conditions; and
SEQ ID NO: 8, a sequence complementary thereto, or a sequence that is capable of hybridizing to SEQ ID NO:8, or its complement, under stringent conditions, which also has a detectable label.

15. The method of any of embodiments 8-14, wherein the amplified product is less than 100 bases.

16. A synthetic nucleic acid comprising 10-30 consecutive nucleotides, wherein the synthetic nucleic acid sequence comprises at least 10-20 consecutive nucleotides of any one of the following sequences:

(i) SEQ ID NO: 11, a sequence complementary thereto, or a sequence that is capable of hybridizing to SEQ ID NO:11, or its complement, under stringent conditions; or (ii) SEQ ID NO: 12, a sequence complementary thereto, or a sequence that is capable of hybridizing to SEQ ID NO:12, or its complement, under stringent conditions.

17. A synthetic nucleic acid consisting essentially of any one of the following nucleic acid sequences:
   (i) SEQ ID NO: 11, a sequence complementary thereto, or a sequence that is capable of hybridizing to SEQ ID NO:11, or its complement, under stringent conditions; or
   (ii) SEQ ID NO: 12, a sequence complementary thereto, or a sequence that is capable of hybridizing to SEQ ID NO:12, or its complement, under stringent conditions.

18. A synthetic nucleic acid sequence consisting essentially of SEQ ID NO: 13, a sequence complementary thereto, or a sequence that is capable of hybridizing to SEQ ID NO:13, or its complement, under stringent conditions.

19. A synthetic nucleic acid sequence consisting essentially of SEQ ID NO: 14, a sequence complementary thereto, or a sequence that is capable of hybridizing to SEQ ID NO:14, or its complement, under stringent conditions.

20. A synthetic nucleic acid sequence consisting essentially of SEQ ID NO: 15, a sequence complementary thereto, or a sequence that is capable of hybridizing to SEQ ID NO:15, or its complement, under stringent conditions.

21. A composition comprising the synthetic nucleic acid sequence of any one of embodiments 1-4 and 16-20.

22. A primer set for detecting and/or quantifying an IR-B nucleic acid sequence in a biological sample, wherein the primer set comprises:
   (a)(i) a synthetic nucleic acid sequence comprising 10-30 consecutive nucleotides of the last 50 bases of exon 10 of the INSR gene (SEQ ID NO: 1), a sequence complementary thereto, or a sequence that is capable of hybridizing to SEQ ID NO:1, or its complement, under stringent conditions,
   (a)(ii) a synthetic nucleic acid sequence comprising 10-30 consecutive nucleotides of exon 11 of the INSR gene (SEQ ID NO: 9), a sequence complementary thereto, or a sequence that is capable of hybridizing to SEQ ID NO:9, or its complement, under stringent conditions; or
   (a)(iii) a synthetic nucleic acid sequence comprising 10-30 consecutive nucleotides of the bases bridging exons 10 and 11, a sequence complementary thereto, or a sequence that is capable of hybridizing thereto, or its complement, under stringent conditions; and
   (b) a synthetic nucleic acid sequence comprising 10-30 consecutive nucleotides of the first 50 bases of exon 12 of the INSR gene (SEQ ID NO: 10), a sequence complementary thereto, or a sequence that is capable of hybridizing to SEQ ID NO:10, or its complement, under stringent conditions or a sequence complementary thereto.

23. The primer set of embodiment 22, wherein the at least one synthetic nucleic acid sequence has a nucleotide sequence chosen from among
   SEQ ID NO: 11, a sequence complementary thereto, or a sequence that is capable of hybridizing to SEQ ID NO:11, or its complement, under stringent conditions; and
   SEQ ID NO: 12, a sequence complementary thereto, or a sequence that is capable of hybridizing to SEQ ID NO:12, or its complement, under stringent conditions.

24. A method for detecting and/or quantifying a IR-B nucleic acid in a biological sample, comprising the steps of:
   (a) contacting a biological sample, or nucleic acids prepared from a biological sample, with the primer set of embodiment 22 or 23 under conditions suitable for polymerase-based amplification; and
   (b) detecting and/or quantifying amplified target IR-B nucleic acid sequence.

25. The method of embodiment 24, wherein the biological sample is a tumor sample.

24. The method of embodiment 24, wherein the primer set comprises:
   SEQ ID NO: 11, a sequence complementary thereto, or a sequence that is capable of hybridizing to SEQ ID NO:11, or its complement, under stringent conditions; and
   SEQ ID NO: 12, a sequence complementary thereto, or a sequence that is capable of hybridizing to SEQ ID NO:12, or its complement, under stringent conditions.

25. The method of embodiment 24, wherein said polymerase-based amplification is quantitative polymerase chain reaction (q-PCR).

26. The method of embodiment 25, wherein the primer set comprises:
   SEQ ID NO: 11, a sequence complementary thereto, or a sequence that is capable of hybridizing to SEQ ID NO:11, or its complement, under stringent conditions;
   SEQ ID NO: 12, a sequence complementary thereto, or a sequence that is capable of hybridizing to SEQ ID NO:12, or its complement, under stringent conditions; and
   SEQ ID NO: 13, a sequence complementary thereto, or a sequence that is capable of hybridizing to SEQ ID NO:13, or its complement, under stringent conditions which also has a detectable label.

27. The method of embodiment 25, wherein the primer set comprises:
   SEQ ID NO: 11, a sequence complementary thereto, or a sequence that is capable of hybridizing to SEQ ID NO:11, or its complement, under stringent conditions;
   SEQ ID NO: 12, a sequence complementary thereto, or a sequence that is capable of hybridizing to SEQ ID NO:12, or its complement, under stringent conditions; and
   SEQ ID NO: 14, a sequence complementary thereto, or a sequence that is capable of hybridizing to SEQ ID NO:14, or its complement, under stringent conditions which also has a detectable label.

28. The method of embodiment 25, wherein the primer set comprises:
   SEQ ID NO: 11, a sequence complementary thereto, or a sequence that is capable of hybridizing to SEQ ID NO:11, or its complement, under stringent conditions;
   SEQ ID NO: 12, a sequence complementary thereto, or a sequence that is capable of hybridizing to SEQ ID NO:12, or its complement, under stringent conditions; and further comprises
   SEQ ID NO: 15, a sequence complementary thereto, or a sequence that is capable of hybridizing to SEQ ID NO:15, or its complement, under stringent conditions, which also has a detectable label.

29. The method of any of embodiments 24-28, wherein the amplified product is less than 100 bases.

30. A method for determining the presence or absence of a target IR-A nucleic acid sequence and/or a target IR-B nucleic acid sequence in a biological sample, comprising:
   contacting a biological sample, or a sample of nucleic acids prepared from a biological sample, with a primer set for detecting and/or quantifying an IR-A nucleic acid sequence in a biological sample under conditions suitable for polymerase-based amplification, wherein the primer set comprises the primer set of embodiment 6 and/or contacting a biological sample, or a sample of nucleic acids prepared from a biological sample, with a primer set for detecting and/or quantifying an IR-B nucleic acid sequence in a biological sample under conditions suitable for polymerase-based amplification, wherein the primer set comprises the primer set of embodiment the primer set of embodiment 22, and detecting and/or quantifying amplified target IR-A or IR-B nucleic acid sequence.

31. A kit for determining the presence or absence of IR-A in a biological sample comprising at least one synthetic nucleic acid sequence of any of embodiments 1-15 and instructions for use.

32. The kit of embodiment 31, wherein the at least one synthetic nucleic acid sequence has a nucleotide sequence chosen from among SEQ ID NO:3, SEQ ID NO:4, SEQ ID NO:5, SEQ ID NO:6, a sequence complementary to one of said sequences, or a sequence that is capable of hybridizing to one of said sequences, or its complement, under stringent conditions.

33. The kit of embodiment 31, wherein the synthetic nucleic acid sequence is chosen from among the following primer sets:

(1) SEQ ID NO: 3, a sequence complementary thereto, or a sequence that is capable of hybridizing to SEQ ID NO:3, or its complement, under stringent conditions;

SEQ ID NO: 21, a sequence complementary thereto, or a sequence that is capable of hybridizing to SEQ ID NO:21, or its complement, under stringent conditions; and SEQ ID NO: 7, a sequence complementary thereto, or a sequence that is capable of hybridizing to SEQ ID NO:7, or its complement, under stringent conditions, which also has a detectable label; or (2) SEQ ID NO: 5, a sequence complementary thereto, or a sequence that is capable of hybridizing to SEQ ID NO:5, or its complement, under stringent conditions;

SEQ ID NO: 22 a sequence complementary thereto, or a sequence that is capable of hybridizing to SEQ ID NO:22, or its complement, under stringent conditions; and SEQ ID NO: 8, a sequence complementary thereto, or a sequence that is capable of hybridizing to SEQ ID NO:8, or its complement, under stringent conditions, which also has a detectable label.

34. The kit of embodiment 31, further comprising suitable PCR reagents; and optionally, a positive and/or negative control for determining the presence or absence of IR-A.

35. A kit for determining the presence or absence of IR-B in a biological sample comprising at least one synthetic nucleic acid sequence of any of embodiments 16-23 and instructions for use.

36. The kit of embodiment 35, wherein the synthetic nucleic acid sequence has a nucleotide sequence chosen from among SEQ ID NO:11, SEQ ID NO:12, a sequence complementary to any of said sequences, or a sequence that is capable of hybridizing to any of said sequences, or its complement, under stringent conditions.

37. The kit of embodiment 35, wherein the synthetic nucleic acid sequence is chosen from the following primer sets:

(1) SEQ ID NO: 11, a sequence complementary thereto, or a sequence that is capable of hybridizing to SEQ ID NO:11, or its complement, under stringent conditions;

SEQ ID NO: 12, a sequence complementary thereto, or a sequence that is capable of hybridizing to SEQ ID NO:12, or its complement, under stringent conditions; and SEQ ID NO: 13, a sequence complementary thereto, or a sequence that is capable of hybridizing to SEQ ID NO:13, or its complement, under stringent conditions having a detectable label;

(2) SEQ ID NO: 11, a sequence complementary thereto, or a sequence that is capable of hybridizing to SEQ ID NO:11, or its complement, under stringent conditions;

SEQ ID NO: 12, a sequence complementary thereto, or a sequence that is capable of hybridizing to SEQ ID NO:12, or its complement, under stringent conditions; and SEQ ID NO: 14 having a detectable label; or (3) SEQ ID NO: 11, a sequence complementary thereto, or a sequence that is capable of hybridizing to SEQ ID NO:11, or its complement, under stringent conditions;

SEQ ID NO: 12, a sequence complementary thereto, or a sequence that is capable of hybridizing to SEQ ID NO:12, or its complement, under stringent conditions; and SEQ ID NO: 15, a sequence complementary thereto, or a sequence that is capable of hybridizing to SEQ ID NO:15, or its complement, under stringent conditions, which also has a detectable label.

38. The kit of embodiment 35, further comprising: suitable PCR reagents; and optionally, a positive and/or negative control for determining the presence or absence of IR-B.

39. A method for selecting a patient responsive to an IGFI/II ligand or IGFR1 receptor antagonist, the method comprising:

detecting and/or quantifying IR-A expression in a sample according to embodiment 8 detecting and/or quantifying IR-B expression in a sample according to embodiment 24; and wherein the expression of IR-A and IR-B is an indication of whether an IGFI/II ligand or IGF1R receptor antagonist should be administered to the subject.

40. The method of embodiment 39, wherein the IGFI/II ligand or IGFR1 receptor antagonist is an antibody.

41. The method of embodiment 40, wherein the antibody comprises sequence components listed in Table 1 and Table 2.

42. A method for determining the relative presence or absence of a target IR-A nucleic acid sequence and a target IR-B nucleic acid sequence in a biological sample, comprising:

contacting a biological sample or nucleic acids prepared from a biological sample, under conditions suitable for polymerase-based amplification, with the primer set of embodiment 6, contacting a biological sample or nucleic acids prepared from a biological sample, under conditions suitable for polymerase-based amplification, with a primer set of embodiment 22;

quantifying amplified IR-A and IR-B nucleic acid sequence; and thereby determining a relative expression of IR-A versus IR-B in the biological sample.

43. A method of classifying a tumor comprising determining a relative expression of IR-A versus IR-B in a sample of the tumor by the method of embodiment 42, classifying the tumor by criteria comprising the relative expression of IR-A and IR-B.

44. A method of selecting a patient for treatment with an IGF antagonist comprising
    determining a relative expression of IR-A versus IR-B in a tissue of the patient by the method of embodiment 42,
    classifying the patient by criteria comprising the relative expression of IR-A and IR-B thereby predicating the relative responsiveness of the patient to an IGF antagonist.

45. The method of any of embodiments 39, 43 and 44, wherein the expression of IR-A is increased relative to IR-B.

46. A method of treating a patient using an IGF antagonist comprising
    determining a relative expression of IR-A versus IR-B in the tissue sample by the method of embodiment 42,
    classifying the patient by criteria comprising the relative expression of IR-A and IR-B; and,
    administering an IGF antagonist in accordance with the classification.

47. The method of embodiment 46, wherein the expression of IR-A is increased relative to IR-B.

48. The method of any of embodiments 44 or 47, wherein the IGF antagonist is an antibody.

49. The method of any of embodiments 40, 41, and 48, wherein the antibody comprises an amino acid sequence comprising the amino acid sequences of SEQ ID NOs: 45 and 53.

50. The method of any of embodiments 40, 41, and 48, wherein the antibody comprises the CDR sequences of SEQ ID NOs: 45 and 53, as shown in Tables 1 and 2.

51. The method of any of embodiments 40, 41, and 48, wherein, the antibody comprises three CDRs from SEQ ID NO: 45 and a light chain.

52. The method of any of embodiments 40, 41, and 48, wherein the antibody comprises three CDRs from SEQ ID NO: 53 and a heavy chain.

53. The method of any of embodiments 45 and 47, wherein the percentage of IR-A relative total insulin receptor is greater than 46.6%.

54. The method of any of embodiments 45 and 47, wherein the IRA:IR-B ΔΔCt is less than about 0.2.

55. The method of any of embodiments 45 and 47, wherein the mean relative quantity differentials on a log 2-base scale for IR-A is about –0.07±0.29 is about –2.08±0.25 for IR-B.

56. A method of classifying a breast cancer tumor subtype, the method comprising determining a relative expression of IR-A versus IR-B in a breast cancer tumor sample by the method of embodiment 42; and, classifying the breast cancer subtype as luminal B if the IR-A:IR-B ratio is lower than a threshold value.

57. The method of embodiment 56 further comprising calculating IR-A:IR-B ΔΔCt, wherein the threshold is a IR-A:IR-B ΔΔCt value set in the range between about –1.1 to about –2.4.

58. The method of embodiment 54, wherein the threshold is in the range between about –1.4 to –2.1.

59. The method of embodiment 57, wherein a determination of IR-A:IR-B ΔΔCt may be combined with other expression profiles in determining subtype classifications.

60. A method of determining a proliferation score for a tumor, the method comprising determining a relative expression of IR-A versus IR-B in a tumor sample by the method of embodiment 42, and considering a higher IR-A:IR-B ratio as a factor indicating a higher proliferation score.

61. The method of embodiment 60, further comprising calculating IR-A:IR-B ΔΔCt and considering a lower IR-A:IR-B ΔΔCt value as a factor indicating a higher proliferation score.

62. A method of classifying a breast cancer sample as luminal-A or luminal-B, comprising determining the relative levels of IR-A and IR-B in the sample, wherein an increased amount of IR-A relative to IR-B indicates a tumor that is luminal-B.

EXAMPLES

Example 1

IR-A and IR-B Primer and Probe Design

Commercially purchased assays were unable to distinguish and quantify IR-A and IR-B expression. Thus, novel probes were required. Mature mRNA transcript sequences for the insulin receptor (INSR) short (NM 001079817) and long (NM 000208) isoforms were obtained from the National Center for Biotechnology Information (NCBI) Entrez Nucleotide database. The INSR short isoform is designated as IR-A and the INSR long isoform as IR-B. The difference between the two isoforms is the presence (in IR-B) or absence (in IR-A) of exon 11, a 36 nucleotide region, in the mature transcript. Exon 11 is absent in the IR-A form, while the IR-B form contains the exon 11 sequence in the mature mRNA transcript. For the design of primers and probes that are specific for the detection of IR-A mRNA, the exon 10/12 junction region was targeted for the gene specific probe. Several primer pairs (forward and reverse) located within the exon 10 or exon 12 coding regions, respectively, were designed. For the IR-B design, the exon 11/12 junction was targeted and the exon 11 interior region for the gene specific probe. Several primer pairs (forward and reverse) located within exon 10 or on the exon 10/11 junction and exon 12 coding regions, respectively, were designed. All primer/probe designs were imported into the Primer Express (ABI) software tool to ensure optimal design for utilization in the TaqMan Gene Expression assay procedure. All probes were designed to incorporate a minor groove binding (MGB) moiety, and were labeled with a fluorescent dye (FAM) for detection and a non-fluorescent quencher. Sequences for all primer/probe combinations designed are presented Tables 3 and 4.

TABLE 3

Primer and Probes of IR-A assay.
IR-A Primer Probe Designs:

| Name | Forward Primer (5'-->3') | Reverse Primer (5'-->3') | Probe (FAM-MGB) (5'-->3') |
|---|---|---|---|
| IRA | CAGGCCATCTCGG AAACG SEQ ID NO: 16 | ACGGCCACCGTCAC ATTC SEQ ID NO: 20 | AGGTCCCTTGGCGATG SEQ ID NO: 24 |
| IRA1 | TGAGGATTACCTG CACAACG SEQ ID NO: 3 | ACCGTCACATTCCC AACATC SEQ ID NO: 21 | TCCCCAGGCCATCT SEQ ID NO: 7 |
| IRA2 | CTGGTGCCGAGGA CCCTAGG SEQ ID NO: 17 | ACCGTCACATTCCC AACATC SEQ ID NO: 21 | TCCCCAGGCCATCT SEQ ID NO: 7 |
| IRA3 | TTGAGGATTACCT GCACAACGT SEQ ID NO: 5 | GCCAAGGGACCTGC GTTT SEQ ID NO: 22 | TTTTCGTCCCCAG GCCA SEQ ID NO:8 |
| IRA4 | CTGCACAACGTGG TTTTCGT SEQ ID NO: 18 | CACCGTCACATTCC CAACATC SEQ ID NO: 23 | CAGGCCATCTCGGAAA SEQ ID NO:25 |

TABLE 3-continued

Primer and Probes of IR-A assay.
IR-A Primer Probe Designs:

| Name | Forward Primer (5'-->3') | Reverse Primer (5'-->3') | Probe (FAM-MGB) (5'-->3') |
|---|---|---|---|
| IRA5 | TTGAGGATTACCT GCACAACGT SEQ ID NO: 19 | GCCAAGGGACCTGC GTTT SEQ ID NO: 22 | TTCGTCCCCAGGCCA SEQ ID NO: 26 |

TABLE 4

Primer and Probes of IR-B assay.
IR-B Primer Probe Designs:

| Name | Forward Primer (5'-->3') | Reverse Primer (5'-->3') | Probe (FAM-MGB) (5'-->3') |
|---|---|---|---|
| IRB | ACCCTAGGCCATC TCGGAAA SEQ ID NO: 27 | CACGGCCACCGTCA CATT SEQ ID NO: 28 | CCTTGGCGATGTTGG SEQ ID NO: 29 |
| IRB1 | TGAGGATTACCTG CACAACG SEQ ID NO: 3 | ACCGTCACATTCCC AACATC SEQ ID NO: 21 | GAGGACCCTAGGCCA SEQ ID NO: 30 |
| IRB2 | CTGGTGCCGAGGA CCCTAGG SEQ ID NO: 17 | ACCGTCACATTCCC AACATC SEQ ID NO: 21 | TGCCGAGGACCCTA SEQ ID NO: 31 |
| IRB3 | CGTCCCCAGAAAA ACCTCTTC SEQ ID NO: 11 | GGACCTGCGTTTCC GAGAT SEQ ID NO: 12 | ACTGGTGCCGAGGAC SEQ ID NO: 13 |
| IRB4 | CGTCCCCAGAAAA ACCTCTTC SEQ ID NO: 11 | GGACCTGCGTTTCC GAGAT SEQ ID NO: 12 | CCGAGGACCCTAGGC SEQ ID NO: 14 |
| IRB5 | CGTCCCCAGAAAA ACCTCTTC SEQ ID NO: 11 | GGACCTGCGTTTCC GAGAT SEQ ID NO: 12 | TGCCGAGGACCCTAG SEQ ID NO: 15 |

Example 2

Specificity of the Primers and Probes

Commercially available plasmids containing full length cDNA clones for the INSR long (clone SC311328) and short (clone SC315880) transcripts were purchased from OriGene Technologies, Inc. Sequence verification of each INSR clone was conducted. All TaqMan Gene Expression assay designs were tested for specificity and sensitivity in the presence of either the INSR long or short isoform clones at various copy number inputs (102-107 copies). Standard TaqMan Gene Expression assays were conducted in a 384-well format for all primer/probe and template combinations. Reactions consisted of 7.5 μL of TaqMan Universal Master Mix, 1.5 μL of 10× Gene Expression Assay Mix, and 6 μL of varying copy numbers of either the INSR long or short form cDNA clone, for a final volume of 15 μL per well of a 384-well plate. Each primer/probe and template combination was repeated at least 3 times. All assay plates were run on an Applied Biosystems 7900HT detection system using standard settings (cycling program consisting of a 10 min incubation at 95 C followed by 40 cycles of 95° C. for 15 sec and 60° C. for 1 min). Data values (Ct values) were extracted from each assay run with the SDS v2.0 software tool (ABI). Following data extraction and analysis, it was determined that the following primer and probe assay designs provided sufficient sensitivity and specificity for our purposes; IR-A1, IR-A3, IR-B3, IR-B4, and IR-B5.

The IR-A1 and IR-A3 assays were able to detect the IR-A isoform sequence at a copy number threshold of about 35 copies. These assays were also determined to be highly specific for IR-A isoform since they were unable to detect the presence of IR-B isoform at any copy number input utilized. Alternatively, the IR-B3, IR-B4, and IR-B5 designs were able to detect IR-B isoform sequence at a copy number threshold of about 35 copies. These designs were also determined to be specific for IR-B isoform since they were unable to detect the presence of IR-A isoform below a threshold of about 35 copies and they were unable to detect the presence of IR-B isoform at any copy number input utilized.

These specificity experiments were repeated utilizing the BioMark™ Dynamic Array (Fluidigm Corporation) microfluidics system for Real-Time PCR. This system allows for high throughput real-time PCR (2304 individual reactions possible per plate), producing high quality data with low variability and a tight correlation with conventional RT-PCR. To employ this technology, cDNA samples were pre-amplified using TaqMan Pre-Amp Master Mix, according to the manufacturer's instructions. Reactions contained 5 μL of cDNA, 10 μL Pre-Amp Master Mix, and 5 μL of 0.2× gene expression assay mix (comprised of all primer/probes to be assayed) for a final volume of 20 pt. Reactions were cycled with the recommended program for 14 cycles and then diluted 1:5 with TE buffer. Pre-amplified cDNA was either utilized immediately or stored at −20 C until needed.

To prepare samples for loading into 48×48 dynamic array chips (Fluidigm), the reaction mix contained 2.5 μL 2× Universal Master Mix (Applied Biosystems), 0.25 μL Sample Loading Buffer (Fluidigm Corporation), and 2.25 μL pre-amplified cDNA. To prepare the primer/probes, the reaction mix contained 2.5 μL 20× Taqman Gene Expression Assay and 2.5 μL Assay Loading Buffer (Fluidigm Corporation). Prior to loading the samples and assay reagents into the inlets, the chip was primed in the IFC Controller. Five μL of sample prepared as described was loaded into each sample inlet of the dynamic array chip and 5 μL of 10× gene expression assay mix was loaded into each detector inlet. The chip was placed on the IFC Controller for loading and mixing. After approximately 1 hr, the chip was loaded on the BioMark™ Real-Time PCR System for thermal cycling (10 min at 95° C. followed by 40 cycles of 95° C. for 15 sec and 1 min at 60° C.). The number of replicates and the composition of the samples varied depending on the particular experiment, but were never less than triplicate. Average Ct values were used to determine sensitivity and specificity of the designed probes.

The results obtained using conventional real-time PCR were confirmed using the Fluidigm system. IR-A1, IR-A3, IR-B3, IR-B4, and IR-B5 were specific for either IR-A or IR-B and were able to detect the appropriate receptor isoform at a copy number threshold of about 35 copies.

Additional analyses also utilized cDNA template from cell lines either known to over-express either IR-A or IR-B or engineered to over-express IR-A. Delta comparative threshold (ΔCt) values for each sample were calculated by subtracting the average CT of the 2 endogenous control genes (GAPDH and ACTIN) from the average Ct of the target gene. Results indicated that these primer/probe designs reproducibly and specifically detected either IR-A or IR-B in cell lines in the same manner observed using cDNA clones. Together, these results validate the use of Fluidigm technology for further high throughput analysis of cDNA or tissue samples, as well as confirming the specificity of the IR-A and IR-B primer/probe designs. Following qualification of multiple primer/probe designs, we selected IR-A1 and IR-B4 to measure the expression status of IR-A and IR-B in a large set of breast cancers.

Figure 7:
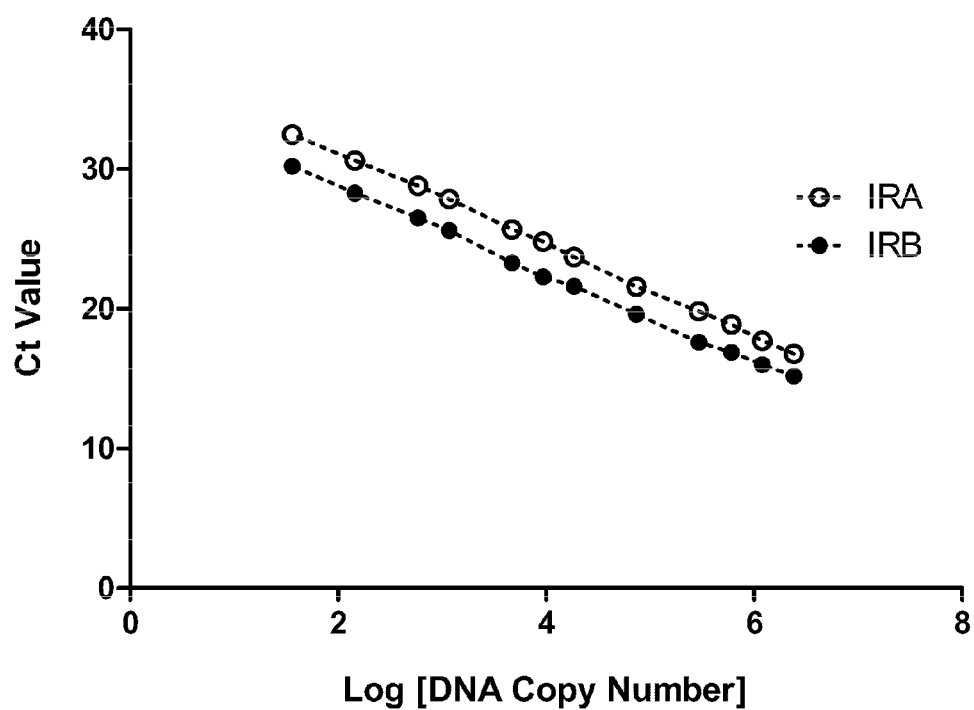
FIG. 7 shows results of IR-A or IR-B qRT-PCR assays with a serial dilution of approximately $10^7$ to 10 copies of plasmid DNA of either IR-A, IR-B, or an empty vector control. The Y axis represents cycle-threshold (Ct) values and the X axis represents log DNA copy number. The slope and correlation coefficient ($r^2$ value) of the standard dilution curve for the IR-A assay are −3.259 and 0.9992, respectively. The slope and correlation coefficient ($r^2$ value) of the standard dilution curve for the IR-B assay are −3.155 and 0.9989, respectively.

Probe sensitivity was confirmed by performing an IR-A or IR-B qRT-PCR assay starting with 100 pg template stock solutions of IR-A or IR-B (approximately $10^7$ copies of DNA template). The DNA was serially diluted to $10^{-4}$ pg (approximately 10 copies DNA template). Each sample was tested in duplicate. The slope of the standard template dilution curve was determined by plotting cycle-threshold (Ct) values as a function of the log DNA copy number. The results are shown in FIG. 7. Strong correlations were observed between the log [concentration] and resultant Ct values for each assay tested with its respective matching standard template. All correlation coefficients ($r^2$ value) were ≥0.999 (p≤0.0001). Linearities were maintained in the DNA concentration ranges described above in both assays, demonstrating a wide dynamic range and yielding accurate Ct values. The results indicated that both the IR-A and IR-B assays are sensitively detecting the appropriate isoform to ~35 copies of DNA.

The specificities of the assays were also assessed by testing the IR-A assay in the presence of the IR-B DNA template or the IR-B assay in presence of the IR-A DNA template, respectively. The IR-A assay does not amplify IR-B DNA template in the tested range of 10 to $10^7$ copies of IR-B DNA. Likewise, the IR-B assay does not amplify the IR-A DNA template in the range tested.

The assay efficiency was assessed by the slopes of the standard dilution curves for both assays (FIG. 7). The slope is −3.259 for IR-A and −3.155 for IR-B. The two slopes are very similar, suggesting little differences in probe efficiency.

Example 3

Expression Profiling in Breast Cancer Patients

A. General Methodology

Forty-two grade I to III infiltrating breast ductal carcinomas were purchased from ILSbio (Chestertown, Md.). 19 matched normal adjacent breast tissue samples were also procured. The ages of patients ranged from 31 to 88 years. All the breast cancer samples are ER and PR positive and HER2 negative according IHC. All samples were fresh frozen and collected before initiation of any treatment. Tumor samples were macrodissected to remove normal tissue and the normal samples were macrodissected to remove non-glandular tissue. After macrodissection, the tumor purity in all samples is greater than 85%.

Four breast cancer tissue qPCR cDNA arrays (BCRT101, BCRT102, BCRT103, BCRT104) were purchased from OriGene Technologies (Rockville, Md.). The qPCR arrays contain cDNAs from 15 normal breast tissues (from 10 unique donors) and 165 breast adenocarcinoma tissues. The tumor stage varied from stage I to IV and the tissues were comprised of 50-90% tumor.

Total RNA was extracted from snap-frozen tissue specimens using the ZR RNA MicroPrep kit (Zymo Research, Orange, Calif.). RNA purity and concentration were determined spectrophotometrically (260/280>1.9). RNA quality was assessed on an Agilent 2100 Bioanalyzer using the RNA 6000 Nano LabChip®.

For the following examples, the sequence of the forward primer for IR-A assay was 5'-TGAGGATTACCTGCACAACG-3' (SEQ ID NO: 3), and the sequence of the reverse primer is 5'-ACCGTCACATTCCCAACATC-3' (complement of SEQ ID NO:4), and the probe 5'-TCCCCAGGCCATCT-3' (SEQ ID NO:7). The sequence of the forward primer for the IR-B assay was 5'-CGTCCCCAGAAAAACCTCTTC-3' (SEQ ID NO:11), and the sequence of reverse primer is 5'-GGACCTGCGTTTCCGAGAT-3' (SEQ ID NO:12), and the sequence of the probe is 5' CCGAGGACCCTAGGC-3' (SEQ ID NO:14).

For positive and negative controls, commercially available cDNA clones which contain the full-length cDNA clone of IR-A (cloned in pCMV6-XL4) and IR-B (cloned in pCMV6-XL5) were purchased from OriGene Technologies, Inc (IR-A: SKU#. SC311328; IR-B: SKU# SC315880). The empty plasmids of pCMV6-XL4 and pCMV6-XL5 were used as negative control DNA for IR-A and IR-B assays, respectively.

Standard TaqMan Gene Expression assays were conducted in a 384-well format for all primer/probe and template combinations. Reactions consisted of 5 µL of TaqMan Universal Master Mix, 0.5 µL of 10× Gene Expression Assay Mix, and 4.5 µL of varying copy numbers of either the IR-B or IR-A cDNA clone, for a final volume of 10 µL per well of a 384-well plate. Each primer/probe and template combination was repeated at least 3 times. All assay plates were run on an Applied Biosystems 7900HT detection system using standard settings (cycling program consisting of a 10 min incubation at 95° C. followed by 40 cycles of 95° C. for 15 sec and 60° C. for 1 min). Data values (Cycle Threshold (Ct) values) were extracted from each assay run with the SDS v2.0 software tool (ABI).

For assessment of the expression levels of other genes, TaqMan Gene Expression assays were purchased from ABI (Forest city, Calif.) The assays include: INSR (Assay ID: Hs00961554_m1), ER (Assay ID: Hs00174860_m1), PR (Assay ID: Hs01556707_m1), ERBB2 (HER2, Assay ID: Hs01001580_m1), tumor proliferation genes (Pike S et al 2004): BIRC5 (Assay ID:Hs00153353_m1), AURKA (STK15, Assay ID:Hs01582073_m1), CCNB1 (Assay ID: Hs00259126_m1), Ki67 (Assay ID: Hs01032443_m1), MYBL2 (Assay ID: Hs00942543_m1) and reference or "housekeeping" genes: ACTB (Hs99999903_m1), GUSB (AssyID:Hs99999908_m1), GAPDH (Assay ID: Hs99999905_m1), RPLPO (Assay ID: Hs99999902_m1), TFRC (Assay ID: Hs99999911_m1).

BioMark™ Dynamic Array (Fluidigm Corporation) microfluidics system allows for high throughput real-time PCR (2304 individual reactions possible per plate), producing high quality data with low variability and a tight correlation with conventional RT-PCR. Single stranded cDNA was generated from total RNA using the SuperScript® III First-Strand Synthesis SuperMix (Invitrogen, Carlsbad, Calif.). cDNA samples were pre-amplified using TaqMan Pre-Amp Master Mix, according to the manufacturer's instructions. Reactions contained 5 uL of cDNA, 10 uL Pre-Amp Master Mix, and 5 uL of 0.2× gene expression assay mix (comprised of all primer/probes to be assayed) for a final volume of 20 uL. Reactions were cycled with the recommended program for 14 cycles and then diluted 1:5 with TE buffer. Pre-amplified cDNA was either utilized immediately or stored at −20° C. until needed.

To prepare samples for loading into 48–48 dynamic array chips (Fluidigm), the reaction mix contained 2.5 uL 2× Universal Master Mix (Applied Biosystems), 0.25 uL Sample Loading Buffer (Fluidigm Corporation), and 2.25 uL pre-amplified cDNA. To prepare the primer/probes, the reaction mix contained 2.5 uL 20× Taqman Gene Expression Assay and 2.5 uL Assay Loading Buffer (Fluidigm Corporation). Prior to loading the samples and assay reagents into the inlets, the chip was primed in the IFC Controller. Five uL of sample prepared as described was loaded into each sample inlet of the dynamic array chip and 5 uL of 10× gene expression assay mix was loaded into each detector inlet. The chip was placed on the IFC Controller for loading and mixing. After approximately 1 hr, the chip was loaded on the BioMark™ Real-Time PCR System for thermal cycling (10 min at 95° C. followed by 40 cycles of 95° C. for 15 sec and 1 min at 60° C.). The number of replicates and the composition of the samples varied depending on the particular experiment, but were never less than triplicate. Average Ct values were used to determine sensitivity and specificity of the designed probes. The average Ct values of all available reference gene assays, within a sample, were used for ΔCt calculation.

Generation of biotin-labeled amplified cRNA from 75 ng of total RNA was accomplished with the MessageAmp™ Premier RNA Amplification Kit (Ambion, Austin, Tex.). The concentration and purity of the cRNA product were determined spectrophotometrically. Fifteen micrograms of each biotin-labeled cRNA was fragmented for hybridization on Affymetrix Human Genome U133 Plus 2.0 GeneChip® arrays. All GeneChip® washing, staining, and scanning procedures were performed with Affymetrix standard equipment. Data capture and initial array quality assessments were performed with the GeneChip Operating Software (GCOS) tool. Any probe displaying a signal intensity <25 across all samples was excluded from the analysis.

A subset of ER+, PR+ and Her2− primary breast tumors (n=40) and matched normal adjacent breast tissue samples (n=15) was profiled on Affymetrix Human Genome U133 Plus 2.0 GeneChip® arrays. Two of the primary breast samples and four of the matched normal adjacent breast tissue samples analyzed on the Fluidigm platform were not processed on GeneChip due to insufficient RNA quantity. Breast cancer molecular subtype classification, with regards to luminal-A and luminal-B subtype, was conducted utilizing our whole genome array data.

Two methods for determining putative sample classification were implemented. The first classification method utilized a published PAM50-gene shrunken centroid classifier (Weigelt, et al. 2010) for sample sub-typing (normal, basal-like, HER2, luminal-A, or luminal-B) purposes. MASS normalized GeneChip data was used for this analysis given that the published classifier was built using this type of scaled data. The samples were classified according to a Spearman's rank correlation (50-gene intensity vector vs. subtype centroid classifier), where the subtype with the highest correlation value was assigned to a particular sample. The second method utilized GC-RMA normalized GeneChip data to identify a panel of differentially expressed transcripts by a two-sample Welch's t-test analysis. Samples were divided into two groups (normal or tumor) based on pathology assessment prior to conducting the statistical analysis. Probes displaying a fold change differential >3 and p-value <$1.0 \times 10^{-12}$ (n=459 probes) were used for an unsupervised hierarchical clustering analysis. Sub-populations identified were classified as normal, luminal-A, or luminal-B as a function of transcript panel composition.

B. Results
IR-A and IR-B in Breast Cancer

Figure 8:
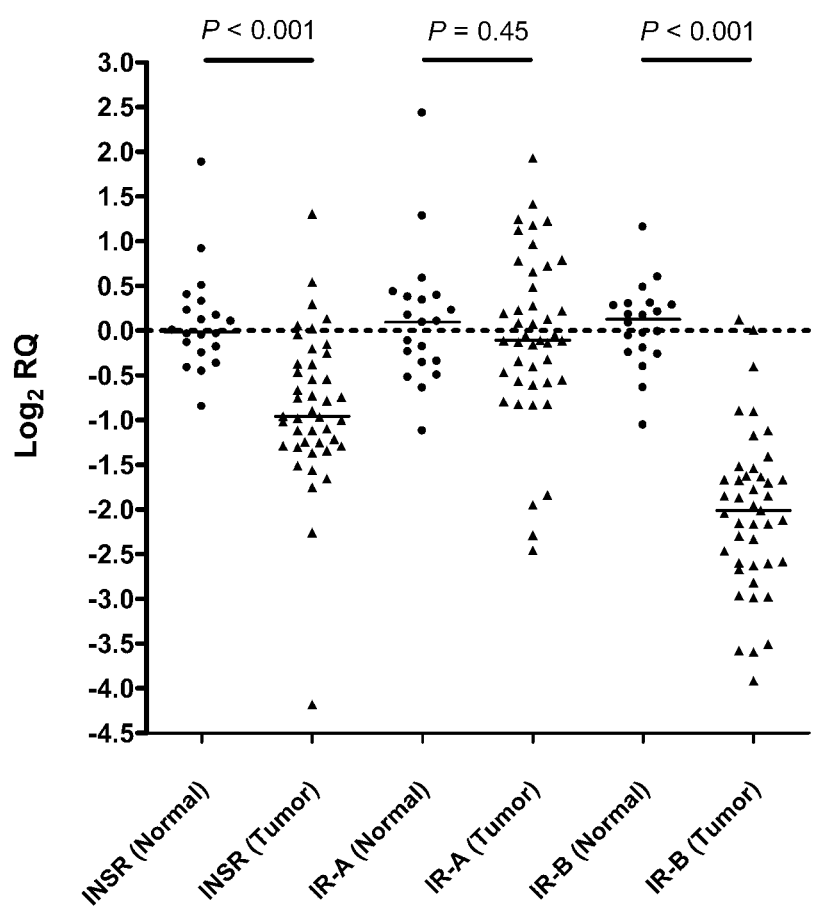
FIG. 8 shows relative mRNA expression levels of insulin receptor and its isoforms in primary breast cancer compared to normal breast tissues. TaqMan gene expression assay determined relative quantity (RQ) differentials ($\log_2$-base scale) of INSR (total), IR-A, and IR-B between normal (n=19) and tumor (n=42) breast tissue samples. Average normal ΔCt values were used for calculation of fold change differentials for each sample. A two-tailed Welch's t-test analysis identified a significant difference between normal and tumor samples for both INSR and IR-B (P<0.001), whereas no difference was observed for IR-A (P=0.45). Bars represent the median $\log_2$ RQ value within a particular gene target and tissue-type combination.

The mRNA expression status of IR-A and IR-B in breast cancer, 42 ER and PR positive and Her2 negative primary breast tissue samples and 19 matched normal adjacent breast tissues were studied. Random hexamer primed cDNAs were pre-amplified and assayed for expression levels of IR-A, IR-B, and total insulin receptor (INSR) transcripts by Taq-Man qPCR (Fluidigm). Samples were normalized to the average of five housekeeping genes as described above. The results are shown in FIG. 8. The mean relative quantity (RQ) differentials ($\log_e$-base scale)±95% CI of INSR, IR-A, and IR-B in normal (n=19) were $1.03 \times 10^{-8} \pm 0.17$, $-7.37 \times 10^{-9} \pm 0.24$, and $3.37 \times 10^{-8} \pm 0.18$, respectively. The mean relative quantity (RQ) differentials (log 2-base scale) ±95% CI of INSR, IR-A, and IR-B in tumor (n=42) were −0.88±0.25, −0.07±0.29, and −2.08±0.25, respectively. A two-tailed Welch's t-test analysis indicate that the levels of mRNA of INSR and IR-B are significantly lower in the tested breast tumor set when compared to the normal beast tissue (p<0.0001). Alternatively, no significant differences were observed in the mRNA levels of IR-A in breast cancer when compared with normal (p=0.4501).

Figure 9:
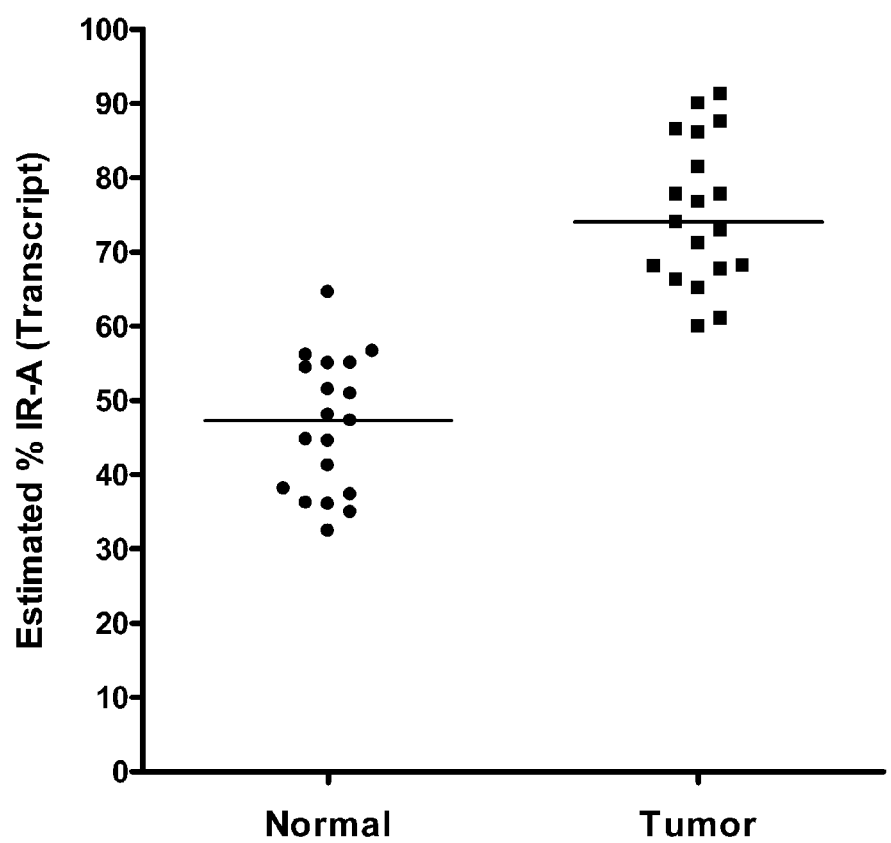
FIG. 9 shows the proportion of IR-A expression in matched normal breast and breast cancer specimens. Within sample proportion of insulin receptor isoform-A (IR-A) relative to total insulin receptor composition (i.e., IR-A+IR-B) as determined by $2^{(-\Delta Ct)}$ calculation. A paired sample t-test analysis indicated that a significant difference exists for calculated IR-A proportion between matched normal and tumor samples (P<0.001). Black bars represent the median IR-A proportion (%) within the normal (46.60±4.74, mean %±95% CI) and tumor (75.24±5.03, mean %±95% CI) tissue.

The proportion of IR-A relative to total insulin receptor composition (i.e. IR-A+IR-B) in matched tumor and normal pairs was calculated by $2^{(-\Delta Ct)}$. The results are shown in FIG. 9. The mean IR-A transcript proportion (%)±95% CI for the normal panel (n=19) was 46.60%±4.74%, while the mean IR-A transcript proportion (%)±95% CI for the matched tumor samples was 75.24%±5.02. A paired sample t-test analysis indicated that a significant increase of the calculated IR-A proportion in tumor samples exists when compared to matched normals (p<0.0001). Results suggest that the significantly decreased IR-B levels in tumor contribute to an over all increase the proportion of IR-A in tumor samples compared to normal.

Figure 10:
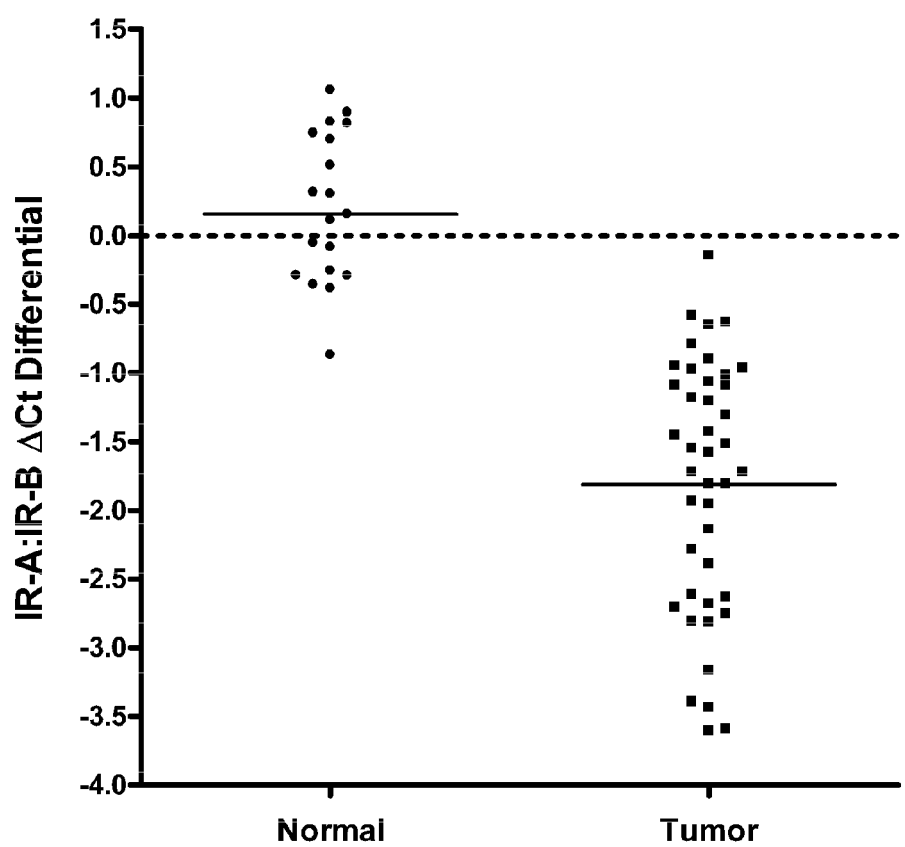
FIG. 10 shows increased IR-A:IR-B ratio in primary breast cancer. Calculated ΔCt differentials of insulin receptor isoforms IR-A and IR-B in normal (n=19) and tumor (n=42) breast samples. ΔCt differentials (IR-A ΔCt−IR-B ΔCt) values were calculated for all samples utilizing the within-sample reference gene panel (average Ct) for normalization purposes. A two-tailed Welch's t-test analysis identified a significant difference between normal and tumor samples in relation to observed IR-A:IR-B ΔCt differential (P<0.001). Black bars represent the median IR-A:IR-B ΔCt differential within a particular tissue-type.

In order to assess the mRNA transcript ratios of IR-A and IR-B, we calculated ΔCt differentials of IR-A and IR-B in normal and primary tumor breast samples. The ΔCt differentials (IR-A ΔCt–IR-B ΔCt) values were calculated for all samples utilizing the within-sample reference gene (housekeeping) panel (average Ct) for normalization purposes. The mean IR-A:IR-B ΔCt±95% CI was 0.20±0.23 for normal (n=19) and the mean IR-A:IR-B ΔCt±95% CI was −1.81±0.27 in primary tumors (n=42). A two-tailed Welch's t-test analysis identified a significant difference between normal and tumor samples in relation to observed IR-A:IR-B ΔCt (p<0.0001) (FIG. 10). The results indicated a significant increased ratio of IR-A to IR-B in breast tumors.

Figure 11:
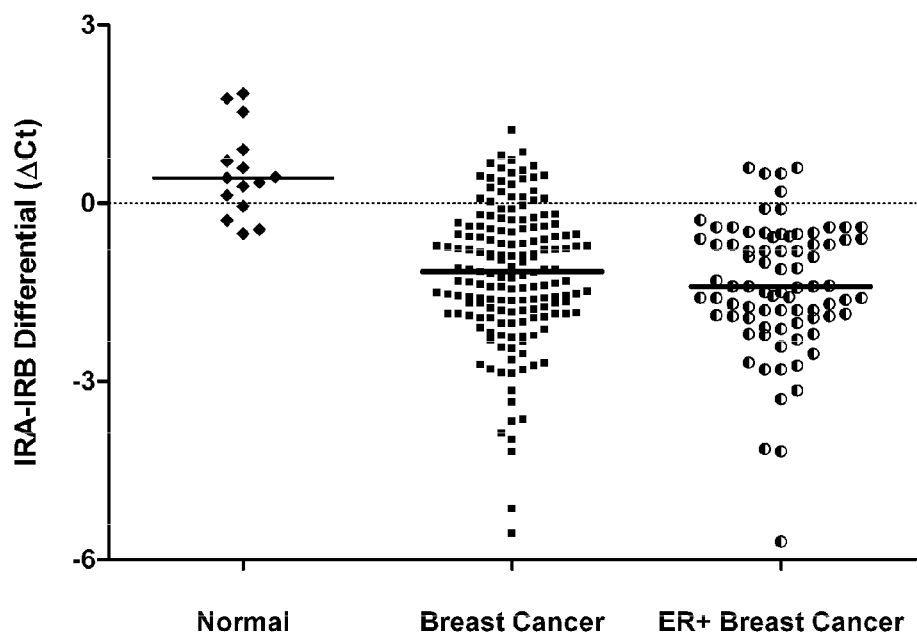
FIG. 11 shows an increased IR-A:IR-B ratio in breast cancer samples from qPCR cDNA array. Calculated ΔCt differentials of insulin receptor isoforms IR-A and IR-B (Y axis) in normal (n=15; samples from 10 independent donors), breast cancer cDNA panels (n=165), and breast tumors from these cDNA panels with >2-fold estrogen receptor (ER) over-expression (n=83). ΔCt differentials (IR-A ΔCt−IR-B ΔCt) values were calculated for all samples utilizing the within-sample reference gene panel (average Ct) for normalization purposes. A two-tailed Welch's t-test analysis identified a significant difference between normal and tumor samples in relation to observed IR-A:IR-B ΔCt differential (P<0.0001). Bars represent the mean IR-A:IR-B ΔCt differential within a particular tissue-type.

To further validate the above results, we assessed mRNA expression ratios of IR-A and IR-B in more breast cancer tissue samples. PCR arrays containing cDNAs from 15 normal breast tissues and 165 breast adenocarcinoma tissues were used. Equal amounts of cDNA were pre-amplified and assayed for expression levels of IR-A, IR-B, and ER by Taqman qPCR (Fluidigm). The ΔCt differentials (IR-A ΔCt–IR-B ΔCt) values were calculated for all samples utilizing the within-sample reference gene panel (ACTB, GUSB, GAPDH) for normalization purposes. The results are shown in FIG. 11. The mean IR-A:IR-B ΔCt±95% CI was 0.51±0.37 in normal tissues (n=15). The mean IR-A:IR-B ΔCt±95% CI was −1.19±0.17 across all breast cancers examined (n=165).

We then separated the breast cancer samples into those that displayed an estrogen receptor over-expression of 2-fold relative to normal breast tissue and compared their IR-A:IR-B ΔCt differentials to normal tissue and to all breast cancer samples. The results are shown in FIG. 11. The mean IR-A:IR-B ΔCt±95% CI was −1.48±0.39 in ER+ breast cancers (n=83), which is very similar to that observed across the whole breast cancer dataset. A two-tailed Welch's t-test analysis identified a significant difference between normal and tumor samples in relation to observed IR-A:IR-B ΔCt differential (p<0.0001).

Correlating IR-A: IR-B Ratio with Genes Involved in Breast Cancer Proliferation

Figure 12:
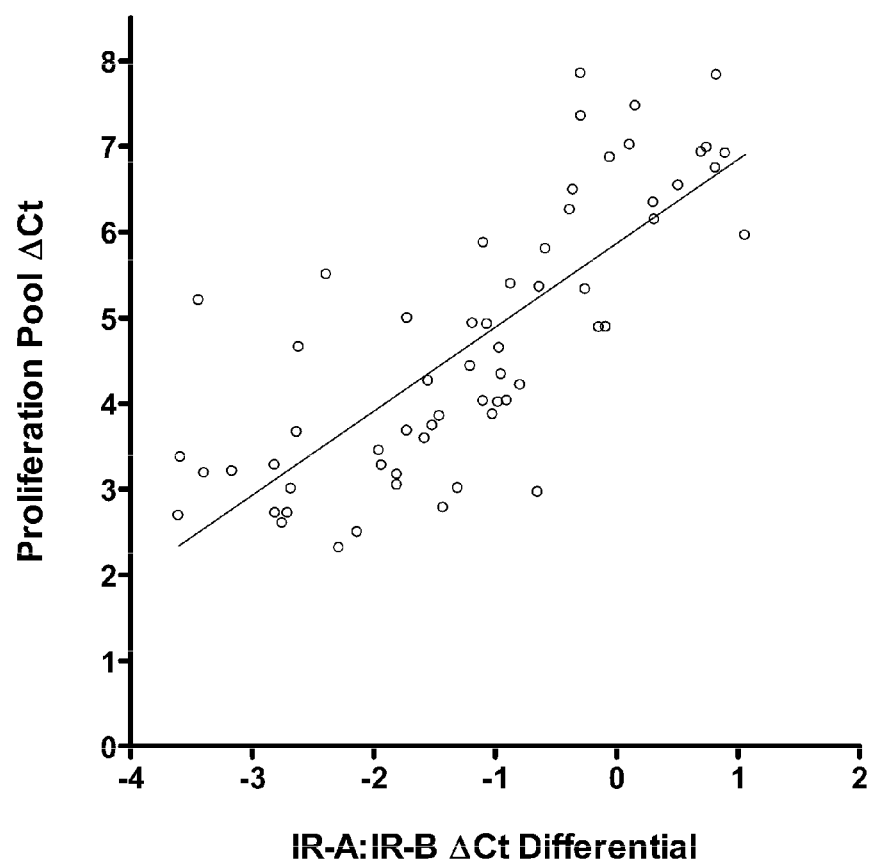
FIG. 12 shows a correlation of IR-A:IR-B ΔCt differential with the expression of proliferation genes. Linear regression analysis of the relationship between calculated IR-A:IR-B ΔCt differential (Y axis) and a pooled panel of proliferation markers (AURKA, BIRC5, CCNB1, KI67, and MYBL2) (X axis). Proliferation panel summary values were calculated by taking the mean ΔCt across all markers for a particular sample. Summary results for both normal and tumor samples are presented. The linear regression analysis results suggest a positive correlation between the two summary values (adjusted $R^2$=0.595).

Ki67, STK15, Survivin, CCNB1, MYBL2 are well characterized genes involved in breast cancer proliferation. The composite expression score of these genes has been used in Oncotype DX and is an important factor contributing to the breast cancer recurrence in many patients. We studied the relationship of the IR-A:IR-B ratio and the proliferation score in the primary breast cancer sample sets using regression and correlation analyses. Linear regression analysis was conducted to quantify the relationship between the calculated IR-A:IR-B ΔCt differential and a pooled panel of proliferation markers (AURKA, BIRC5, CCNB1, KI67, and MYBL2). Proliferation panel summary values were calculated by taking the average ΔCt across all markers for a particular sample. Summary results for both normal and tumor samples are presented. The linear regression analysis results suggest a positive correlation between the two summary values (adjusted $r^2$=0.595) (FIG. 12). The IR-A:IR-B ΔCt differential exhibits a positive correlation with the proliferation score (FIG. 12). The results suggest that the decreasing IR-B expression in tumor and increasing IR-A proportion expression may contribute tumor proliferation in ER+ PR+ and Her− breast cancer.

IR-A:IR-B ΔCt Differential in Breast Cancer Subtypes.

Breast cancer is a heterogeneous disease with respect to molecular alterations, cellular composition, and clinical outcome. Using an intrinsic gene list, ER positive breast cancers can be further classified by hierarchical cluster analysis into luminal-A, and luminal-B subtypes (Perou C M, 2000). Luminal-A cancers are histologically low-grade and sensitive to neo-adjuvant endocrine therapy (Creighton C et al 2008). In contrast, luminal-B cancers are often histologically high-grade and less sensitive to neo-adjuvant endocrine therapy, with a shorter time to poor outcome events (Creighton C et al 2008). Creighton reported that an IGF-I signature is manifested in luminal-B breast cancers and this signature is both highly correlated with numerous poor prognostic factors and one of the strongest indicators of disease outcome. Since the IR-A isoform is one of the important components involved the IGF signaling, we investigated the hypothesis that alterations in IR-A:IR-B ratios may be evident when comparing luminal-A and luminal-B breast cancers.

To address this question we conducted whole genome array analysis on 40 ER+ PR+ and Her2− negative breast tumor and 15 normal breast samples. We initially utilized a published PAM50-gene shrunken centroid classifier (Weigelt, et al. 2010). Samples were classified as luminal A or luminal B according to a Spearman's rank correlation, where the subtype with the highest correlation value was assigned to a particular sample. IR-A:IR-B ΔCt differentials in the normal, luminal-A and luminal-B were then compared. The scatter plot representation of calculated IR-A:IR-B ΔCt differentials with regards to sample subtype (normal, luminal-A, or luminal-B) are shown in FIG. 13A. The mean IR-A:IR-B ΔCt±95% CI was 0.27±0.30 in normal (n=15). The mean IR-A:IR-B ΔCt±95% CI was −1.09±0.34 in luminal-A classified breast cancers (n=13). The mean IR-A:IR-B ΔCt±95% CI was −2.12±0.34 in luminal-B classified breast cancers (n=27). All subtype pair-wise comparisons display a significant difference (two-sample t-test, p<0.001). The results indicated that IR-A:IR-B ratios in luminal-B patients changed more drastically than luminal-A patients.

In addition to the shrunken centroid classifier, we utilized GC-RMA normalized GeneChip data to identify a panel of differentially expressed transcripts by a two-sample Welch's t-test analysis. Samples were divided into two groups (normal or tumor) based on pathology assessment prior to conducting the statistical analysis. Sub-populations identified by unsupervised hierarchical clustering were classified as normal, luminal-A, or luminal-B as a function of transcript panel composition. IR-A:IR-B ΔCt differentials in the normal, luminal-A and luminal-B were also compared. The results are shown in FIG. 13B. The mean IR-A:IR-B ΔCt±95% CI was 0.32±0.25 in normal (n=15). The mean IR-A:IR-B ΔCt±95% CI was −1.05±0.19 in luminal-A predicted breast cancers (n=18). The mean IR-A:IR-B ΔCt±95% CI was −2.42±0.32 in luminal-B predicted breast cancers (n=22). All subtype pair-wise comparisons display a significant difference (two-sample t-test, p<0.001).

REFERENCES

Belfiore A, Frittitta L, Costantino A, Frasca F, Pandini G, Sciacca L, Goldfine I D, Vigneri R Insulin receptors in breast cancer. Ann NY Acad Sci 784:173-188 1996

Chad J. Creighton, Angelo Casa, ZaWaunyka Lazard, Shixia Huang, Anna Tsimelzon, Susan G. Hilsenbeck, Charles Kent Osborne, and Adrian V. Lee Insulin-Like Growth Factor-I Activates Gene Transcription Programs Strongly Associated With Poor Breast Cancer Prognosis J Clin Oncol 26:4078-4085, 2008.

Frasca F, Pandini G, Scalia P, Sciacca L, Mineo R, Costantino A, Goldfine I D, Belfiore A, Vigneri R. Insulin receptor isoform A, a newly recognized, high-affinity insulin-like growth factor II receptor in fetal and cancer cells. Mol Cell Biol. May; 19(5):3278-88, 1999.

Kaaks R Nutrition, hormones, and breast cancer: Is insulin the missing link? Cancer Causes Control 7:605-627, 1996

Mathieu M-C, Clark G M, Allred D C, Goldfine I D, Vigneri R Insulin receptor expression and clinical outcome in node-negative breast cancer. Proc Assoc Am Physicians 109:565-571, 1997

Milazzo G, Giorgino F, Damante G, Sung C, Stampfer M R, Vigneri R, Goldfine I D, Belfiore A Insulin receptor expression and function in human breast cancer cell lines. Cancer Res 52:3924-3930, 1992

Moller D E, Yokota A, Caro J F, Flier J S. Tissue-specific expression of two alternatively spliced insulin receptor mRNAs in man. Mol Endocrinol. August; 3(8):1263-9, 1989.

Paik S A multigene assay to predict recurrence of tamoxifen-treated, node-negative breast cancer N Engl J Med; 351: 2817-26, 2004.

Parker J S, M Mullins and M C Cheang et al., Supervised risk predictor of breast cancer based on intrinsic subtypes, J Clin Oncol 27:116-167, 2009.

Perou C M, Sørlie T, Eisen M B, van de Rijn M, Jeffrey S S, Rees C A, Pollack J R, Ross D T, Johnsen H, Akslen L A, Fluge O, Pergamenschikov A, Williams C, Zhu S X, Lonning P E, Børresen-Dale A L, Brown P O, Botstein D. Molecular portraits of human breast tumours. Nature. August 17; 406(6797):747-52, 2000.

Papa V, Pezzino V, Costantino A, Belfiore A, Giuffrida D, Frittitta L, Vannelli G B, Brand R, Goldfine I D, Vigneri R Elevated insulin receptor content in human breast cancer. J Clin Invest 86:1503-1510, 1990

Papa V, Belfiore A Insulin receptors in breast cancer: biological and clinical role. J Endocrinol Invest 19:324-333, 1996

Osborne C K, Monaco M E, Lippman M E, Kahn C R Correlation among insulin binding, degradation, and biological activity in human breast cancer cells in long-term tissue culture. Cancer Res 38:94-102, 1978.

Seino S, Seino M, Nishi S, Bell G I. Structure of the human insulin receptor gene and characterization of its promoter. Proc Natl Acad Sci USA. January; 86(1):114-8, 1989.

Sciacca, et al, Oncogene. November 28; 21(54):8240-50.9, 2002.

While the disclosure above has been provided in detail with reference to preferred aspects thereof, it will be apparent to one skilled in the art that various changes can be made, and equivalents employed, without departing from the scope of the disclosure and the claims. All documents cited are incorporated by reference in their entireties.

What is claimed is:

1. A method for detecting or quantifying an insulin receptor isoform A (IR-A) nucleic acid in a biological sample or a sample of nucleic acids prepared from a biological sample, comprising the steps of:
   (i) contacting a biological sample or nucleic acids prepared from a biological sample with a primer set under conditions suitable for polymerase-based amplification;
   (ii) amplifying the IR-A nucleic acid by performing polymerase-based amplification; and
   (iii) detecting or quantifying the amplified IR-A nucleic acid using a kit;
wherein the kit is selected from:
   (a) a kit comprising a 20 nucleotide IR-A forward synthetic nucleic acid of a nucleotide sequence as set forth in SEQ ID NO: 3, a 20 nucleotide IR-A reverse synthetic nucleic acid of a nucleotide sequence as set forth in SEQ ID NO: 21, and
   a 14 nucleotide synthetic nucleic acid IR-A probe of a nucleotide sequence set forth in SEQ ID NO: 7, wherein the probe comprises a detectable label; or
   (b) a kit comprising a 22 nucleotide IR-A forward synthetic nucleic acid of a nucleotide sequence as set forth in SEQ ID NO: 5, an 18 nucleotide IR-A reverse synthetic nucleic acid of a nucleotide sequence as set forth in SEQ ID NO: 22, and
a 17 nucleotide synthetic nucleic acid IR-A probe of a nucleotide sequence as set forth in SEQ ID NO: 8 wherein the probe comprises a detectable label.

2. The method of claim 1, wherein the biological sample or nucleic acids prepared from a biological sample is contacted with a 20 nucleotide IR-A forward synthetic nucleic acid primer of the nucleotide sequence as set forth in SEQ ID NO: 3,
a 20 nucleotide IR-A reverse synthetic nucleic acid of the nucleotide sequence as set forth in SEQ ID NO: 21, and
a 14 nucleotide synthetic nucleic acid probe of the nucleotide sequence as set forth in SEQ ID NO: 7 comprising a detectable label.

3. The method of claim 1, wherein the biological sample or nucleic acids prepared from a biological sample is contacted with
a 22 nucleotide IR-A forward synthetic nucleic acid of the nucleotide sequence as set forth in SEQ ID NO: 5,
an 18 nucleotide IR-A reverse synthetic nucleic acid of the nucleotide sequence as set forth in SEQ ID NO: 22, and
a 17 nucleotide synthetic nucleic acid probe of a nucleotide sequence as set forth in SEQ ID NO: 8 comprising a detectable label.

4. A method for detecting or quantifying an Insulin Receptor Isoform B (IR-B) nucleic acid in a biological sample or in a sample of nucleic acids prepared from a biological sample comprising the steps of:
   (i) contacting the biological sample, or the nucleic acids prepared from a biological sample with a primer set under conditions suitable for polymerase-based amplification;
   (ii) amplifying the IR-B nucleic acid by performing polymerase-based amplification; and
   (iii) detecting or quantifying the amplified IR-B nucleic acid using a kit; wherein the kit comprises: a primer set of a 21 nucleotide IR-B forward synthetic nucleic acid of the nucleotide sequence as set forth in SEQ ID NO: 11; a 19 nucleotide IR-B reverse synthetic nucleic acid of the nucleotide sequence as set forth in SEQ ID NO: 12; and a 15 nucleotide synthetic nucleic acid IR-B probe, wherein the IR-B probe comprises a detectable label, and has a nucleotide sequence as set forth in SEQ ID NO: 13; SEQ ID NO: 14; or SEQ ID NO: 15.

5. The method of claim 1, wherein the detectable label is a fluorescent label.

6. The method of claim 2, wherein the detectable label is a fluorescent label.

7. The method of claim 3, wherein the detectable label is a fluorescent label.

8. The method of claim 4, wherein the detectable label is a fluorescent label.

9. A method for determining the IR-A:IR-B ratio in a biological sample or a sample of nucleic acids prepared from a biological sample, comprising quantifying IR-A by using the method of claim 1; and quantifying IR-B by using an IR-B forward synthetic nucleic acid of the nucleotide sequence as set forth in SEQ ID NO: 11, an IR-B reverse synthetic nucleic acid of the nucleotide sequence as set forth in SEQ ID NO: 12, and a 15 nucleotide synthetic nucleic acid IR-B probe, wherein the IR-B probe comprises a detectable label, and has a nucleotide sequence as set forth in SEQ ID NO: 13; SEQ ID NO: 14; or SEQ ID NO: 15; and determining the IR-A to IR-B ratio.

10. The method of claim 9, wherein the detectable label is a fluorescent label.

11. The method for determining the ratio of IR-A to IR-B of claim 9, wherein the method comprises quantifying IR-A by using an IR-A forward synthetic nucleic acid of a nucleotide sequence as set forth in SEQ ID NO: 3, a 20 nucleotide IR-A reverse synthetic nucleic acid of a nucleotide sequence as set forth in SEQ ID NO: 21, and a 14 nucleotide synthetic nucleic acid IR-A probe of a nucleotide sequence as set forth in SEQ ID NO: 7, wherein the probe comprises a detectable label; quantifying IR-B by using an IR-B forward synthetic nucleic acid of the nucleotide sequence as set forth in SEQ ID NO: 11, an IR-B reverse synthetic nucleic acid of the nucleotide sequence as set forth in SEQ ID NO: 12, and a 15 nucleotide synthetic nucleic acid IR-B probe, wherein the IR-B probe comprises a detectable label, and has a nucleotide sequence as set forth in SEQ ID NO: 13; and determining the IR-A to IR-B ratio.

12. The method of claim 11, wherein the detectable labels are fluorescent labels.

13. The method for determining the ratio of IR-A to IR-B of claim 9, wherein the method comprises: quantifying IR-A by using an IR-A forward synthetic nucleic acid of a nucleotide sequence as set forth in SEQ ID NO: 5, an 18 nucleotide IR-A reverse synthetic nucleic acid of a nucleotide sequence as set forth in SEQ ID NO: 22, and a 17 nucleotide synthetic nucleic acid IR-A probe of a nucleotide sequence as set forth in SEQ ID NO: 8, wherein the probe comprises a detectable label; quantifying IR-B by using an IR-B forward synthetic nucleic acid of the nucleotide sequence as set forth in SEQ ID NO: 11, an IR-B reverse synthetic nucleic acid of the nucleotide sequence as set forth in SEQ ID NO: 12, and a 15 nucleotide synthetic nucleic acid IR-B probe, wherein the IR-B probe has a detectable label attached at one end, and has a nucleotide sequence as set forth in SEQ ID NO: 13; and determining the IR-A to IR-B ratio.

14. The method of claim 13, wherein the detectable labels are fluorescent labels.

* * * * *